US008055033B2

(12) United States Patent
Nishimura et al.

(10) Patent No.: US 8,055,033 B2
(45) Date of Patent: Nov. 8, 2011

(54) MEDICAL IMAGE PROCESSING APPARATUS, LUMINAL IMAGE PROCESSING APPARATUS, LUMINAL IMAGE PROCESSING METHOD, AND PROGRAMS FOR THE SAME

(75) Inventors: Hirokazu Nishimura, Hachioji (JP); Jun Hasegawa, Hino (JP); Hideki Tanaka, Hino (JP); Ryoko Inoue, Hachioji (JP); Tetsuo Nonami, Hino (JP)

(73) Assignee: Olympus Corporation, Tokyo (JP)

( * ) Notice: Subject to any disclaimer, the term of this patent is extended or adjusted under 35 U.S.C. 154(b) by 1119 days.

(21) Appl. No.: 11/884,515

(22) PCT Filed: Feb. 10, 2006

(86) PCT No.: PCT/JP2006/302381
§ 371 (c)(1),
(2), (4) Date: Aug. 15, 2007

(87) PCT Pub. No.: WO2006/087981
PCT Pub. Date: Aug. 24, 2006

(65) Prior Publication Data
US 2009/0208071 A1 Aug. 20, 2009

(30) Foreign Application Priority Data

Feb. 15, 2005 (JP) ................................. 2005-038116
Feb. 15, 2005 (JP) ................................. 2005-038117

(51) Int. Cl.
*G06K 9/00* (2006.01)

(52) U.S. Cl. ....................................................... 382/128
(58) Field of Classification Search ........................ None
See application file for complete search history.

(56) References Cited

U.S. PATENT DOCUMENTS

| 6,514,082 B2 * | 2/2003 | Kaufman et al. ............. 434/262 |
| 6,516,217 B1 | 2/2003 | Tsujita |
| 7,813,538 B2 * | 10/2010 | Carroll et al. ................. 382/128 |

(Continued)

FOREIGN PATENT DOCUMENTS

JP          10-014864          1/1998

(Continued)

OTHER PUBLICATIONS

Meng et al., "Wireless robotic capsule endoscopy: state-of-the-art and challenges", Proc 5th World Congress on Intelligent Control and Automation, Jun. 2004, pp. 5561-5565.*

*Primary Examiner* — Tom Y Lu
*Assistant Examiner* — Thomas Conway
(74) *Attorney, Agent, or Firm* — Scully, Scott, Murphy & Presser, P.C.

(57) ABSTRACT

There is provided a medical image processing apparatus including an image-extracting section extracting a frame image from in vivo motion picture data picked up by an in vivo image pickup device or a plurality of consecutively picked-up still image data, and an image analysis section analyzing the frame image extracted by the image-extracting section to output an image analysis result. The image analysis section includes a first biological-feature detection section detecting a first biological feature, a second biological-feature detection section detecting, based on a detection result obtained by the first biological feature detection section, a second biological feature in a frame image picked up temporally before or after the image used for detection by the first biological feature detection section; and a condition determination section making a determination for a biological condition based on a detection result obtained by the second biological feature detection section to output the determination.

23 Claims, 43 Drawing Sheets

U.S. PATENT DOCUMENTS

2007/0066868 A1* 3/2007 Shikii .......................... 600/118

FOREIGN PATENT DOCUMENTS

| | | |
|---|---|---|
| JP | 2001-017379 | 1/2001 |
| JP | 2004-000645 | 1/2004 |
| JP | 2004-188026 | 7/2004 |
| JP | 2004-321603 | 11/2004 |
| JP | 2005-137395 | 6/2005 |
| JP | 2006-166990 | 6/2006 |
| WO | 02/073507 | 9/2002 |

* cited by examiner

| FRAME NUMBER | STILL IMAGE DATA | FRAME TIME |
|---|---|---|
| 0 | Vs0 | 00:00:00.000 |
| 1 | Vs1 | 00:00:00.033 |
| ⋮ | | |
| MAX_COUNT | VsM | 00:00:10.000 |

| FRAME NUMBER | ANALYSIS RESULT |
|---|---|
| 27 | SUSPECTED BARRETT ESOPHAGUS |
| 28 | SUSPECTED BARRETT ESOPHAGUS |
| ⋮ | |

| MAX_COUNT |
|---|
| MAX_N |
| ANALYSIS RESULT |
| ACQUISITION INTERVAL N |
| DETERMINATION REFERENCE VALUE |

PALISADE VESSEL END POINT BOUNDARY

EPITHELIUM BOUNDARY 34

PALISADE VESSEL END POINT BOUNDARY iTH RADIATION

P2 [i]   P1 [i]

EPITHELIUM BOUNDARY 34

O

PALISADE VESSEL END POINT BOUNDARY

34
EPITHELIUM
BOUNDARY

MEDICAL IMAGE PROCESSING APPARATUS, LUMINAL IMAGE PROCESSING APPARATUS, LUMINAL IMAGE PROCESSING METHOD, AND PROGRAMS FOR THE SAME

TECHNICAL FIELD

The present invention relates to a medical image processing apparatus that efficiently determines a condition of interest on the basis of a large amount of biological image data, a luminal image processing and a luminal image processing method which detect the cardia on the basis of images of the interior of the lumen, and programs for the apparatuses and method.

BACKGROUND ART

In general, in conventional endoscopic examinations using an endoscope, in vivo image data picked up by an endoscopic apparatus or an endoscopic observation apparatus are immediately displayed on a display device such as a CRT and externally stored as motion picture data. A physician views the motion pictures or views frame images in the motion pictures as still images, during or after examinations for diagnosis.

Further, in recent years, swallowable capsule endoscopes have been used.

For example, as disclosed in Japanese Patent Laid-Open No. 2004-645, image data picked up in vivo with an in-capsule endoscope is sequentially externally accumulated as motion picture data by radio communication. The physician views the motion pictures or views frame images in motion pictures as still images for diagnosis.

Furthermore, Japanese Patent Laid-Open No. 2004-188026 discloses an apparatus that applies an image analysis process on still images to display the results of the analysis on endoscopic images or in another display area.

The image analysis results allow the physician to make diagnosis on the basis of image analysis values for IHb, vessel analysis, and the like, which are objective determination criteria, without recourse of the physician's subjective.

However, when the physician views motion pictures after endoscopic examinations or views motion pictures picked up by an in-capsule endoscope, the enormous number of frame images contained in the motion pictures results in the need to make much effort in finding a point on the motion pictures at which a suspected lesion is shown, extracting each frame image showing the lesion and apply an image analysis process to the image, and making diagnosis on the basis of each image analysis result.

To solve this problem, a system can be implemented which uses the above image analysis apparatus for still images to apply the same image analysis process to all the frame images contained in the motion pictures and to then store the results.

However, the application of the same image analysis process to all the frame images increases processing time, resulting in the need to wait a long time until processing results are obtained. Further, a long time is required until appropriate processing results are obtained even if the image analysis process is applied with parameters changed. Another disadvantage is that this method increases the amount of data needing to be stored until appropriate processing results are obtained.

Furthermore, screening in examinations with an endoscopic apparatus determines whether or not the Barrett mucosa or the Barrett esophagus is present. The Barrett mucosa is developed when at the junction between the stomach and the esophagus (EG junction), the squamous epithelium forming the esophagus is replaced with the mucosa of the stomach under the effect of the reflux esophagitis or the like. The Barrett mucosa is also called the cylindrical epithelium. If the Barrett mucosa extends at least 3 cm from the mucosal boundary all along the circumference of a cross section of the lumen of the esophagus, the patient is diagnosed to have a disease called the Barrett esophagus.

The incidence of the Barrett esophagus has been increasing particularly among Americans and Europeans. The Barrett esophagus is very likely to develop into the adenocarcinoma and thus has been a major problem. Consequently, it is very important to discover the Barrett mucosa early.

Thus, medical image processing apparatus are desired to objectively determine biological feature values for the Barrett esophagus, the Barrett mucosa, or the like and to provide determinations to the operator.

Further, as described above, in the medical field, observation and diagnosis of the organs in the body cavity are widely performed using medical equipment having an image pickup function.

For example, in the diagnosis of the esophageal disease, in the case of the disease diagnosis of the Barrett esophagus near the EG junction (junction between the stomach and the esophagus) in the upper part of the cardia, which corresponds to the boundary between the stomach and the esophagus, endoscopic examinations are important for the diagnosis of the esophagus because the Barrett esophagus may develop into the adenocarcinoma as described above. An endoscope is inserted into a patient's mouth, and the physician makes the diagnosis of the esophageal disease while viewing endoscopic images displayed on a monitor screen.

Further, as described above, in recent years, capsule-like endoscopes have been developed which allow the physician to make the diagnosis of the esophageal disease while viewing images obtained with the capsule-like endoscope. A system has been proposed which detects the disease on the basis of biological images obtained with a capsule-like endoscope (see, for example, WO 02/073507 A2).

However, even the above proposed system does not disclose the detection of the cardia or the vicinity of the cardia boundary based on images showing an area extending from the esophagus to the stomach.

For example, enabling the cardia or the boundary of the cardia to be detected allows the physician to observe biological tissue images of the detected cardia or cardia boundary in detail. This enables the disease such as the Barrett esophagus to be quickly diagnosed.

OBJECT OF THE INVENTION

The present invention has been made in view of the above problems. An object of the present invention is to provide a medical image processing apparatus that can efficiently determine a condition of interest on the basis of a large amount of image data.

Another object of the present invention is to provide a luminal image processing apparatus that can detect the cardia on the basis of intraluminal images.

DISCLOSURE OF INVENTION

Means for Solving the Problem

A medical image processing apparatus in accordance with a first aspect of the present invention comprises an image extracting section that extracts a frame image from in vivo motion picture data picked up by an in vivo image pickup device or a plurality of consecutively picked-up still image data, and an image analysis section that analyzes the frame image extracted by the image extracting section to output an image analysis result. The image analysis section comprises a first biological feature detection section that detects a first biological feature, a second biological feature detection section that detects, on the basis of a detection result obtained by the first biological feature detection section, a second biological feature in a frame image picked up temporally before or after the image used for detection by the first biological feature detection section, and a condition determination section that determines a biological condition on the basis of a detection result obtained by the second biological feature detection section to output the determination.

A medical image processing method in accordance with a second aspect of the present invention comprises a step of extracting a frame image from in vivo motion picture data picked up by an in vivo image pickup device or a plurality of consecutively picked-up still image data, a step of analyzing the extracted frame image to detect a first biological feature, a step of detecting, on the basis of a result of the detection of the first biological feature, a second biological feature in a frame image picked up temporally before or after the image used for detection by the first biological feature detection section, and a step of making a determination for a biological condition on the basis of a result of the detection of the second biological feature to output the determination.

A program in accordance with a third aspect of the present invention allows a computer to execute a function of extracting a frame image from in vivo motion picture data picked up by an in vivo image pickup device or a plurality of consecutively picked-up still image data, a function of analyzing the extracted frame image to detect a first biological feature, a function of detecting, on the basis of a result of the detection of the first biological feature, a second biological feature in a frame image picked up temporally before or after the image used for detection by the first biological feature detection section, and a function of making a determination for a biological condition on the basis of a result of the detection of the second biological feature to output the determination.

A luminal image processing apparatus in accordance with a fourth aspect of the present invention comprises a feature value calculating section that calculates a predetermined feature value by executing image processing on one or a plurality of intraluminal images obtained by picking up an image of the gastrointestinal tract and a boundary detection section that detects a boundary of the gastrointestinal tract on the basis of the calculated feature value.

A luminal image processing method in accordance with the fourth aspect of the present invention comprises a step of calculating a predetermined feature value by executing image processing on one or a plurality of intraluminal images obtained by picking up an image of the gastrointestinal tract and a step of detecting a boundary of the gastrointestinal tract on the basis of the calculated feature value.

A program in accordance with the fourth aspect of the present invention allows a computer to execute a function of calculating a predetermined feature value from one or a plurality of intraluminal images obtained by picking up an image of the gastrointestinal tract and a function of detecting a boundary of the gastrointestinal tract on the basis of the calculated feature value.

BRIEF DESCRIPTION OF THE DRAWINGS

FIG. 15A is a diagram showing an example of an image illustrating an operation shown in FIG. 14 and the like;

FIG. 15B is a diagram showing an example of an image illustrating the operation shown in FIG. 14 and the like;

BEST MODE FOR CARRYING OUT THE INVENTION

Embodiments of the present invention will be described with reference to the drawings.

First Embodiment

Figure 1:
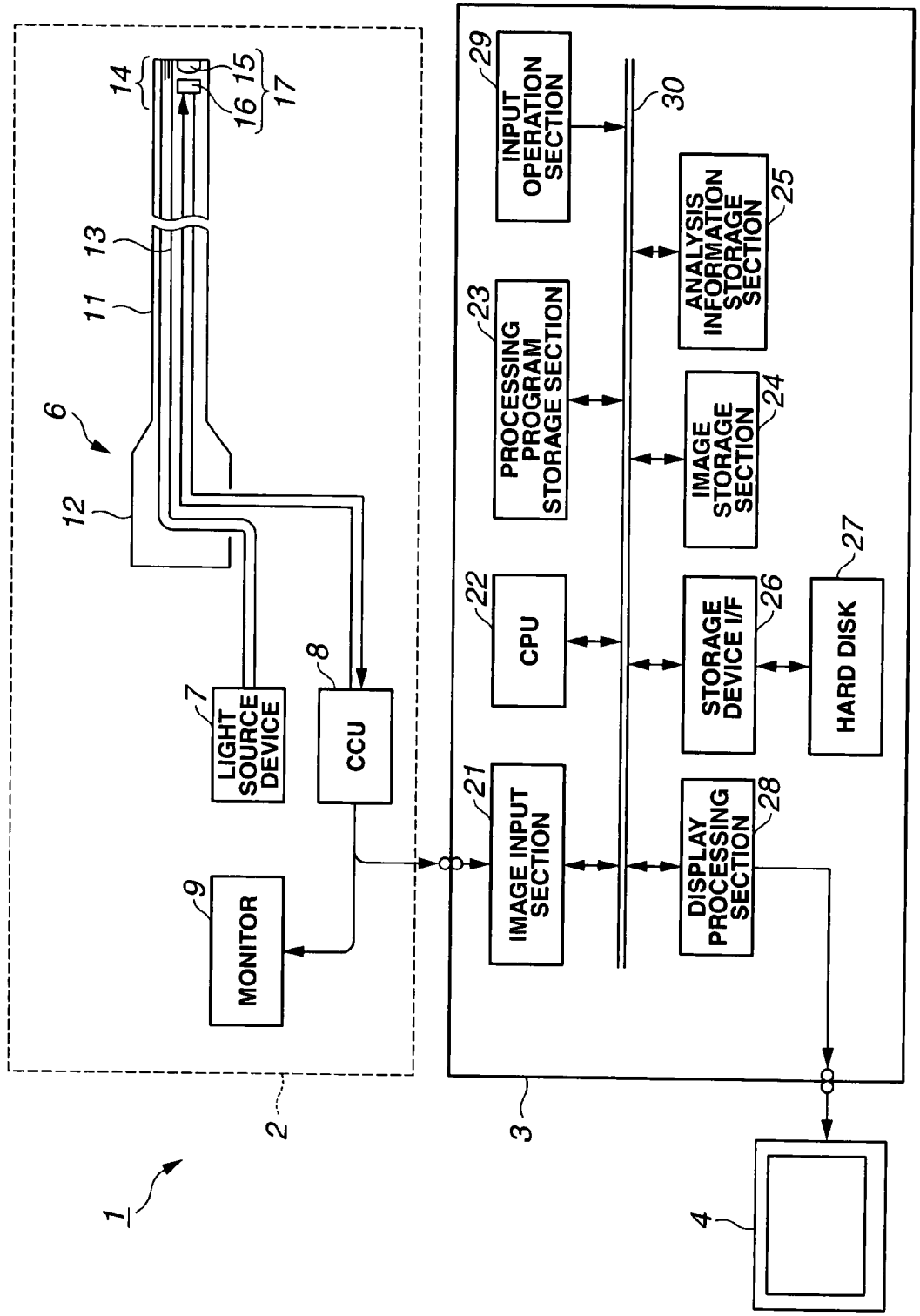
FIG. 1 is a block diagram showing the entire configuration of an endoscope system comprising a first embodiment.
Figure 2:
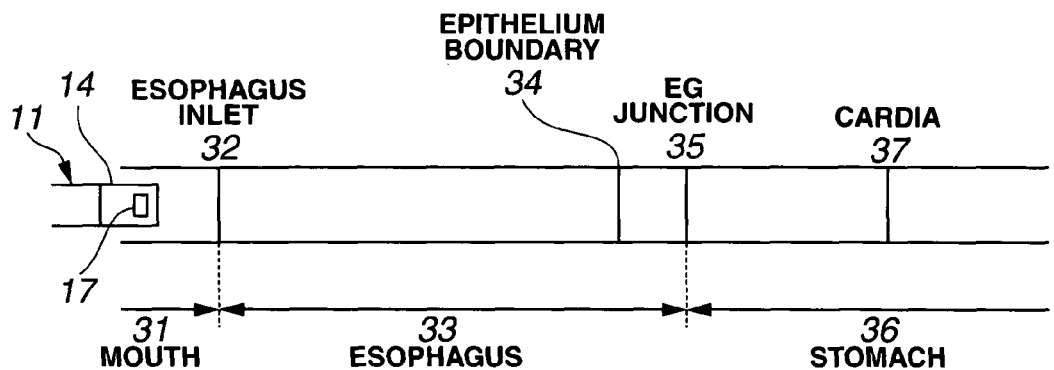
FIG. 2 is a diagram schematically showing the parts of the upper gastrointestinal tract endoscopically examined by orally inserting an endoscope.
Figure 3:
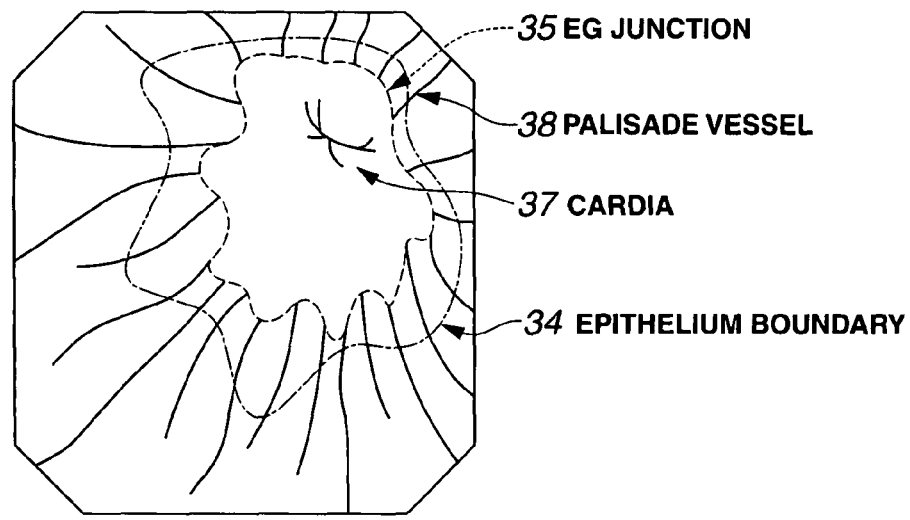
FIG. 3 is a diagram showing an example of an endoscopic image of the vicinity of the boundary between the esophagus and the stomach.
Figure 4:
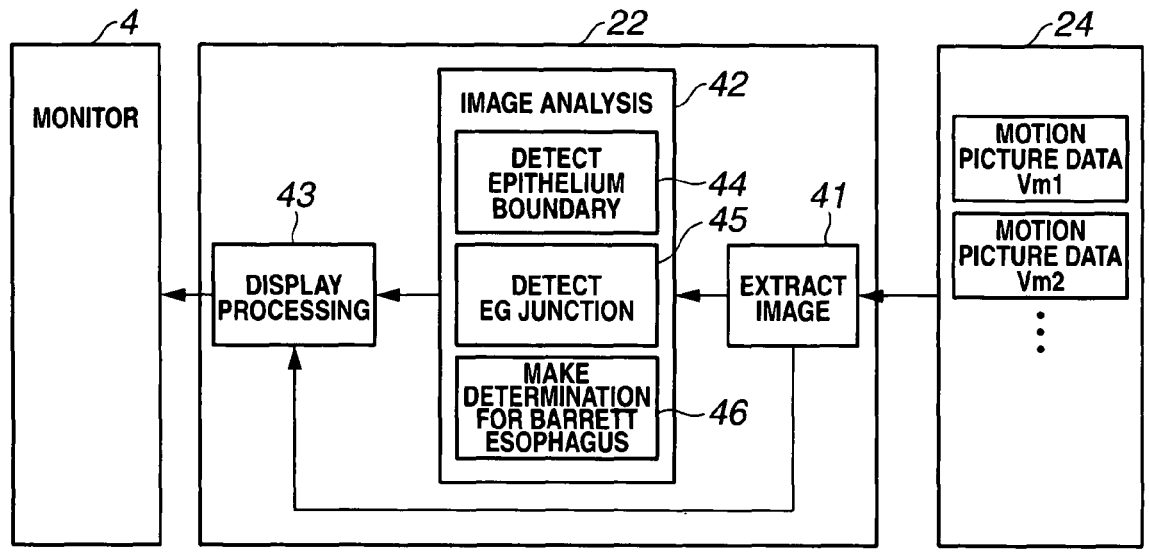
FIG. 4 is a diagram showing the functional configuration of essential sections of the image processing apparatus.
Figures 5, 6A, 6B, 7:
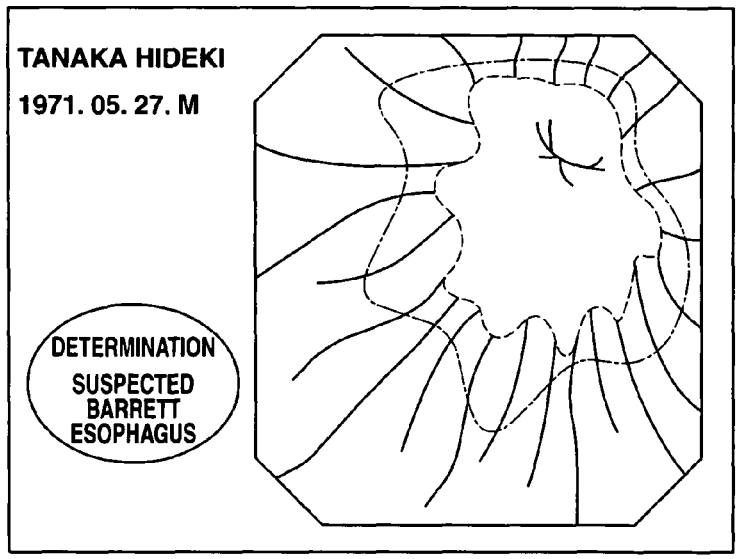
FIG. 5 is a diagram showing that motion picture data stored in an image storage section is stored as sets of still image data.
FIG. 6A is a diagram showing analysis results stored in an analysis information storage section.
FIG. 6B is a diagram showing an example of information used for an analysis process or set by a processing program storage section 23.
FIG. 7 is a diagram showing an example of a monitor display showing an analysis result together with an endoscopic image.

FIGS. 1 to 16 relate to a first embodiment. FIG. 1 shows the entire configuration of an endoscopic system comprising the present embodiment. FIG. 2 schematically shows the parts of the upper gastrointestinal tract endoscopically examined by orally inserting an endoscope. FIG. 3 shows an example of an endoscopic image of the vicinity of the boundary between the esophagus and the stomach. FIG. 4 shows the functional configuration of an image processing apparatus in accordance with the present embodiment. FIG. 5 shows that motion picture data stored in an image storage section is stored as sets of still image data.

Figure 8:
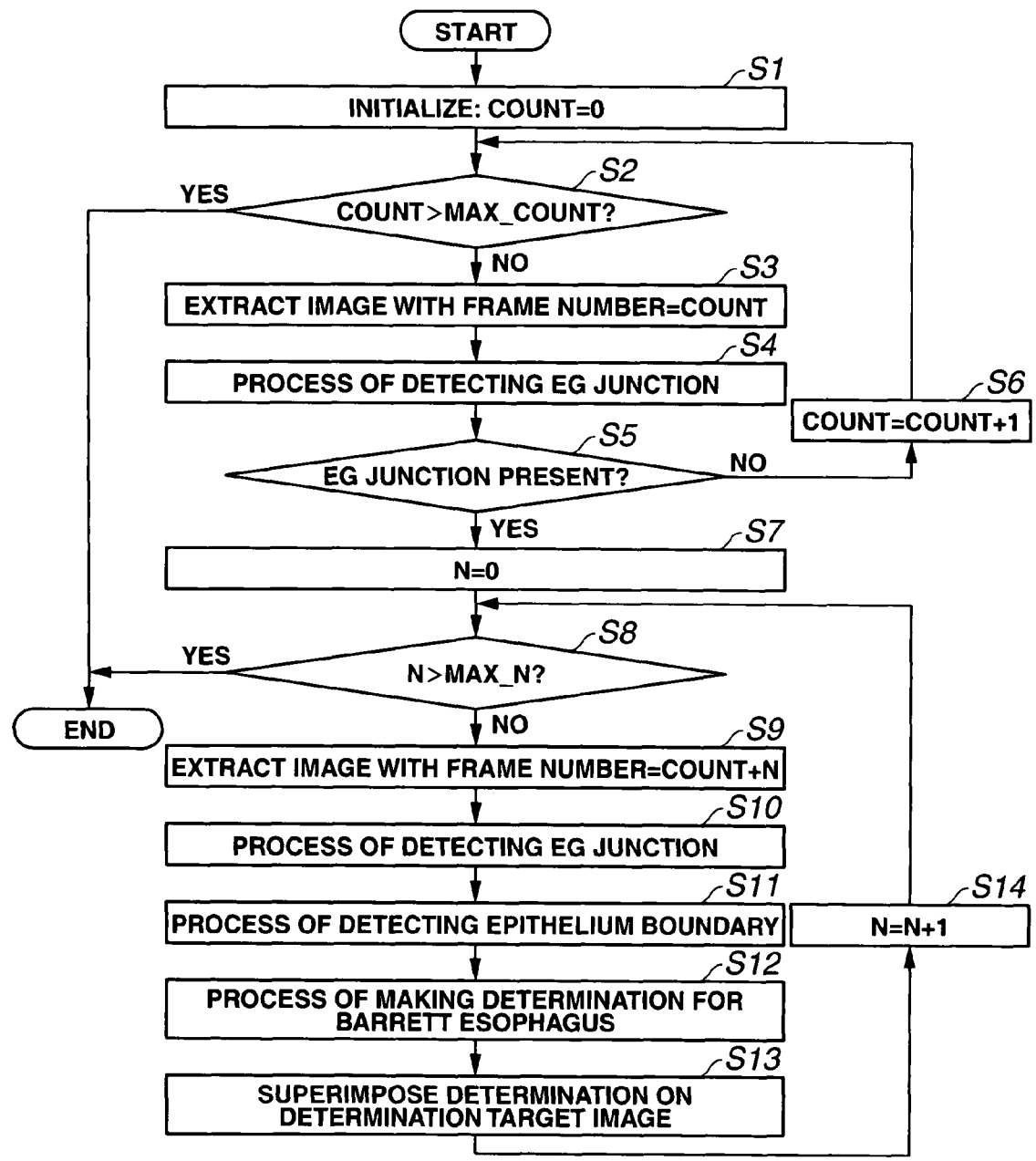
FIG. 8 is a flowchart of a process procedure for determining the Barrett esophagus condition.
Figure 9:
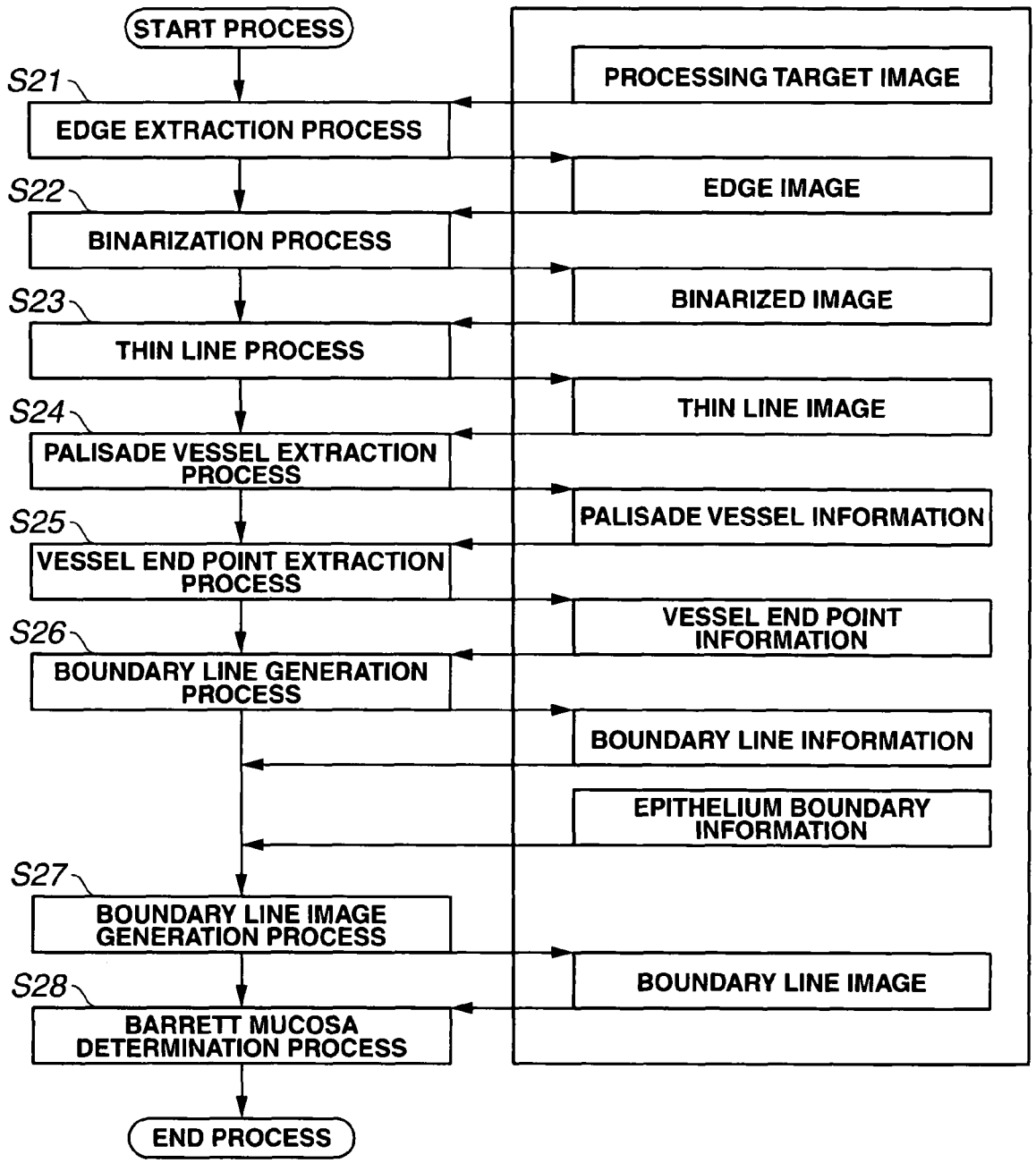
FIG. 9 is a flowchart showing a process procedure of executing a process of detecting the EG junction, together with information such as images used or generated in the procedure.

FIGS. 6A and 6B show analysis results stored in an analysis information storage section, information stored in a processing program storage section, and the like. FIG. 7 shows an example of a monitor display showing an analysis result together with an endoscopic image. FIG. 8 is a flowchart of a process procedure for determining the Barrett esophagus condition in accordance with the present embodiment. FIG. 9 shows a process procedure of executing a process of detecting the EG junction, together with information such as images used or generated.

Figure 10A:
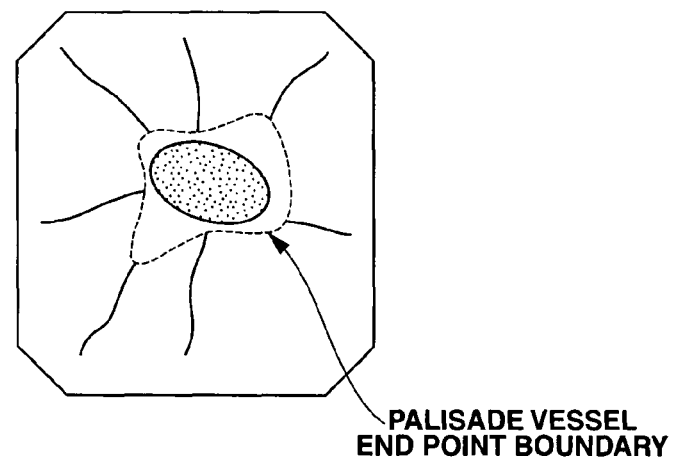
FIG. 10A is a diagram showing a palisade vessel end point boundary.
Figure 10B:
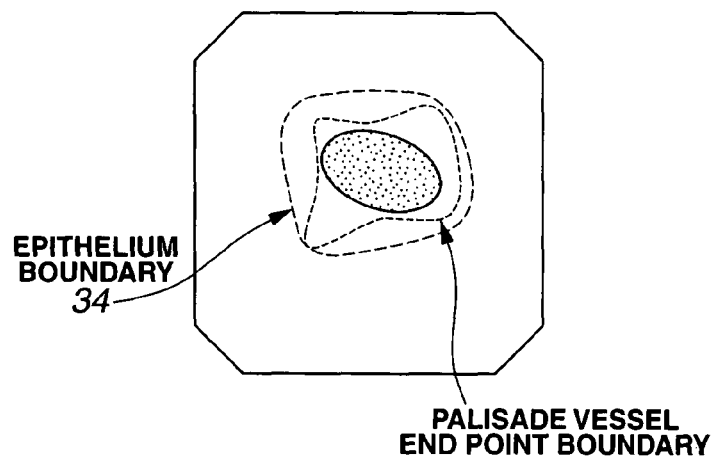
FIG. 10B is a diagram showing the palisade vessel end point boundary and an epithelium boundary.
Figure 10C:
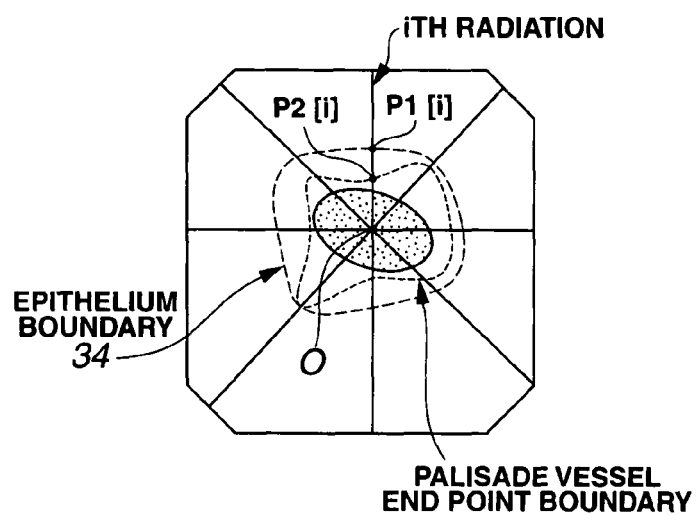
FIG. 10C is a diagram showing that an image of the palisade vessel end point boundary or the like is divided by eight radial lines.
Figure 11:
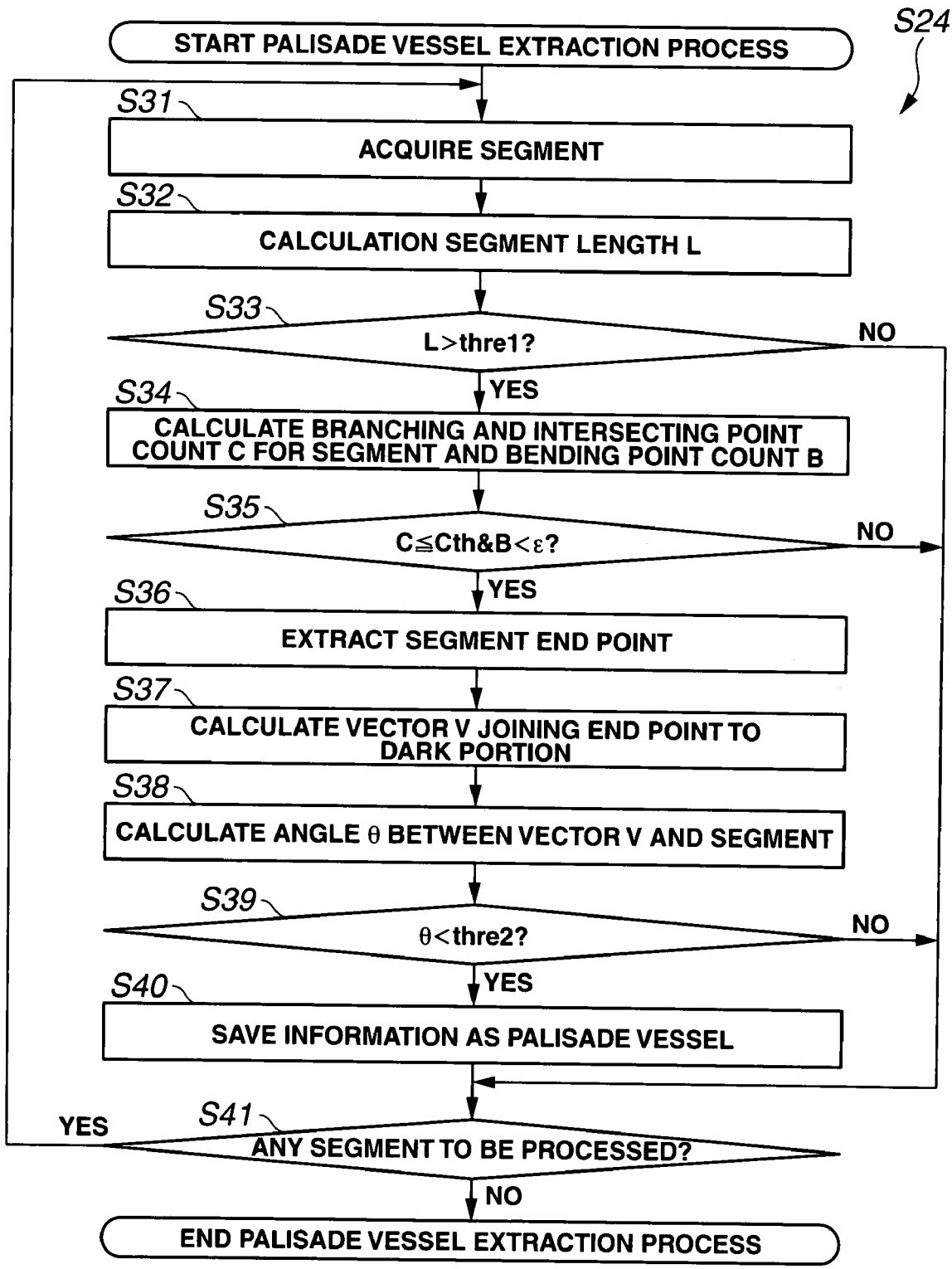
FIG. 11 is a flowchart showing the details of a palisade vessel extraction process shown in FIG. 9.
Figure 12A:
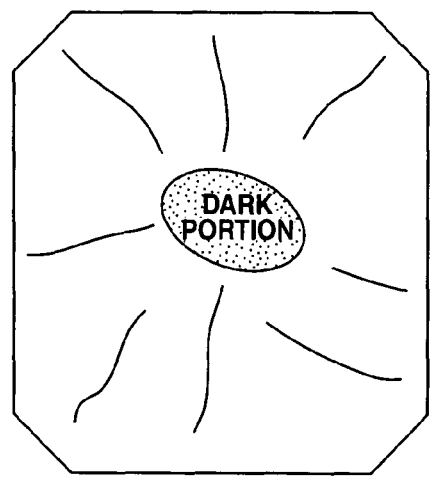
FIG. 12A is a diagram showing an example of an image illustrating an operation performed for the process shown in FIG. 11.
Figure 12B:
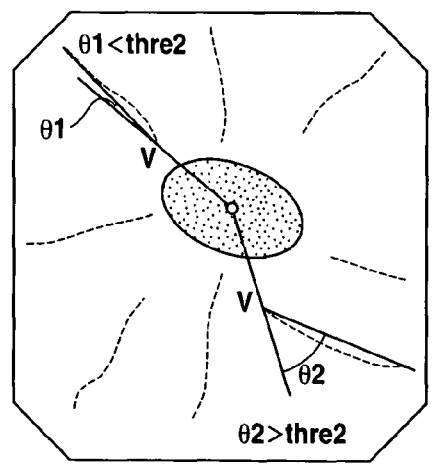
FIG. 12B is a diagram showing an example of an image illustrating an operation performed for the process shown in FIG. 11.
Figure 12C:
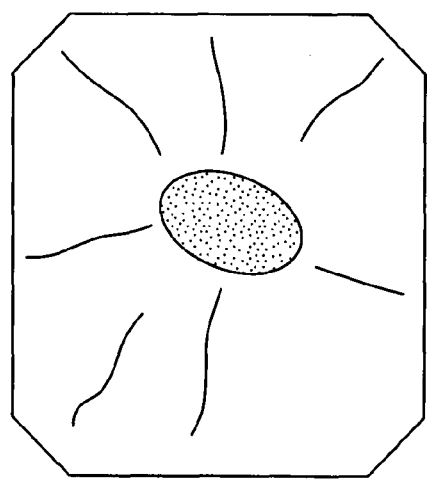
FIG. 12C is a diagram showing an example of an image illustrating an operation performed for the process shown in FIG. 11.
Figure 13:
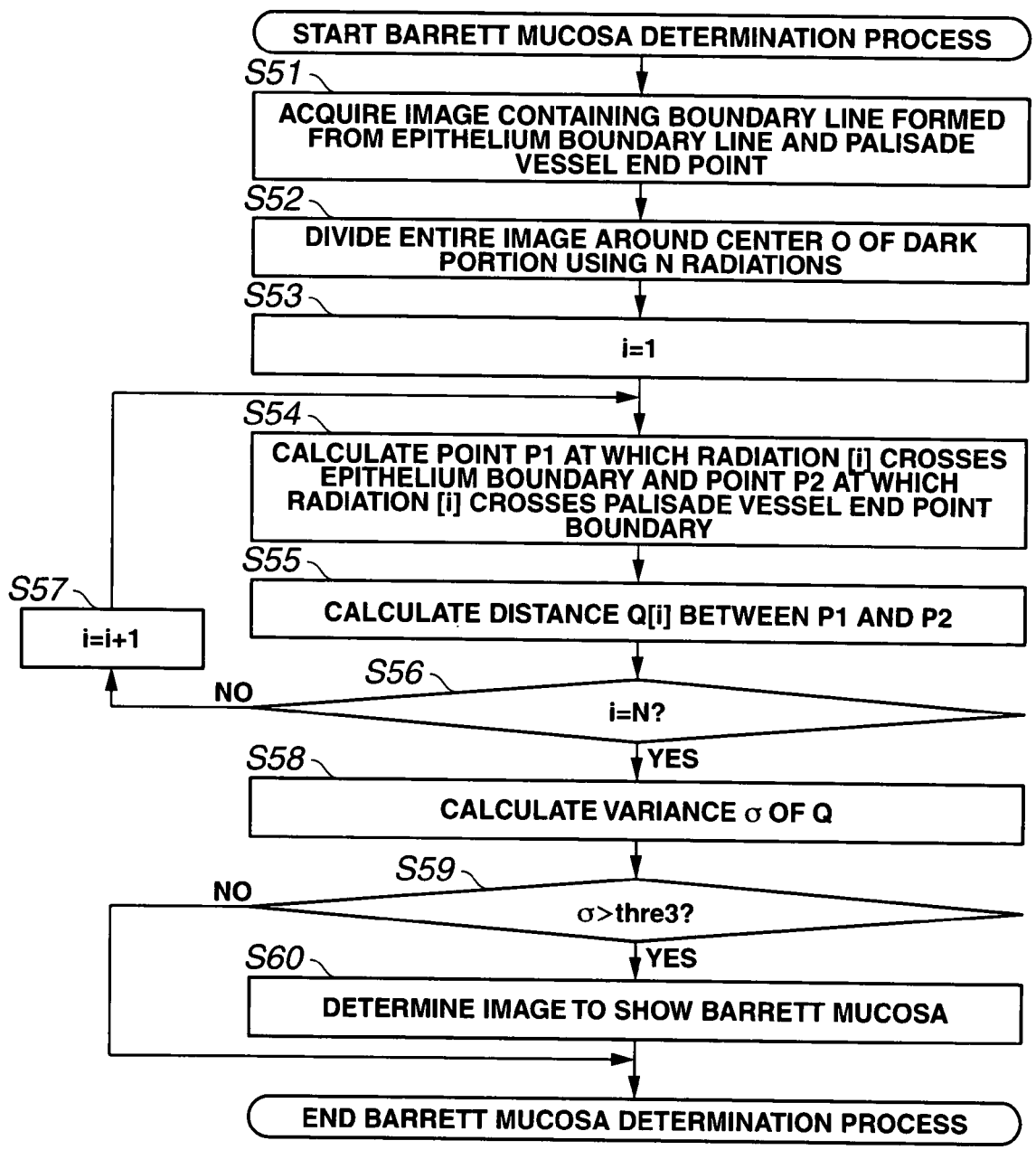
FIG. 13 is a flowchart showing the details of a Barrett mucosa determination process shown in FIG. 10.
Figure 14:
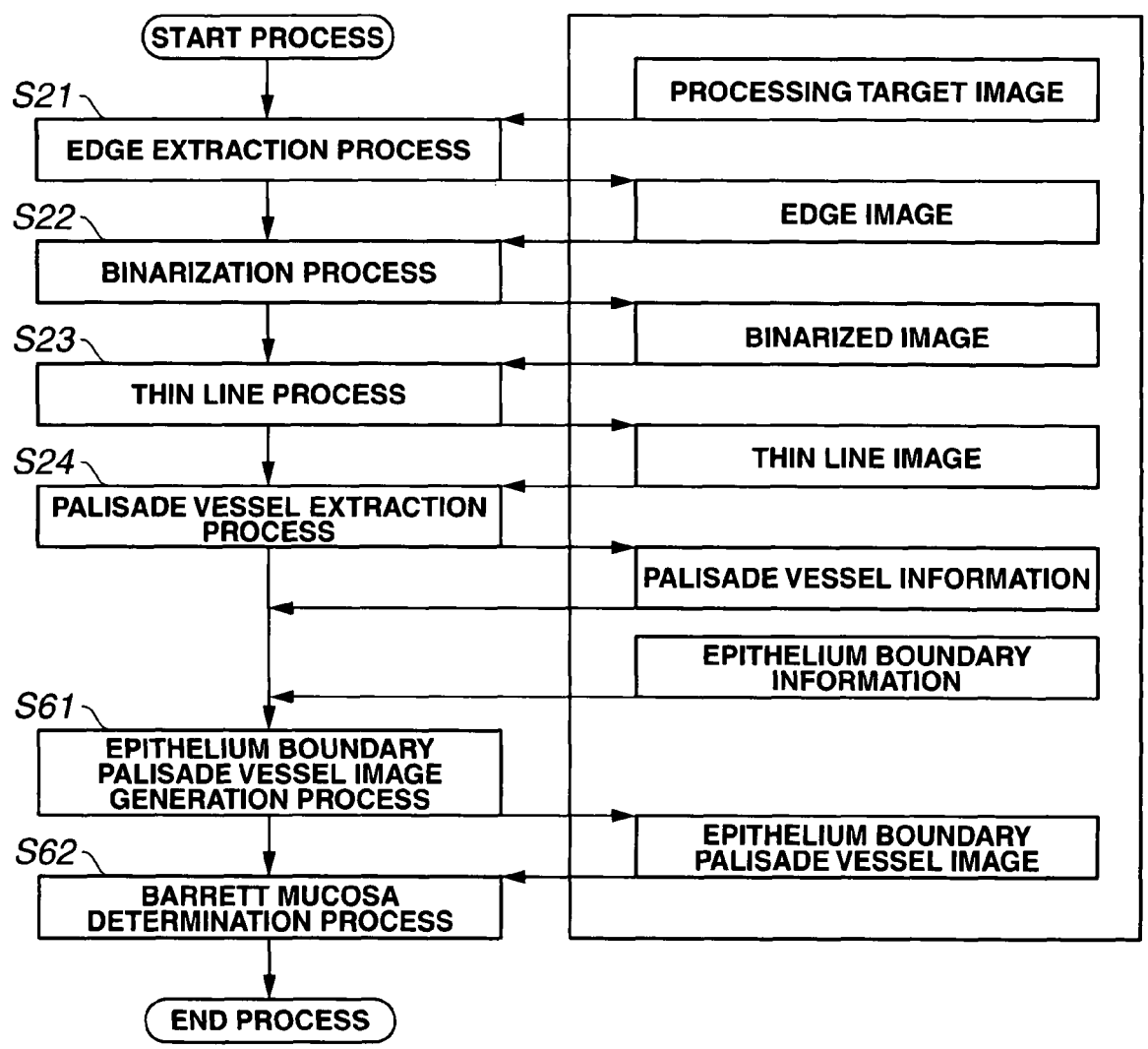
FIG. 14 is a flowchart of a variation of the process shown in FIG. 9.
Figure 15A:
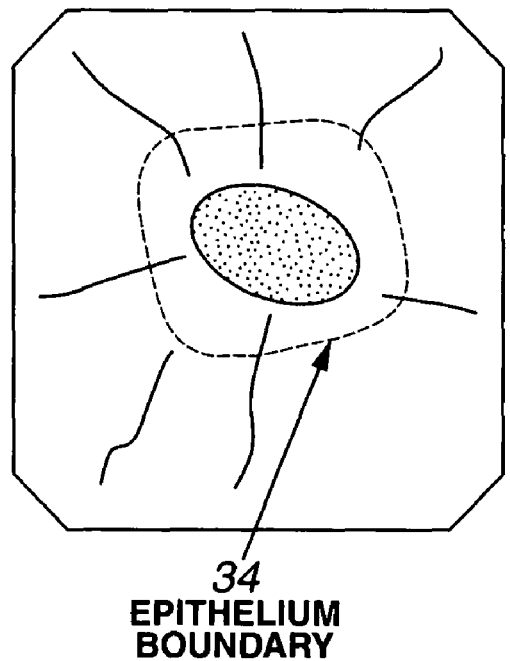
Figure 15B:
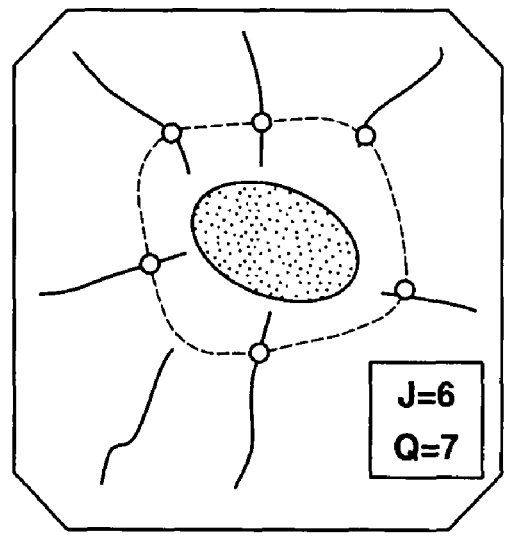
Figure 16:
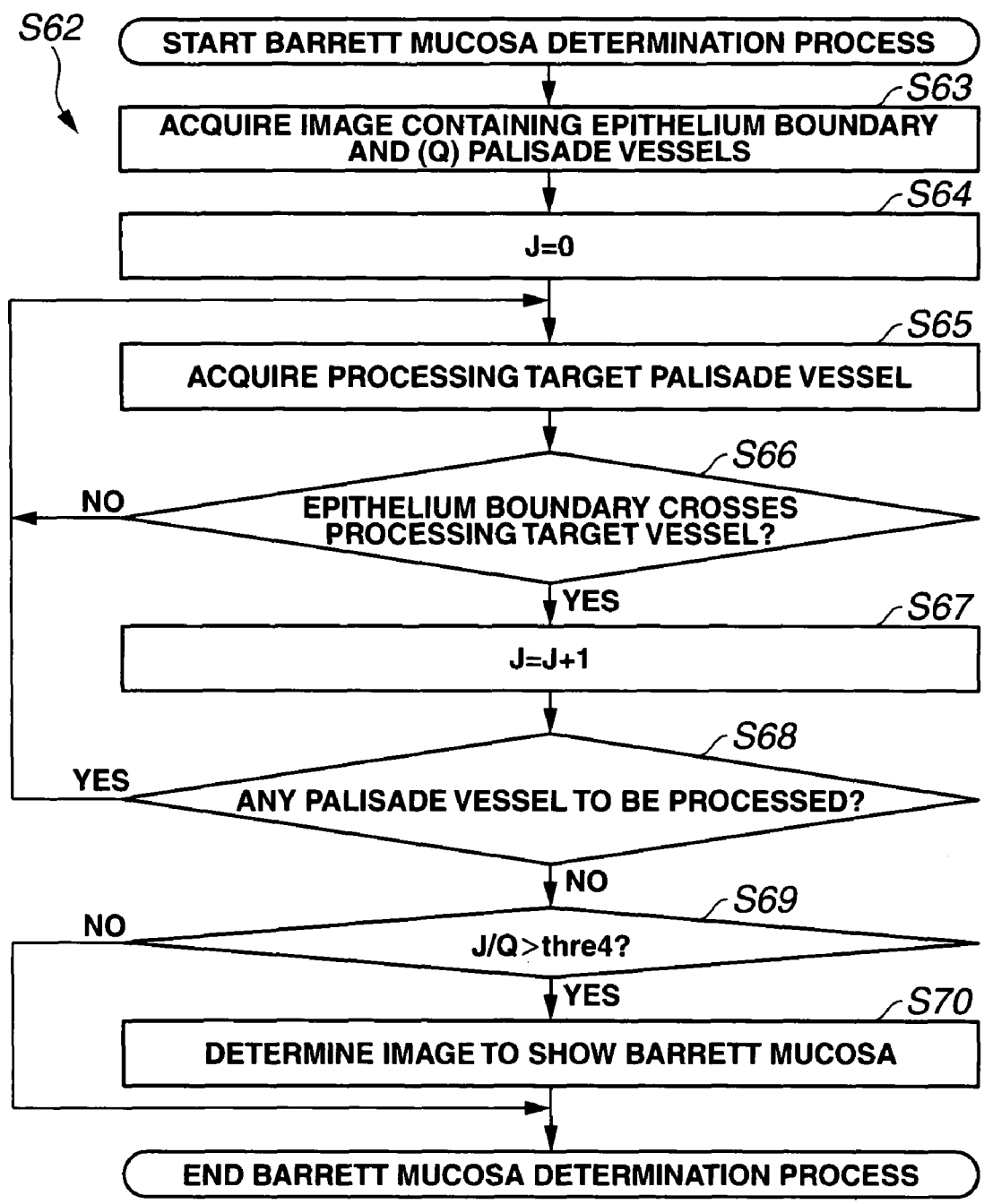
FIG. 16 is a flowchart showing the details of the Barrett mucosa determination process shown in FIG. 14.

FIGS. 10A to 10C are diagrams showing the boundary of an end point of the palisade vessel. FIG. 11 is a flowchart of a palisade vessel extraction process shown in FIG. 9. FIGS. 12A to 12C show an example of an image illustrating an operation performed for the process shown in FIG. 11. FIG. 13 is a flowchart of a Barrett mucosa determination process shown in FIG. 10. FIG. 14 is a flowchart of a variation of the process shown in FIG. 9. FIGS. 15A and 15B show an example of an image illustrating an operation shown in FIG. 14 and the like. FIG. 16 is a flowchart of the Barrett mucosa determination process in FIG. 14.

An endoscopic system 1 shown in FIG. 1 is composed of an endoscopic observation apparatus 2, a medical image processing apparatus (hereinafter simply referred to as an image processing apparatus) 3 composed of a personal computer or the like to execute image processing on images obtained by the endoscopic observation apparatus 2, and a monitor 4 that displays the images subjected to the image processing by the image processing apparatus 3.

The endoscopic observation apparatus 2 has an endoscope 6 forming an in vivo image pickup device inserted into the lumen to pick up images of the interior of the body, a light source device 7 that supplies illumination light to the endoscope 6, a camera control unit (hereinafter simply referred to as a CCU) 8 that executes signal processing for the image pickup means of the endoscope 6, and a monitor 9 to which video signals outputted by the CCU 8 are inputted to display endoscopic images picked up by an image pickup device.

The endoscope 6 has an insertion portion 11 inserted in the body cavity and an operation portion 12 provided at a trailing end of the insertion portion 11. Further, a light guide 13 is placed inside the insertion portion 11 to transmit illumination light.

A trailing end of the light guide 13 is connected to the light source device 7. Illumination light supplied by the light source device 7 is transmitted by the light guide 13. The (transmitted) illumination light is then emitted from a distal plane attached to an illumination window provided at a distal end 14 of the insertion portion 11 to illuminate a subject such as a diseased part.

An image pickup apparatus 17 is provided which comprises an objective lens 15 attached to an observation window located adjacent to the illumination window and for example, a charge coupled device (hereinafter referred to as a CCD) 16 located at a position where the objective lens 15 forms an image and serving as a solid-state image pickup device. An optical image formed on an image pickup surface of the CCD 16 is photoelectrically converted by the CCD 16.

The CCD 16 is connected to the CCU 8 via a signal line to output the photoelectrically converted image signal in response to the application of a CCD driving signal from the CCU 8. The image signal is subjected to signal processing by a video processing circuit in the CCU 8 and thus converted into a video signal. The video signal is outputted to the monitor 9, which thus displays the endoscopic image on a display surface thereof. The video signal is also inputted to the image processing apparatus 3.

In the present embodiment, the endoscope 6 is used in the following case. The distal end 14 of the insertion portion 11 of the endoscope 6 is inserted through the mouth of the patient down to the vicinity of the boundary between the esophagus and the stomach to determine whether or not the Barrett mucosa is present near the boundary; the Barrett mucosa is the normal mucosa (specifically, the squamous epithelium) of the esophagus, the mucosa to be detected, modified to exhibit the condition of the mucosa part of the stomach.

In this case, a video signal corresponding to an endoscopic image obtained by picking up an image of the surface of the biological mucosa in the body is also inputted to the image processing apparatus 3. An image processing method described below is executed on the video signal to detect (determine) whether or not the Barrett mucosa is present or the state of a disease called the Barrett esophagus has been reached.

The image processing apparatus 3 has an image input section 21 to which a video signal corresponding to the endoscopic image inputted by the endoscopic observation apparatus 2 is inputted, a CPU 22 serving as a central processing unit to execute image processing on image data inputted by the image input section 21, and a processing program storage section 23 that stores a processing program (control program) that allows the CPU 22 to execute image processing.

Further, the image processing apparatus 3 has an image storage section 24 that stores image data and the like inputted by the image input section 21, an analysis information storage section 25 that stores analysis information and the like processed by the CPU 22, a hard disk 27 serving as a storage device that stores the image data, analysis information, and the like processed by the CPU 22, via a storage device interface 26, a display processing section 28 that executes a display process for displaying the image data and the like processed by the CPU 22, and an input operation section 29 comprising a keyboard and the like and used by the user to input data such as image processing parameters and to perform instruction operations.

The video signal generated by the display processing section 28 is outputted to the display monitor 4 to display the processed image subjected to image processing, on the display surface of the display monitor 4. The image input section 21, the CPU 22, the processing program storage section 23, the image storage section 24, the analysis information storage section 25, the storage device interface 26, the display processing section 28, and the input operation section 29 are connected together via a data bus 30.

In the present embodiment, an examination or diagnosis target site is the circumferential portion of the junction between the esophagus and the stomach. An image obtained by the endoscope 6 is subjected to image analysis to determine whether or not a suspected site of the Barrett esophagus is present, that is, to make a condition determination.

Thus, the insertion portion 11 of the endoscope 6 is inserted into the patient's mouth from the distal end of the insertion portion 11 to perform image pickup. FIG. 2 is a figure showing a luminal site in which the distal end of the endoscope is positioned when the endoscope 6 is orally inserted into the body cavity of the patient. The distal end 14 of the endoscope 6 is inserted into the mouth 31 and advances from the esophagus inlet 32 into the esophagus 33. The distal end 14 of the endoscope 6 moves through the epithelium boundary 34 and the EG junction 35 to the stomach 36 and then via the cardia 37 to the interior of the stomach 36.

The operation of inserting the endoscope 6 allows the acquisition of motion picture data picked up in the above order. The motion picture data thus acquired is stored in the image storage section 24. Image analysis is executed on frame images of still images constituting the motion picture data.

FIG. 3 is a schematic diagram of an example of a picked-up endoscopic image of the vicinity of the boundary between the esophagus 33 and the stomach 36. In the endoscopic image, the cardia 37 is an inlet to the interior of the stomach and is opened and closed.

The palisade vessels 38 substantially radially running outside the cardia 37 are present only in the esophagus 33 side. The palisade vessels 38 extend in the vertical direction along the lumen of the esophagus 33.

Further, an area extending from the epithelium boundary 34 (shown by an alternate long and short dash line) corresponding to the boundary between the mucosal tissue in the esophagus 33 side and the mucosal tissue in the stomach 36 side to the cardia has a very reddish mucosal color tone (the epithelium in which this color tone is distributed is called the columnar epithelium). An area extending in the opposite direction has a whitish mucosal color tone (the epithelium in which this color tone is distributed is called the squamous epithelium). This enables the epithelium boundary to be determined by endoscopic observations.

A line (shown by a dashed line) joining the end points of the palisade vessels 38 together is a boundary line (in fact, the line is not present) that cannot be easily identified by endoscopic observations. The line is called the EG junction 35 and corresponds to the tissue boundary between the stomach 36 and the esophagus 33.

The epithelium boundary 34 is normally located near the EG junction 35. However, if the reflux esophagitis or the like replaces the squamous epithelium forming the esophagus 33 with the mucosa (columnar epithelium or Barrett mucosa) of the stomach 36, the epithelium boundary 39 rises toward the esophagus 33.

If the Barrett mucosa is formed at least 3 cm away from the normal mucosal boundary all along the circumference of the cross section of the esophagus lumen, the patient is diagnosed to have the Barrett esophagus.

FIG. 4 shows the functional configuration of essential sections of the image processing apparatus 3.

Image data on motion pictures with its image picked up by the endoscope 6 and inputted to the image processing apparatus 3 is stored, as motion picture data Vm1, Vm2, . . . , in the image storage section 24, serving as image storage (image recording) means.

In this case, the motion picture data Vm1, Vm2, . . . have a data structure in which still images are accumulated over time. Thus, when the motion picture data Vm1, Vm2, . . . are stored in the image storage section 24, for example, as shown in FIG. 5, frame numbers 0, 1, . . . , MAX_COUNT are assigned to the still image data, which are thus labeled as Vs0, Vs1, . . . , VsM (M=MAX_COUNT).

Further, frame time simultaneously stored in the image storage section 24 is stored. The still image data may be compressed in accordance with JPEG or the like before being stored.

When image processing is started, the CPU 22 and processing program allow an image extracting block 41 composed of software to extract and read the still image data within the range indicated by specified frame numbers from, for example, the motion picture data Vm1 read from the image storage section 24. The image extracting block 41 constitutes an image extracting section that extracts frame image data from in vivo motion picture data or data on a plurality of consecutively picked-up still images.

Extracted still image data are sequentially sent to an image analysis block 42 and a display processing block 43.

The image analysis block 42 comprises an epithelium boundary detection block 44 that detects epithelium boundary, an EG junction detection block 45 that detects the EG junction, and a Barrett esophagus determination block 46 that determines whether or not the patient has the Barrett esophagus. The image analysis block 42 constitutes an image analysis section that analyzes the frame image extracted by the image extracting block 41 to output an image analysis result.

The epithelium boundary detection block 44, for example, detects a variation in mucosa color tone in an image as an edge to detect an epithelium boundary line present in the image as a point sequence.

The EG junction detection block 45, for example, detects a line joining the end points of the palisade vessels together as a point sequence (a method for detection will be described below in detail).

The Barrett esophagus determination block 46 calculates feature values such as the shape of the epithelium boundary, the striped residue of the squamous epithelium, the distance between the epithelium boundary and the EG junction, the standard deviation of the distance, and the maximum and minimum values of the distance to determine whether or not the target site with its image picked up indicates the Barrett esophagus.

Information on the determination made by the Barrett esophagus determination block 46 is stored in the analysis information storage section 25, and sent to the display processing block 43. The information on the determination based on the analysis executed by the image analysis block 42 is displayed in a still image shown on the monitor 4 via the image extracting block 41.

FIG. 6A shows an example of analysis results stored in the analysis information storage section 25. FIG. 6B shows an example of information used or set when the processing program storage section 23 executes an analysis process.

Further, FIG. 7 shows a display example in which information on a determination is displayed in an analyzed still image on the monitor 4.

As described with reference to FIG. 8, to make a condition determination of whether or not any still image data in the motion picture data contains the Barrett esophagus, the present embodiment determines whether or not an image of a reference site (in the present embodiment, the EG junction) comprising a first biological feature (value) was picked up temporally before or after (substantially simultaneously with) the pickup of an image of a determination target site to be subjected to a Barrett esophagus condition determination. The EG junction detection block 45 constitutes a first biological feature detection section that detects the first biological feature.

The present embodiment is characterized by executing such an image processing procedure as described below if the determination process determines that an image of the reference site has been picked up. A second biological feature (value) (in the present embodiment, a feature of the epithelium boundary) is detected in a still image in a frame following or preceding the frame of the reference site. Then, on the basis of the detection result of the second biological feature, a Barrett esophagus determination is made. This allows an efficient determination to be made for the Barrett esophagus condition, the condition determination target. The epithelium boundary detection block 44 constitutes a second biological feature detection section that detects the second biological feature in the frame image picked up temporally before or after the image used for the detection by the EG junction detection block 45, on the basis of the detection result from the EG junction detection block 45.

Such image analysis processing makes it possible to omit, for example, a process of detecting the second biological feature in images not comprising the first biological feature. This allows a condition determination to be efficiently made for the condition determination target in a short time. A large amount of image data can thus be appropriately processed.

Now, with reference to the flowchart in FIG. 8, description will be given of the operation of the image processing apparatus 3 in accordance with the present embodiment.

When the user uses the input operation section 29 to specify a file name for motion picture data to the CPU 22, which executes a process in accordance with a processing program, the CPU 22 reads the maximum number of frames for the specified motion picture data, from the image storage section 24. As shown in FIG. 6B, the maximum frame number is substituted into a parameter MAX-COUNT indicating the maximum frame number to start a process in accordance with the processing program.

In the first step S1, the CPU 22 initializes a frame number variable COUNT, that is, sets COUNT=0.

In the next step S2, the CPU 22 compares the frame number variable COUNT with MAX_COUNT. If COUNT>MAX_COUNT, the process is ended.

If step S2 results in the opposite determination, that is, COUNT≦MAX_COUNT, the process proceeds to step S3 where the image extracting block 41 extracts an image with a frame number=COUNT.

In the next step S4, the EG junction detection block 45 executes, in accordance with the present embodiment, a process of detecting the EG junction in the image with that frame number as a process of detecting the first biological feature (the biological feature is hereinafter simply referred to as the feature).

Depending on whether or not the detection result indicates a point sequence of a line indicating the EG junction 35, the CPU 22 determines whether or not the EG junction 35 is present as shown in step S5.

If the CPU 22 determines in step S5 that the EG junction 35 is not present, the CPU 22 suspends the process in steps S3 and S4 to proceed to the next step S6. The CPU 22 then increments the frame number variable COUNT by one and returns to step S2 to repeat the process in steps S2 to S6.

On the other hand, in step S5, if the CPU 22 determines that the EG junction 35 is present, the CPU 22 detects the second feature in step S7, and on the basis of the detection result, shifts to a condition determination process of determining whether or not the patient has the Barrett esophagus, the condition determination target.

In step S7, to start the Barrett esophagus determination process, the CPU 22 sets the variable N, specifically, sets the variable N at 0.

In the next step S8, the CPU 22 compares the variable N with a predetermined constant MAX_N, more specifically, the maximum frame number for which the process of determining whether or not the patient has the Barrett esophagus is to be executed. Then, if the comparison result indicates N>MAX_N, the CPU 22 ends the process. The present embodiment thus avoids determining whether or not the patient has the Barrett esophagus, for images with frame numbers following the preset maximum frame number.

On the other hand, if step S8 results in the opposite comparison result, that is, N≦MAX_N, the process proceeds to step S9, where the image extracting block 41 extracts an image with a frame number=COUNT+N. That is, an image is extracted which is located temporally N frames after the image in which the EG junction 35 is detected (At this time, N is 0, that is, the initial value. Accordingly, the Barrett esophagus determination process is executed on the basis of the image in which the EG junction 35 has been detected. As is apparent from the subsequent process, whether or not the patient has the Barrett esophagus is sequentially executed on images picked up temporally after the one in which the EG junction 35 has been detected).

Then, in step S10, the EG junction detection block 45 executes a process of detecting the EG junction 35 in the image with that frame number.

In the next step S11, the epithelium boundary detection block 44 executes a process of detecting the epithelium boundary 34 in the image with that frame number as a process of detecting the second feature. The process of detecting the epithelium boundary 34 corresponds to, for example, the process from step S1 to step S4 shown in FIG. 4 of Japanese Patent Application No. 2004-360319. Specifically, since the squamous epithelium in the esophagus side has a color tone different from that of the columnar epithelium in the stomach side as described above, the coordinates of the epithelium boundary 34 can be calculated (detected) by executing an edge process and a thinning process on endoscopic image data and then joining a generated sequence of points for the boundary together to obtain a coordinate point sequence along the boundary.

In the next step S12, the Barrett esophagus determination block 46 uses the point sequence for the line indicating the EG junction 35 detected in step S10 and the point sequence for the line indicating the epithelium boundary 34 detected in step S11 to determine whether or not the condition determination target site in the picked-up image is the Barrett esophagus. The Barrett esophagus determination block 46 constitutes a condition determination section that make a determination for the condition of a living body on the basis of the detection result from the epithelium boundary detection section 44 to output a determination.

Specifically, a process described in connection with a Barrett esophagus determination process shown in FIG. 13 described below makes it possible to determine whether or not the patient has the Barrett esophagus.

In step S13, the Barrett esophagus determination block 46 passes the determination of whether or not the target site is the Barrett esophagus and the frame number to the display processing block 43. The display processing block 43 extracts image data indicated by the specified frame number from an internal buffer (not shown) and superimposes the determination on the image data. The image data is sent to the monitor 4, which displays the image together with the determination on the display screen.

For example, if the target site is determined to be the Barrett esophagus, then as shown in FIG. 6B, for example, "suspected Barrett esophagus" is displayed in the determination target image.

In step S14 subsequent to step S13, the variable N is incremented by one, and then the process returns to step S8. The process from step S8 to step S14 is then repeated. Thus, when the variable N exceeds the maximum value MAX_N, the process is ended.

According to the present embodiment configured as described above and executing the process described above, to analyze images to determine whether or not analysis target still image data constituting motion picture data on picked-up endoscopic images shows the Barrett esophagus, the process of detecting an image having the feature of the EG junction 35 is executed in order of picked-up images, the EG junction 35 constituting the end points of the palisade vessels, which are present around the periphery of the Barrett esophagus determination site. The process of detecting the feature of the epithelium boundary 34, required to make a determination for the Barrett esophagus condition, is then executed on images following the one determined by the above process to have the feature of the EG junction 35. Then, on the basis of the detection result, the positional relationship between the epithelium boundary 34 and the EG junction 35, and the like, the apparatus determines whether or not the target site is the Barrett esophagus. This makes it possible to efficiently determine whether or not the target site is the Barrett esophagus.

Further, determinations can be made for the Barrett esophagus and the Barrett mucosa (Barrett epithelium), which is a pre-symptom of the Barrett esophagus disease as described below. This enables determinations suitable for early treatments.

Further, the present embodiment presets the maximum frame number for the condition determination of whether or not the target site is the Barrett esophagus to avoid the condition determination of whether or not the target site is the Barrett esophagus, for images with frame numbers following the maximum frame number. This makes it possible to prevent time from being spent on images that need not be subjected to the condition determination of whether or not the target site is the Barrett esophagus.

That is, if images of the interior of the esophagus 33 are sequentially picked up starting with the mouth 31 and ending with the interior of the stomach 36, that is, the interior of the cardia 37, as shown in FIG. 2, then the image of the interior of the stomach need not be subjected to the condition determination of whether or not the target site is the Barrett esophagus. In this case, setting the frame number of the stomach image at MAX_N makes it possible to avoid the condition determination of whether or not the target site is the Barrett esophagus.

Now, the process of detecting the EG junction 35 will be described with reference to FIGS. 9 to 13. Description will be given below of an image analysis process of detecting the EG junction 35 and then detecting the epithelium boundary 34 and making a determination for the Barrett mucosa. The image analysis process is intended to provide an apparatus and method for appropriately determining whether or not the target site is the Barrett mucosa. The image analysis process makes it possible to appropriately determine whether or not the target site is the Barrett mucosa.

FIG. 9 shows the relevant process procedure, data generated, and the like. The left of FIG. 9 shows the contents of the process, and information such as images generated is shown inside a frame in the right of the figure.

When the image analysis process is started, in the first step S21, an edge extraction process is executed on a process target image. The edge extraction process generates an edge image by for example, applying a bandpass filter to a G color component image in an RGB image.

The edge extraction technique based on the bandpass filter is well known. An edge image may also be generated using a luminance component of the processing target image. If not only the edge of the vessel but also the edge of another shape (contour) is extracted, the vessel edge alone can be extracted by applying the bandpass filter to the R component of the processing target image to exclude the edge of the extracted shape.

Steps S21 to S26 in FIG. 9 are used for a processing section corresponding to the stomach/esophagus detection process in step S4 in FIG. 8.

In the next step S22 in FIG. 9, a binarization is executed on the edge image to generate a binarized image. The binarization in accordance with the present embodiment compares the pixel value of each pixel in the edge image with a specified threshold to determine the value of each pixel in the binarized image to be 0 or 1.

In the next step S23, a well-known thinning technique is applied to the binarized image to execute a thinning process to generate a thinned image.

In the next step S24, a palisade vessel extraction process of extracting the palisade vessels inherent in the esophagus 33 is executed on the thinned image. Extracted palisade vessel information is saved. A flowchart of this process is shown in FIG. 11 (this will be described below).

In the next step S25, the coordinates of the end points of the palisade vessels saved in the palisade vessel extraction process are acquired. In step S26, a boundary line generation process of connecting a sequence of end point coordinate points together with a segment is executed to generate (acquire) boundary line information. FIG. 10A shows the boundary line information generated by the process, more specifically, the palisade vessel end point boundary.

Moreover, in step S27, a boundary line image is generated which contains the boundary line information (palisade vessel end point boundary) acquired by the boundary line image generation process, and a dark portion and the epithelium boundary 34, which have already been acquired. This image is shown in FIG. 10B.

In the next step S28, the Barrett esophagus determination process is executed, that is, whether or not the target site is the Barrett esophagus or the Barrett mucosa, on the basis of already acquired information on the positional relationship with the epithelium boundary 34 between the squamous epithelium and the columnar epithelium. This process will be described below in detail with reference to FIG. 13.

As described above, determinations are made for the Barrett esophagus or the Barrett mucosa and displayed to finish the process.

Now, the palisade vessel extraction process in step S24 in FIG. 9 will be described with reference to FIG. 11.

When the palisade vessel extraction process is started, in the first step S31, unprocessed segments are acquired from the thinned image. An example of the corresponding image is shown in FIG. 12A.

In the next step S32, the number of pixels in each segment is calculated to be a segment length L. In the next step S33, the calculated segment length L is compared with a predetermined threshold thre1 to determine whether the former is greater or smaller than the latter. In the determination process, if L>ther1, the process proceeds to the next step S34. If L≦ther1, that segment is determined not to be the palisade vessel. The process then shifts to step S41. In the present embodiment, for example, ther1=50.

In step S34, the number C of branching and intersecting points in each segment and the number B of bending points in each segment are calculated. In step S35, the numbers are compared with a predetermined threshold E. When C≦Cth and B<ϵ, the process proceeds to the next step S36. When C>Cth or B≧ϵ, that segment is determined not to be the extraction target palisade vessel but a dendritic vessel. The process then shifts to step S41. In the present embodiment, Cth=0 and ϵ=3.

In step S36, one of the two end points of the segment which is closer to the already acquired image dark portion is acquired. In step S37, a vector v connecting the end point and the center of the dark portion together is calculated.

In the next step S38, the angle θ between the vector v and a straight line connecting the segment start point and the segment end point together is calculated. In the next step S39, the apparatus determines whether the calculated angle θ is greater or smaller than a threshold thre2.

If the determination in step S39 indicates that θ<thre2 (for example, θ1 in FIG. 12B), the process proceeds to step S40. In contrast, if θ≧thre2 (for example, θ2 in FIG. 12B), that segment is determined not to be the palisade vessel. The process then shifts to step S41. In the present embodiment, thre2=45°.

In step S40, those of the segments extract in step S31 which meet the determination conditions in step S39 are determined to be the palisade vessels. The information (the segment length L, the branching and intersecting point count C of the segment, the bending point count B, the coordinate point sequence of the segment, the coordinates of the end point, and the angle θ) on those segments is saved as palisade vessel information. This enables the palisade vessels to be extracted as shown in FIG. 12C.

As described above, the process from step S31 to step S35 constitutes a processing section in which the EG junction detection block 45 determines the segment to be the palisade vessel taking into account the branching point count, intersecting point count, and bending point count of the segment obtained by executing the thinning process on the frame image data. The process from step S36 to step S39 constitutes a processing section in which the EG junction detection block 45 determines the segment to be the palisade vessel taking into account the angle between the segment connecting the opposite ends of the segment obtained by executing the thinning process on the frame image data and the vector connecting the dark portion center of the image dark portion of the frame image to one of the opposite ends which is closer to the image dark portion.

In step S41, the presence or absence of any unprocessed segment is determined. If there remains any unprocessed segment, the process loops back to step S31. If all the segments have been processed, the process is ended.

In steps S36 to S39, a matched filter may be used to extract only vessels extending toward the dark portion.

Now, the Barrett mucosa determination process in step S28 in FIG. 9 will be described with reference to FIG. 13. In step S51, the boundary line image generated by the above boundary line image generation process is acquired. This corresponds to FIG. 10B.

In the next step S52, the entire image is divided by a predetermined number of, that is, N radial lines. FIG. 10C shows that the image is divided with N set at, for example, 8.

In the next step S53, a variable i indicating the ith radial line [i] is set at an initial value of 1.

In the next step S54, a point P1 at which the ith radial line [i] crosses the epithelium boundary 34 and a point P2 at which the ith radial line [i] crosses the boundary formed are calculated. FIG. 10C shows an image showing the calculated points P1 and P2.

In the next step S55, the distance Q[i] between the points P1 and P2 is calculated.

In the next step S56, the apparatus determines whether all the radial lines have been processed. That is, the apparatus determines whether or not i is equal to the radial line count N. If i has not reached N, then in step S57, i is incremented by one. The process then returns to step S54 to execute a process similar to that described above. If all the radial lines have been processed, the process proceeds to step S58.

Once the distance Q[i] between the points P1 and P2 is calculated for all the radial lines, that is, the N radial lines, the N distances Q[i] are used to calculate a variance σ in step S58.

In the next step S59, the apparatus determines whether the variance σ is greater or smaller than a predetermined threshold thre3. If σ>thre3, the process proceeds to step S60. In contrast, if σ≦thre3, the image is determined not to show the Barrett mucosa. The process is then ended. In the present embodiment, thre3=5.

In step S60, if the image acquired in step S51 meets the determination condition in step S59, the image is determined to show the Barrett mucosa. The determination is, for example, displayed, announced, or saved, and the process is then ended.

Whether or not the target site is the Barrett mucosa (Barrett epithelium) can be accurately determined in accordance with the process shown in FIGS. 9 to 13.

That is, the process detects each of the EG junction 35 and the epithelium boundary 34, and on the basis of the detection results, determines whether or not the target site is the Barrett mucosa. This enables appropriate and accurate determinations.

The process shown in FIG. 13 may be partly changed as described below so that substantially quantitative determinations can be made for the Barrett mucosa and the Barrett esophagus by calculating (estimating) the radius (diameter) of the esophagus 33 in the image and using a known statistical value for the radius.

A process of calculating the distance (defined as R[i] for simplification) between the dark portion center O and the point P1 (or between the dark portion center O and the point P2) is executed between, for example, steps S55 and S56 in FIG. 13.

The determination process in step S56 is executed, and not only the distance Q[i] between the points P1 and P2 but also the distance R[i] is calculated for all the radial lines [i]. Subsequently, instead of calculating the variance σ of the distances Q[i] in step S58 in FIG. 13, the average value Rav of the distances R[i] is calculated. The average value Rave is determined to be an evaluation value (estimation value) for the radius near the epithelium boundary 34 in the esophagus 33.

A statistical radius value Rs (cm) for the esophagus 33 of a normal adult or a person having a body type similar to that of the patient is pre-stored in the memory or the like. The average value Rav and the radius value Rs are used to evaluate the average value of the distance Q[i] between the points P1 and P2.

The apparatus then determines whether or not the average value of the distances Q[i] is at least 3.0 cm, and if the distance Q[i] is at least 3.0 cm, determines that the target site is the Barrett esophagus.

That is, the presence or absence of the Barrett esophagus is determined taking into account each distance between the dark portion center O as a predetermined point and the epithelium boundary crossing each of the plurality of radial lines radially extending from the dark portion center O or each distance between the EG junction and the dark portion center O.

Further, if the average value of the distances Q[i] is, for example, about 1.5 cm, this may be determined to indicate the substantial progress of the Barrett mucosa. Further, if the average value of the distances Q[i] is, for example, about 0.5 cm, this may be determined to be an initial symptom of the Barrett mucosa.

Thus, the present variation makes it possible to substantially quantitatively determine whether or not the target site is the Barrett esophagus, and in the case of the Barrett mucosa, to quantitatively determine the progress of symptoms. Then, early treatments can be achieved by for example, displaying the determination.

Alternatively, instead of the Barrett mucosa determination process shown in FIG. 9, a process such as a variation shown in the flowchart in FIG. 14 may be executed.

The present variation differs from the process in the above flowchart in that as shown in FIG. 14, an epithelium boundary palisade vessel image generation process in step S61 is executed in place of the vessel end point extraction process in step S25 in FIG. 9, the boundary line generation process in step S26 in FIG. 9, and the boundary line image generation process in step S27 in FIG. 9. An epithelium boundary palisade vessel image generated by this process is used to execute a Barrett mucosa determination process in step S62.

In the epithelium boundary palisade vessel image generation process in step S61, an epithelium boundary palisade vessel image is generated as shown in FIG. 15A, the image containing the palisade vessels acquired by the palisade vessel extraction process, and the dark portion and epithelium boundary already acquired.

In the next step 62, the epithelium boundary palisade vessel image generated in the last step S61 is used to execute the Barrett mucosa determination process. FIG. 16 shows a flowchart of the Barrett mucosa determination process.

As shown in FIG. 16, in the first step S63, an image containing the epithelium boundary 34 already acquired and the palisade vessels is acquired.

In the next step S64, the number J of palisade vessels crossing the epithelium boundary line is initialized, that is, J is set at 0.

In the next step S65, a processing target vessel is acquired from the Q palisade vessels. Moreover, in the next step S66, the apparatus determines whether or not the processing target vessel crosses the epithelium boundary 34. If the processing target vessel crosses the epithelium boundary 34, the process proceeds to the next step S67 to add 1 to the palisade vessel count J. If the processing target vessel does not cross the epithelium boundary 34, the process returns to step S65 to acquire the next processing target vessel. Then, the same process as described above is repeated.

In step S68 subsequent to step S67, the apparatus determines whether or not all the palisade vessels have been processed. If there remains any unprocessed palisade vessel, the process returns to step S65 to repeat the same process as described above. In contrast, if all the palisade vessels have been processed, the process proceeds to the next step S69.

FIG. 15B shows an example of an image for which the number J of palisade vessels crossing the epithelium boundary 34 is calculated. In FIG. 15B, the number Q of palisade vessels is 7, and 6 (=J) of these palisade vessels cross the epithelium boundary 34.

In step S69, the apparatus determines whether J/Q is larger or smaller than a predetermined threshold thre4. If J/Q>thre4, the process proceeds to step S70. In contrast, if J/Q≦thre4, the image is determined not to show the Barrett mucosa. The process is then ended. In the present embodiment, thre4=0.5.

In step S70, if the image acquired in step S63 meets the determination conditions in steps S66 and S69, the image is determined to show the Barrett mucosa. The determination is, for example, displayed on the monitor 4, and the process is then ended.

The present variation makes it possible to determine whether or not the target site is the Barrett mucosa depending on how many palisade vessel end points are present inside the epithelium boundary 34.

As described above, according to the present embodiment, to analyze a large amount of still image data constituting motion picture data on endoscopic images to determine whether or not the target site is the Barrett esophagus, a process is executed which involves detecting an image having the feature of the EG junction 35, a first feature site present around the periphery of a Barrett esophagus determination target site and constituting the stomach-side end points of the palisade vessels. Then, for example, a process of detecting the epithelium boundary 34, a second feature site, is executed on an image following the one detected by the above process, to determine whether or not the target site is the Barrett esophagus. This makes it possible to make an efficient condition determination, that is, to efficiently determine whether or not the target site is the Barrett esophagus. This is effective for reducing the effort required for manual extraction operations.

Further, the EG junction 35, set to be the first feature site the feature of which is detected first as described above, is also utilized to make a determination for the Barrett esophagus condition. This enables the feature detection to be effectively utilized.

A determination can also be made for the Barrett mucosa (Barrett epithelium), a pre-symptom of the Barrett esophagus disease. This enables determinations suitable for early treatments and the like.

It is also possible to avoid the determination of whether or not the target site is the Barrett esophagus, for images that do not require the determination.

The present embodiment has been described in conjunction with motion picture data. However, the present invention may be applied to a plurality of consecutive still image data for one examination (this also applies to the other embodiments and the like).

Second Embodiment

Now, a second embodiment will be described with reference to FIGS. 17 to 26. In the above first embodiment, to determine whether or not the target site is the Barrett esophagus, the process of detecting the EG junction 35 is first executed to detect an image containing the EG junction 35.

The process of detecting the EG junction 35 imposes a heavy load, reducing processing speed. Accordingly, the processing speed or the detection speed needs to be improved. A cardia detection process is possible which can be executed more quickly than the detection of the EG junction 35 and which deals with the biological site expected to be accurately detected.

The present embodiment focuses on this to improve the processing speed and the like.

Figure 17:
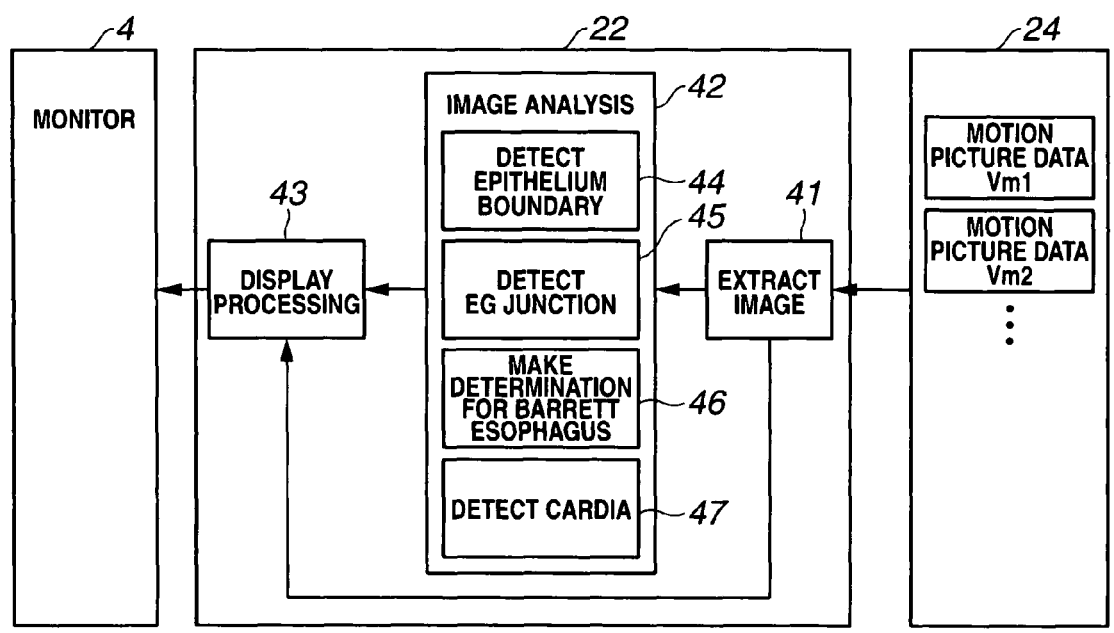
FIG. 17 is a diagram showing the functional configuration of essential sections of an image processing apparatus in accordance with a second embodiment.

The configuration of the hardware of an image processing apparatus in accordance with the present embodiment is similar to that in accordance with the first embodiment; the configuration can be described with reference to FIG. 1. FIG. 17 shows the functional configuration of the CPU 22 based on a processing program in accordance with the present embodiment. In the configuration shown in FIG. 17, a cardia detection block 47 is further provided in the image analysis block 42, included in the configuration shown in FIG. 4. The cardia detection block 47 constitutes a first biological feature detection section that detects the first biological feature.

Figure 18:
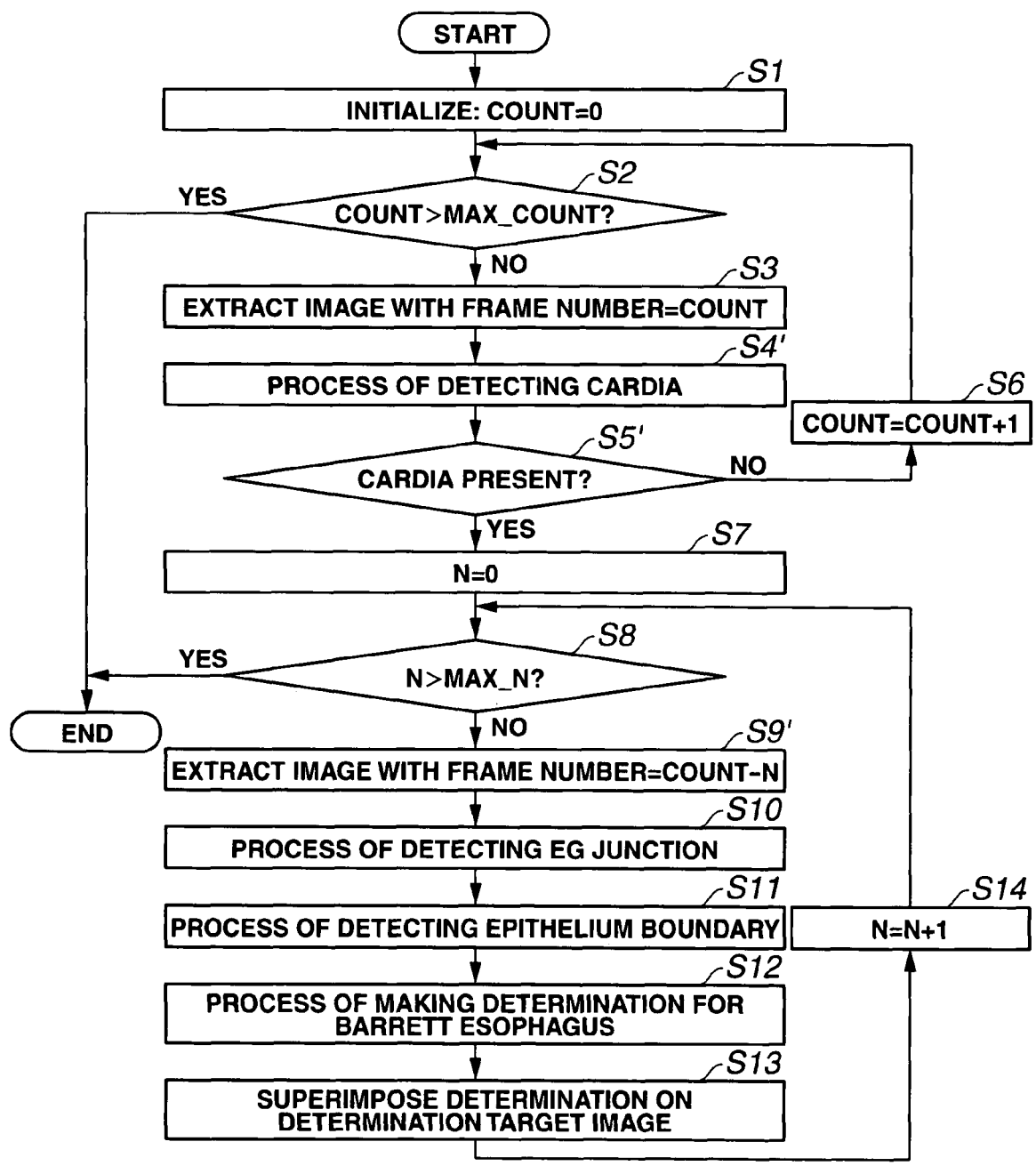
FIG. 18 is a flowchart of a process procedure of determining the Barrett esophagus condition in accordance with the second embodiment.

FIG. 18 shows a flowchart of a process in accordance with the present embodiment. In accordance with the flowchart, a Barrett esophagus determination is made, and for example, the determination is displayed.

The cardia detection block 47, for example, detects a dark portion and thus detects the cardia 37 in the image data on the basis of the shape of the detected dark portion and the degree of rapidity of a change in lightness near the edge of the dark portion. This will be described below in detail with reference to FIG. 19.

The process procedure shown in FIG. 18 is different from that shown in the flowchart in FIG. 8 in that a process of detecting the cardia 37 in step S4' is executed in place of the process of detecting the EG junction 35 in step S4 and that a process of determining the presence of the cardia 37 in step S5' is executed in place of the process of determining the presence of the EG junction 35 in step S5, following step S4.

Further, instead of extracting the image with the frame number=COUNT+N in step S9 of the process procedure in FIG. 8, an image with a frame image=COUNT−N is extracted as shown in step S9' in FIG. 18.

That is, in the first embodiment, the EG junction 35 is located around the periphery of the Barrett esophagus determination target site. Accordingly, an image obtained temporally after the site is detected in the original image is examined to obtain an image showing an area closer to the periphery of the site. This meets image pickup conditions for an image pickup operation performed while inserting the distal end 14 of the endoscope 6.

In contrast, as seen in FIG. 2, the cardia 37 is a site serving as an inlet to the stomach through which the endoscope enters the stomach after having passed through the EG junction 35 and the epithelium boundary 34. Consequently, a frame image is extracted which is located temporally N frames before the image in which the cardia was detected. Images picked up before the above image are sequentially subjected to the determination of whether or not the image shows the Barrett esophagus.

According to the present embodiment, after the detection of the cardia 37, which imposes a lighter processing load than the detection of the EG junction 35, the Barrett esophagus determination process is executed on the basis of the image in which the cardia 37 has been detected. This enables the Barrett esophagus determination to be achieved in a shorter time.

This makes it possible to shift more efficiently to the Barrett esophagus determination process, allowing effects similar to those of the first embodiment to be exerted in a shorter time.

Figure 19:
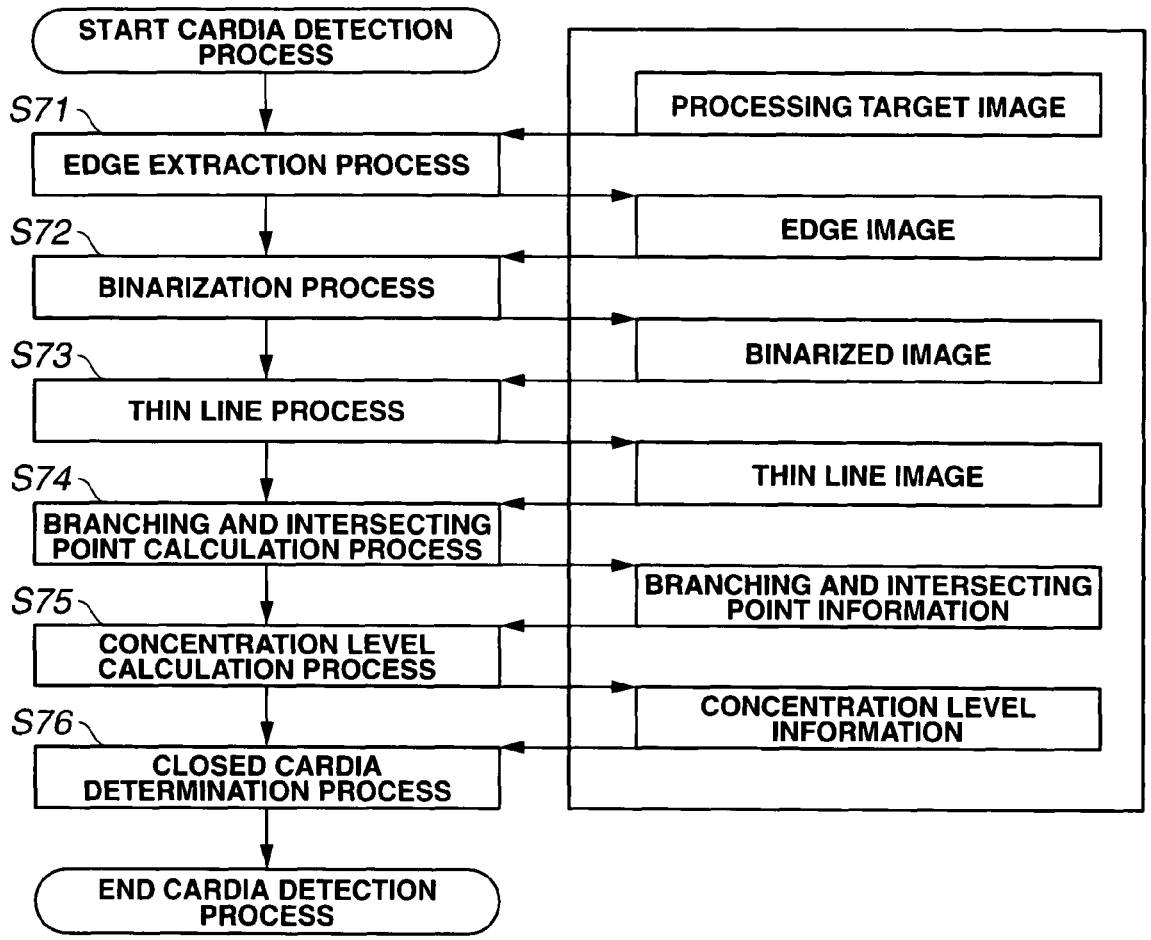
FIG. 19 is a flowchart showing a process procedure of executing a cardia detection process, together with information such as images which is used or generated in the procedure.

Now, the process of detecting the cardia 37 will be described with reference to FIGS. 19 to 22. FIG. 19 shows a process flow in which the closed cardia is detected, as well as data used or generated during the process.

When the process of detecting the cardia 37 is started, an edge detection process is executed on a processing target image as shown in step S71 to generate an edge image.

In the present embodiment, the edge extraction process generates an edge image by applying a bandpass filter to an R color component image.

The edge extraction technique based on the bandpass filter is well known. An edge image may also be generated using a luminance component of the processing target image.

In the next step S72, a binarization is executed on the edge image to generate a binarized image. The binarization in accordance with the present embodiment compares the pixel value of each pixel in the edge image with a specified threshold to determine the value of each pixel in the binarized image to be 0 or 1.

Figure 20A:
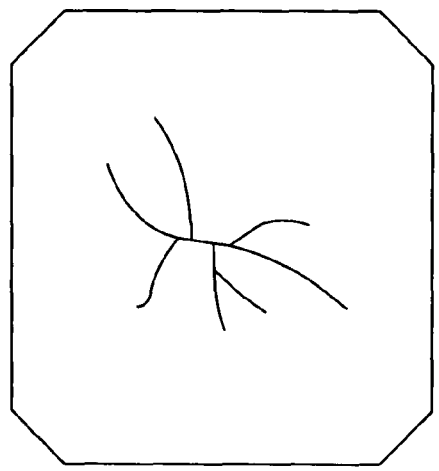
FIG. 20A is a diagram illustrating an operation shown in FIG. 19.

In the next step S73, a well-known thinning technique is applied to the binarized image to execute a thinning process to generate a thinned image. FIG. 20A shows an example of a generated thinned image.

Figure 20B:
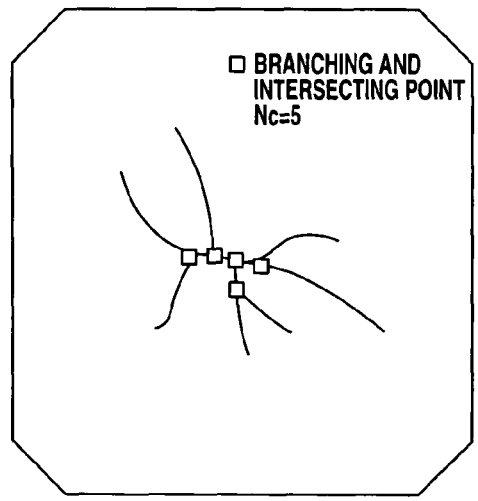
FIG. 20B is a diagram illustrating an operation shown in FIG. 19.

In the next step S74, a branching and intersecting point calculation process of calculating branching and intersecting points for all the thin lines in the thinned image. FIG. 20B shows an example of branching and intersection points calculated for the thinned image in FIG. 20A. FIG. 20B shows that the number Nc of branching and intersecting points is 5.

The coordinates of the branching and intersecting points calculated by the branching and intersecting point calculating process in step S74 are saved as branching and intersecting point information.

In the next step S75, a concentration level calculation process is executed for calculating the concentration level of the branching and intersecting points on the basis of the coordinate values of the branching and intersecting points. Thus, concentration level information is calculated.

Figure 21:
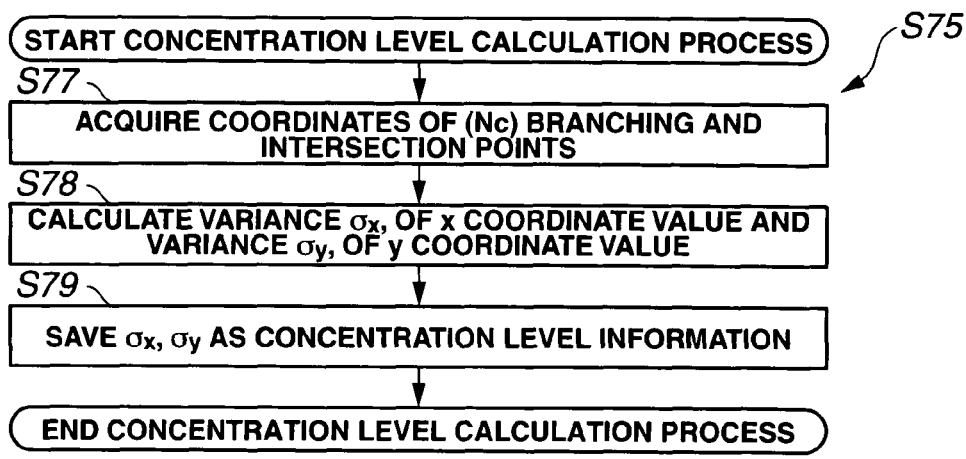
FIG. 21 is a flowchart showing the details of a concentration level calculation process shown in FIG. 19.

The concentration level information will be described below with reference to the flowchart in FIG. 21. In the first step S77, the coordinate values of the Nc branching and intersecting points are acquired. In the next step S78, calculation is made of the variance $\sigma x$ of the x coordinates of the Nc branching and intersecting points and the variance $\sigma y$ of the y coordinates of the Nc branching and intersecting points. In the next step S79, the variances $\sigma x$ and $\sigma y$ are saved as concentration level information. The process is then ended.

In the concentration level calculation process, instead of the variances, standard deviations, coefficients of variations, average values of the distances between each of the Nc branching and intersecting points and the centroid, or the like may be determined to obtain concentration level information.

Referring back to FIG. 19, the concentration level information calculated by the concentration level calculation process in step S75 is used to execute a closed cardia determination process in the next step S76.

Figure 22:
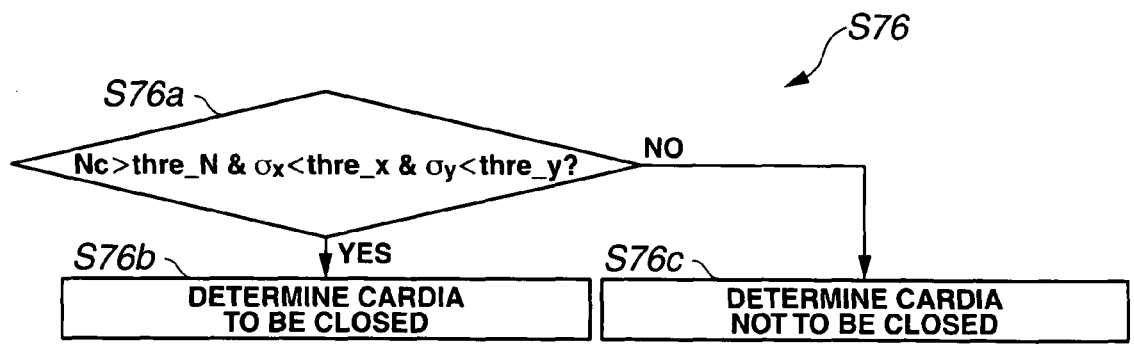
FIG. 22 is a flowchart showing a closed cardia determination process shown in FIG. 19.

As shown in step S76a in FIG. 22, the closed cardia determination process make a determination by comparing the branching and intersecting point count Nc with a predetermined threshold thre_N and compares the concentration level information (σx, σy) with thresholds thre_x and thre_y, respectively.

If the conditions Nc>thre_N, σx<thre_x, and σy<thre_y in step S76a are determined to be met, the target site is determined to be the closed cardia 37 as shown in step S76b. On the other hand, the conditions in step S76a are determined not to be met, that is, Nc≦thre_N, σx≧thre_x, or σy≧thre_y, the target site is determined to not to be the closed cardia 37 as shown in step S76c.

The cardia determination process is thus executed, and the cardia detection process shown in FIG. 19 is then ended.

This enables the cardia 37 to be detected.

As described above, the present embodiment first executes the process of detecting the cardia 37, and if the cardia 37 is detected, makes a determination for the Barrett esophagus, the determination target, for previously picked-up images. This enables the Barrett esophagus determination to be efficiently made even with a large amount of image data.

Further, if the Barrett esophagus determination process is executed as described in the first embodiment, the Barrett mucosa determination can also be made. This determination is effective for early treatments.

Figure 23:
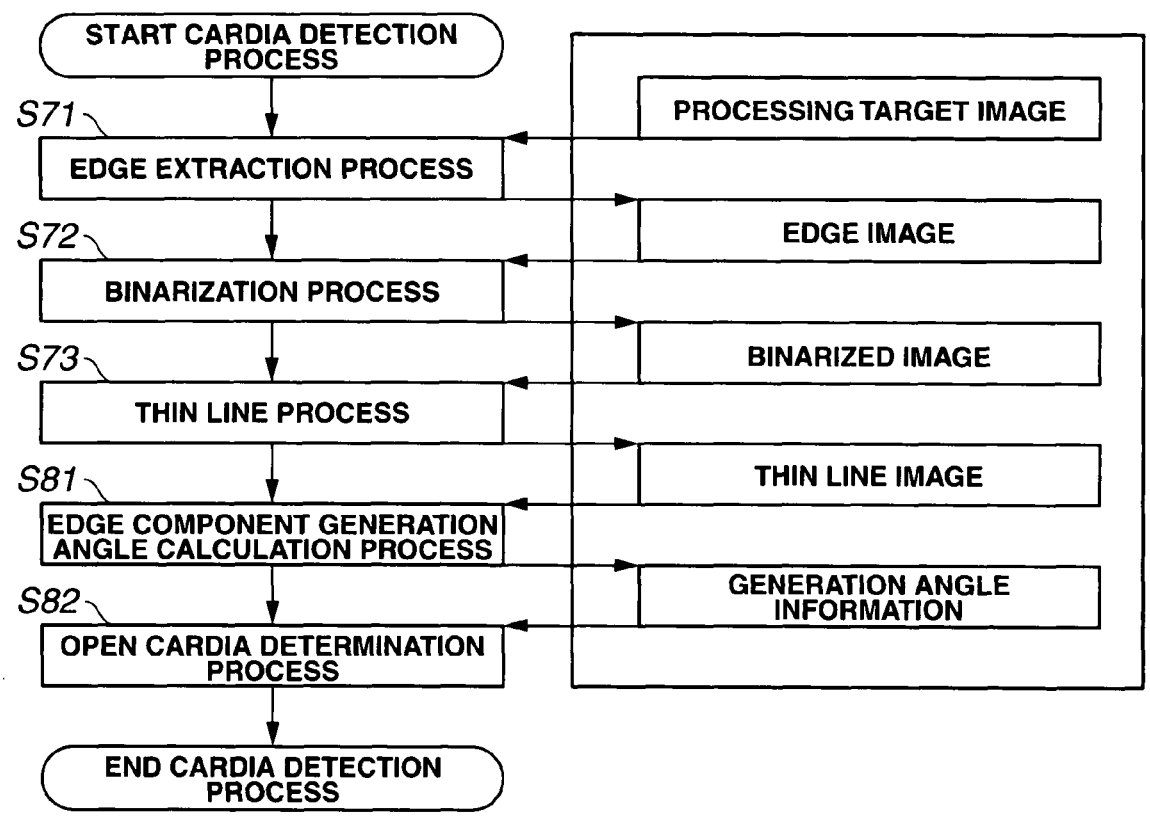
FIG. 23 is a flowchart showing a process procedure of executing a cardia detection process in accordance with a variation, together with information such as images which is used or generated in the procedure.

FIG. 23 shows a flowchart process of cardia detection in accordance with a variation.

The present variation executes an edge component generation angle calculation process in step S81 which is intended to detect the open cardia, in place of the branching and intersecting point calculation process in step S74 and the next concentration level calculation process in step S75, in the process flowchart shown in FIG. 19. The present variation then executes an open cardia determination process of detecting (determining) the open cardia in step S82 on the basis of generation angle information calculated by the edge component generation angle calculation process.

Steps S71 to S73 in the process shown in FIG. 23 are the same as those shown in FIG. 19.

An edge extraction process is executed on a processing target image as shown in step S71 to generate an edge image. The binarization in step S72 is further executed on the edge image to generate a binarized image. The thinning process in step S73 is further executed to generate a thinned image shown in FIG. 24A.

Then, an image containing a dark portion is provided which has been subjected to a dark portion binarization using a dark portion extraction threshold in order to allow the image dark portion to be extracted. The image is superimposed on the thinned image acquired by the thinning process to obtain an image shown in FIG. 24B. The edge component generation angle calculation process in step S81 is then executed on the resulting image to calculate generation angle information on a high edge angle.

An open cardia determination process in step S82 is then executed to determine whether or not the target site is the open cardia.

Figure 25:
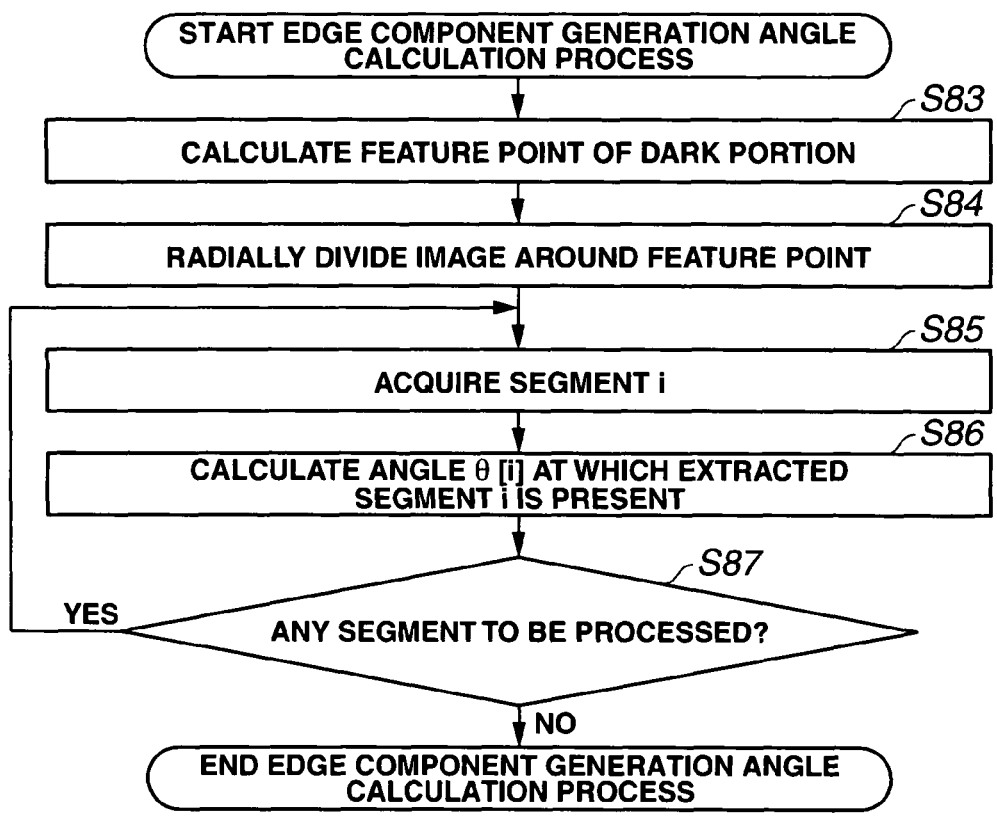
FIG. 25 is a flowchart showing the details of an edge component generation angle calculation process shown in FIG. 23.

FIG. 25 is a flowchart showing the details of the edge component generation angle calculation process in step S81 in FIG. 23.

In the first step S83, one feature point in the dark portion in the image is selected. In the present embodiment, the feature point in the dark portion in the image selected for calculation is, for example, the centroid of the dark-portion.

In the next step S84, the image is divided into a plurality of, for example, M pieces around the calculated feature point such as the centroid or center point in the circumferential direction, using radial lines.

Figure 24A:
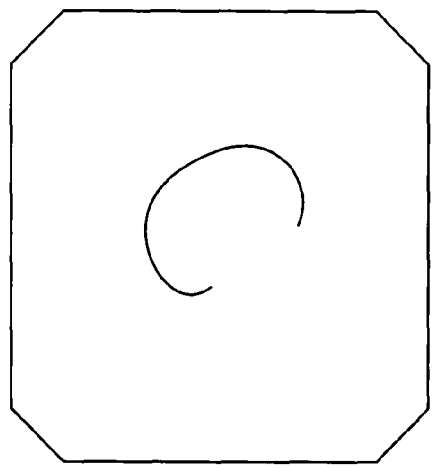
FIG. 24A is a diagram illustrating an operation shown in FIGS. 23 and 25.
Figure 24B:
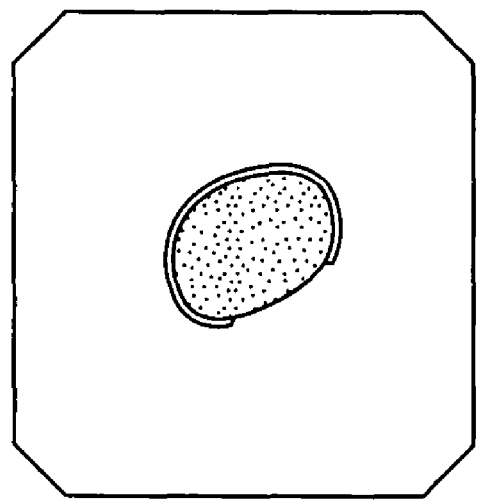
FIG. 24B is a diagram illustrating the operation shown in FIGS. 23 and 25.

In the next step S85, one of the thin lines in the thinned image shown in FIG. 24A described above, that is, a segment i, is extracted (acquired).

In the next step S86, the angle θ[i] through which the extracted segment i is present is calculated. That is, the number Ni of areas in which the segment i is present is counted, and on the basis of the count, the angle θ[i] through which the extracted segment i is present is calculated by θ[i]=Ni×(360/M)°.

Figure 24C:
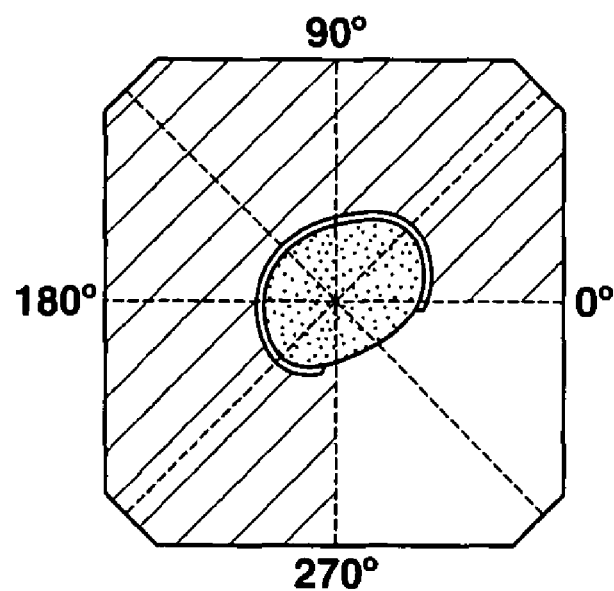
FIG. 24C is a diagram illustrating the operation shown in FIGS. 23 and 25.

An example of the calculation is shown in FIG. 24C. FIG. 24C shows that the number Ni of areas in which the segment i is present is 6, the range of areas being enclosed by a parting line of 0° and a parting line of 270°. That is, in FIG. 24C, the area (shaded part) in which the edge is present spans 270°.

In the next step S87, the apparatus determines whether or not there remains any unprocessed segment. If there remains any unprocessed segment, the process returns to step S85 to acquire the unprocessed segment. Then, a process similar to that described above is executed.

On the other hand, if all the segments have been processed, the edge component generation angle calculation process is ended. Referring back to FIG. 23, angle information on the angle θ[i] generated by the edge component generation angle calculation process in step S81 is used to execute the open cardia determination process in step S82 to determine whether or not the target site is the open cardia.

Figure 26:
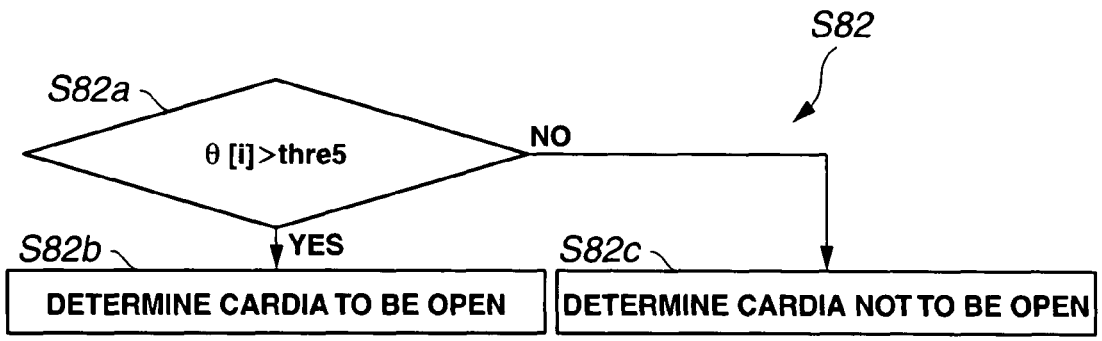
FIG. 26 is a flowchart showing an open cardia determination process shown in FIG. 23.

The open cardia determination process compares the angle θ[i] with a predetermined threshold thre5, for example, as shown in step S82a in FIG. 26. That is, the apparatus determines whether a condition θ[i]>thre5 is met. If the condition θ[i]>thre5 is met, the apparatus determines that the edge corresponds to the open cardia as shown in step S82b. In contrast, if the condition is not met, the apparatus determines that the edge does not correspond to the open cardia. Thus, the process of detecting the cardia is ended.

This enables the open cardia to be detected.

Then, the process of detecting the Barrett esophagus is executed on the image in which the cardia has been detected. This enables an efficient Barrett esophagus determination.

Third Embodiment

Figure 27:
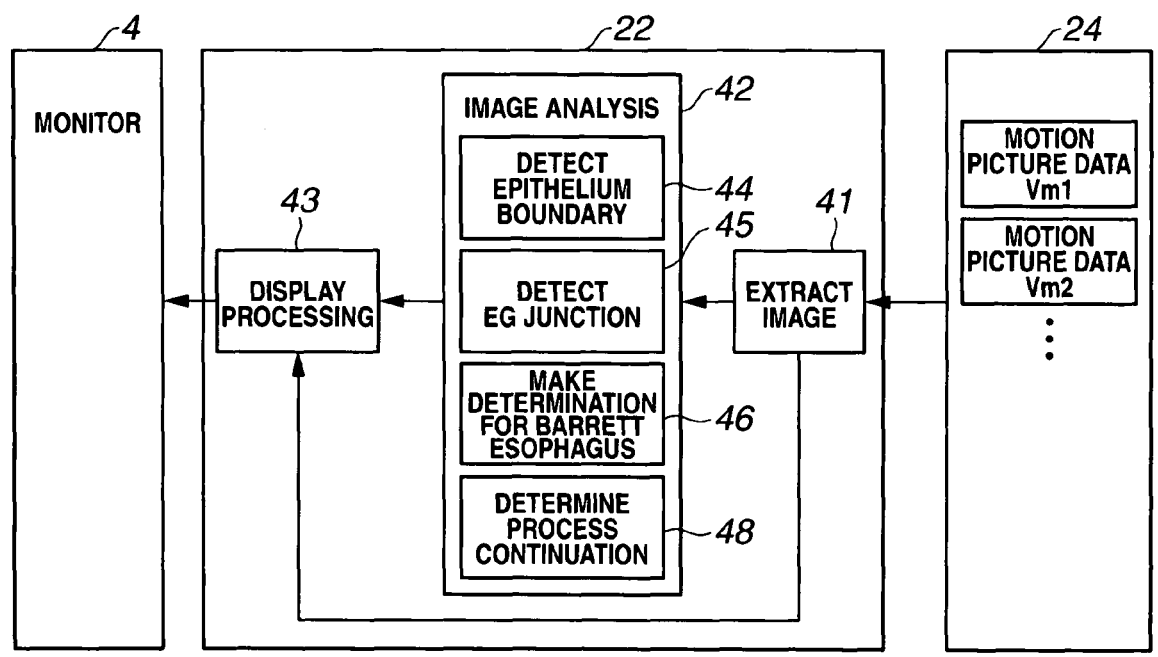
FIG. 27 is a diagram showing the functional configuration of essential sections of an image processing apparatus in accordance with Example 2.

Now, a third embodiment of the present invention will be described with reference to FIGS. 27 to 29. The configuration of the hardware of an image processing apparatus in accordance with the present embodiment is similar to that in accordance with the first embodiment; the configuration can be described with reference to FIG. 1. FIG. 27 shows the functional configuration of essential sections provided by the CPU 22 executing a processing program in accordance with the present embodiment. In the configuration shown in FIG. 27, a processing continuation determination block 48 is further provided in the image analysis block 42, included in the configuration shown in FIG. 4. The processing continuation determination block 48 constitutes a biological feature detection section that detects the first biological feature.

The processing continuation determination block 48 determines whether or not a point sequence for the epithelium boundary line detected by the epithelium boundary detection block 44 is present. The processing continuation determination block 48 further controls the operation of the image analysis block 42 in accordance with the above determination.

Figure 28:
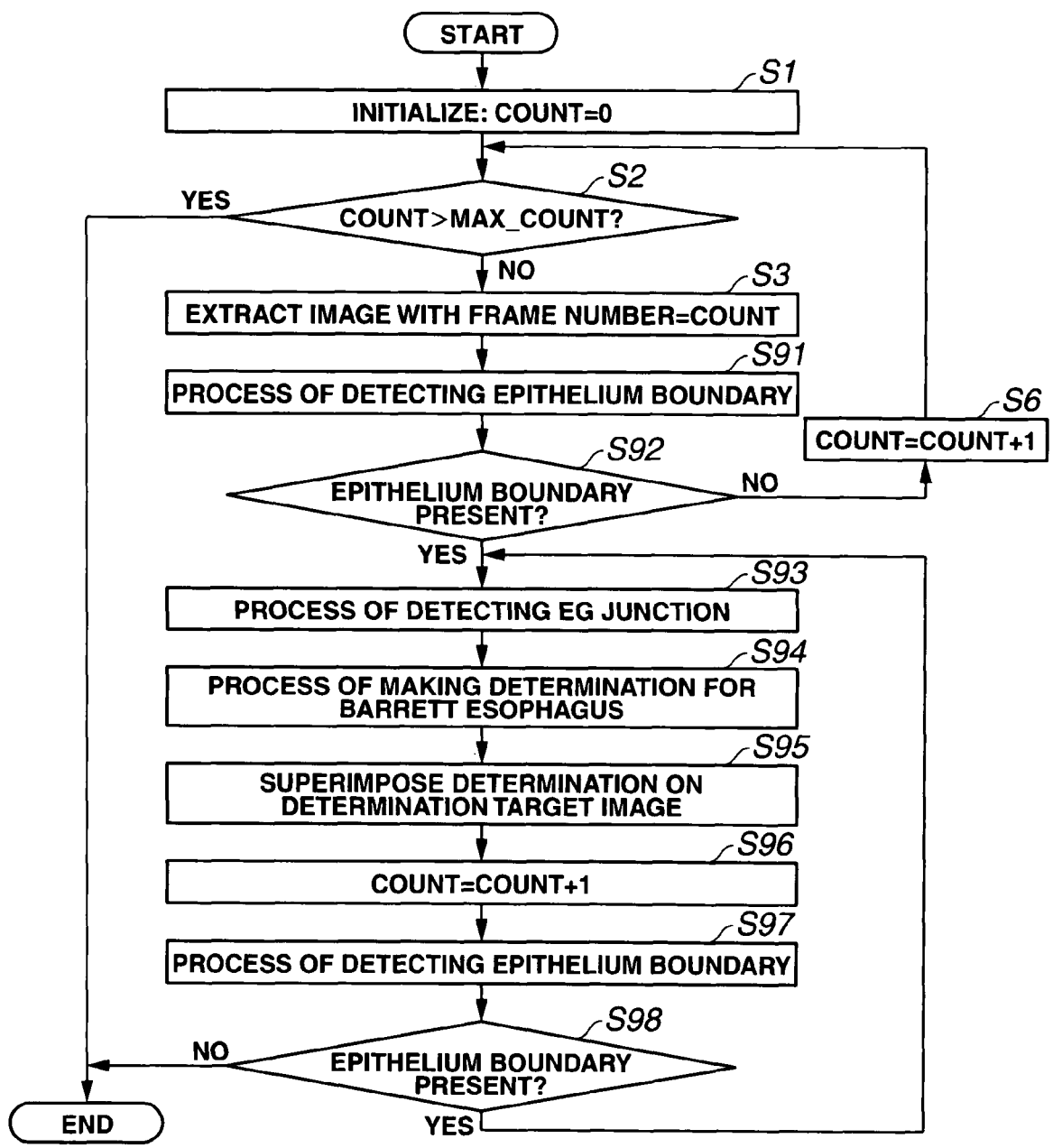
FIG. 28 is a flowchart of a process procedure of determining the Barrett esophagus condition.

FIG. 28 shows a flowchart of a process procedure in accordance with the present embodiment. In accordance with the flowchart, a Barrett esophagus determination is made, and for example, the determination is displayed.

The process method in accordance with the flowchart shown in FIG. 28 corresponds to the process procedure in accordance with the first embodiment shown in FIG. 8 and in which instead of the process of detecting the EG junction 35, an easier process of detecting the epithelium boundary 34 is executed.

First, an image in which the epithelium boundary 34 is detected is retrieved. Once the image in which the epithelium boundary 34 is detected cab be retrieved, the Barrett esophagus determination process is executed.

The process procedure will be described with reference to the flowchart in FIG. 28. The initial steps S1 to S3 are the same as those in the flowchart in FIG. 8 and will thus not be described.

In step S3, an image with the frame number COUNT is extracted, and in the next step S91, a process of detecting the epithelium boundary 34 is executed.

In the next step S92, for the epithelium boundary 34 subjected to the detection process, the processing continuation determination block 48 determines whether or not a point sequence for a line indicating the epithelium boundary 34 is obtained in step S91 to determine whether or not the epithelium boundary 34 is present.

If the apparatus determines in step S92 that the epithelium boundary 34 is not present, the process proceeds to step S6 to increment the frame number variable COUNT by one. The process then returns to step S2 to continue the process from step S2 to step S92, that is, the analysis operation of detecting the epithelium boundary 34.

On the other hand, if the apparatus determines in step S92 that the epithelium boundary 34 is present, the process shifts from the analysis operation of detecting the epithelium boundary 34 to step S93, that is, the analysis operation of making a determination for the Barrett esophagus.

In step S93, the EG junction detection block 45 executes the process of detecting the EG junction 35 starting with the image with that frame number.

After the process of detecting the EG junction 35, in the next step S94, the Barrett esophagus determination block 46 uses the point sequence for the line indicating the EG junction 35 detected in step S93, and the point sequence for the line indicating the epithelium boundary 34 detected in step S91, to determine whether or not the target site in the picked-up image is the Barrett esophagus.

Upon determining that the target site is the Barrett esophagus, the Barrett esophagus determination block 46 passes the determination and the frame number to the display processing block 43 in step S95. The display processing block 43 extracts the image with the specified frame number from the buffer and superimposes the determination on the image data. For example, the display processing block 43 provides such a display as shown in FIG. 7.

In the next step S96, the COUNT is incremented by one. In the next step S97, an image with the next frame number (=COUNT) is newly acquired. The process of detecting the epithelium boundary 34 is then executed on the image.

In the next step S98, the apparatus determines whether or not the epithelium boundary 34 is present on the basis of the preceding detection process.

In step S98, the processing continuation determination block 48 determines whether or nor the point sequence for the line indicating the epithelium boundary 34 is obtained in the preceding step S97, to determine whether or not the epithelium boundary 34 is present.

If the apparatus determines in step S98 that the epithelium boundary 34 is not present, the process loop from step S93 to step S98 is stopped, that is, the analysis operation for the Barrett esophagus determination process is stopped to end the process.

On the other hand, if the epithelium boundary 34 is determined to be present, the process returns to step S93 to execute the process of detecting the EG junction 35 to continue the Barrett esophagus determination process. In this manner, if the presence of the epithelium boundary 34 is detected, the process in the process loop is repeated. The process is ended when the presence of the epithelium boundary 34 fails to be detected again. That is, the biological condition determination is performed on frame images in which the epithelium boundary has been detected.

The present embodiment, operating as described above, first executes the process of detecting the epithelium boundary 34, and when the epithelium boundary 34 is detected through the detection process, shifts to the process of determining the presence or absence of the Barrett esophagus. Then, when the presence of the epithelium boundary 34 fails to be detected again, the process is ended. This enables an efficient Barrett esophagus determination.

That is, the present embodiment provides the processing continuation determination section to perform the following control. Only the image of the periphery of the epithelium boundary 34 is detected, which is required to make a determination for the Barrett esophagus condition. Then, when the epithelium boundary 34 fails to be detected in the image again, the Barrett esophagus determination process is ended. This enables the image required for the Barrett esophagus determination process to be extracted to allow the Barrett esophagus determination process to be executed, without the need for much time and effort.

That is, the present embodiment allows the Barrett esophagus determination process to be executed in a shorter time and with less effort than the first embodiment.

In the present embodiment, after the epithelium boundary 34 is detected in a frame image, the next epithelium boundary detection target image is a frame image temporally and consecutively following the above frame image. However, the next detection target image to be acquired may be a temporally preceding frame image depending on, for example, the temporal direction in which images are picked up.

Alternatively, the next frame image to be acquired may be specified by defining the intervals at which consecutive frame images are acquired as N (N is a natural number of 1, 2, 3, . . . ) and incrementing COUNT to COUNT+N in step S97.

Now, a variation of the present embodiment will be described. When the apparatus determines whether or not each image shows the Barrett esophagus, the picked-up image may be erroneously determined not to show the Barrett esophagus under the effect of noise, halation, a temporal variation in light quantity, shading, or the like contained in the image data, though the image actually shows the Barrett esophagus.

Figure 29:
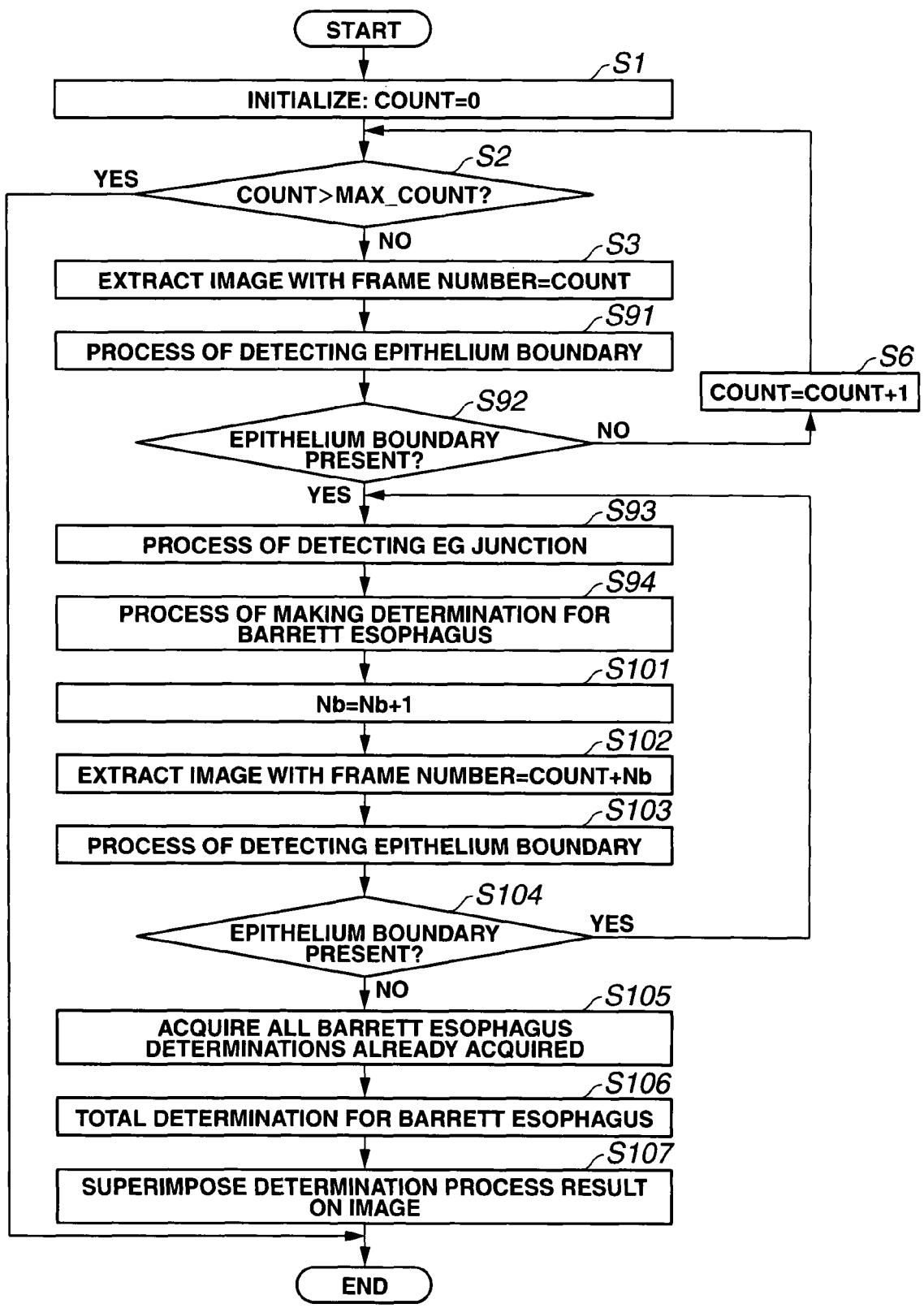
FIG. 29 is a flowchart of a process procedure of determining the Barrett esophagus condition in accordance with a variation.

Thus, the present variation solves this problem by the process procedure shown in FIG. 29. Steps S1 to S94 in the process procedure shown in the flowchart in FIG. 29 are the same as those in the process procedure shown in FIG. 28 (however, in FIG. 29, a frame number variable Nb is additionally used and thus initialized to zero in step S1).

In FIG. 28, the determination in step S94 is displayed in step S95. However, in the present variation, after the determination process in step S94, the frame number is changed to the next one. Then, the process of detecting the epithelium boundary 34, the process of detecting the EG junction 35, and the like are executed to allow the Barrett esophagus determination process to be executed.

Then, when the current image is found not to contain the epithelium boundary 34, the process totally determines whether or not the target site is the Barrett esophagus on the basis of all the determinations of whether or not the target site is the Barrett esophagus. The total determination is then displayed.

The process procedure will be described below with reference to FIG. 29. Steps S1 to S94 in the process procedure are the same as those shown in FIG. 28 (however, as described above, in step S1, another frame number variable Nb is initialized to zero) and will not be described below.

In step S94, the apparatus determines whether or not the target site is the Barrett esophagus on the basis of the position at which the epithelium boundary 34 is present and which has been determined in step S92 as well as the result of the process of detecting the EG junction 35 in step S93. The Barrett esophagus determination is temporalily stored, and in the next step S101, the variable of the frame number Nb is incremented by one. In the next step S102, an image with the frame number Nb incremented by one, that is, the frame number COUNT+Nb, is extracted.

In the next step S103, the process of detecting the epithelium boundary 34 is executed. After the detection process, the apparatus determines in the next step S104 whether or not the epithelium boundary 34 is present. If the epithelium boundary 34 is present, the process returns to step S93 to execute the process of detecting the EG junction 35 to execute, for example, the process of determining whether or not the target site is the Barrett esophagus as described above.

On the other hand, upon determining that the epithelium boundary 34 is not present, the process shifts to step S105 to acquire all the determinations for the Barrett esophagus made during the process from step S93 to step S104.

In the next step S106, the process totally determines whether or not the target site is the Barrett esophagus on the basis of all the Barrett esophagus determinations. In the next step S107, the total determination is then displayed so as to be superimposed on the image. The process is then ended.

The Barrett esophagus determination block 46 totally determines in step S106 whether or not the target site is the Barrett esophagus as follows.

For example, the Barrett esophagus determination block 46 calculates the ratio Na/Nb of the number Na of images determined to show the Barrett esophagus to the number Nb of images subjected to the determination of whether or not the target site is the Barrett esophagus. If the ratio Na/Nb is greater than 0.8, the Barrett esophagus determination block 46 determines that the image pickup target is the Barrett esophagus. In step S107, the Barrett esophagus determination block 46 superimposes information "Suspected Barrett esophagus" on all the Nb images used for the Barrett esophagus determination.

The present variation, performing the process operation as described above, exerts effects similar to those of the third embodiment. The present variation further makes a total determination using information on the determination of whether or not each of a plurality of images shows the Barrett esophagus. This makes it possible to very reliably determine whether or not the target site is the Barrett esophagus.

In the above description, image processing is executed on endoscopic images picked up by inserting the endoscope 6 with the elongate insertion portion into the living body. However, the contents of the process in each of the above embodiments and variations are also applicable to endoscopic images picked up by a capsule endoscope that is swallowed through the mouth to pick up in vivo images.

The capsule endoscope is normally an in vivo image pickup apparatus that consecutively picks up still images at regular time intervals. In this case, after swallowed through the mouth, the capsule endoscope moves through the esophagus 33, the stomach, the small intestine, and the large bowel, while picking up images thereof, while without moving backward. Each of the above embodiments and variations is also applicable to this case.

Further, the present invention includes embodiments each obtained by, for example, partly combining the above embodiments and the like together.

As described above, according to the above embodiments and variations, to determine the condition of the living body, it is possible to detect the first biological feature and then the second biological feature. This enables an efficient determination for the condition of interest such as the Barrett esophagus from a large amount of image data. That is, if the first biological feature fails to be detected, the detection of the second biological feature is omitted. This enables an efficient image analysis process. Therefore, even with a large amount of image data, an efficient determination can be made for the condition of interest such as the Barrett esophagus.

Now, a luminal image processing apparatus in accordance with an embodiment will be described with reference to the drawings.

Fourth Embodiment

Figure 30A:
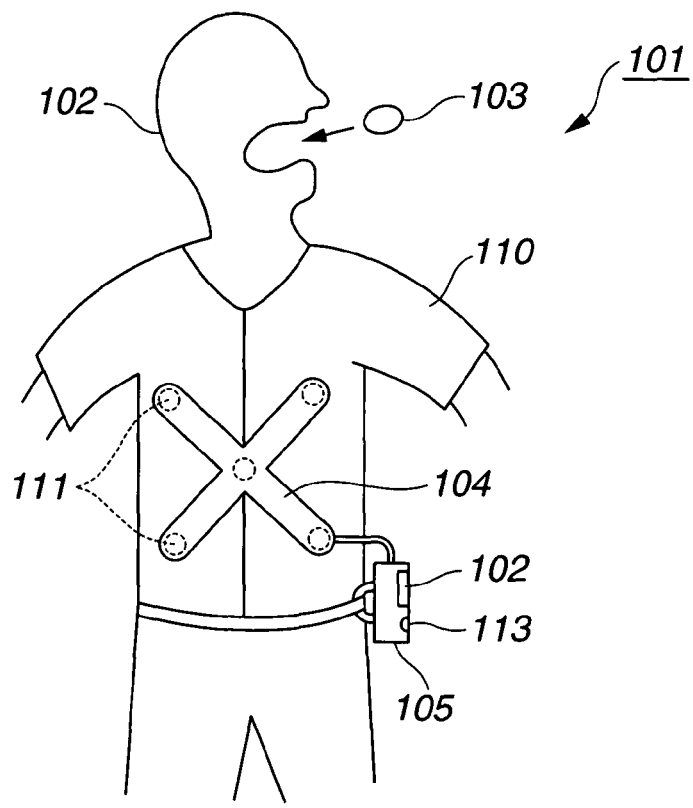
FIG. 30A is a block diagram showing the general configuration of a capsule endoscope apparatus in accordance with a fourth embodiment.
Figure 30B:
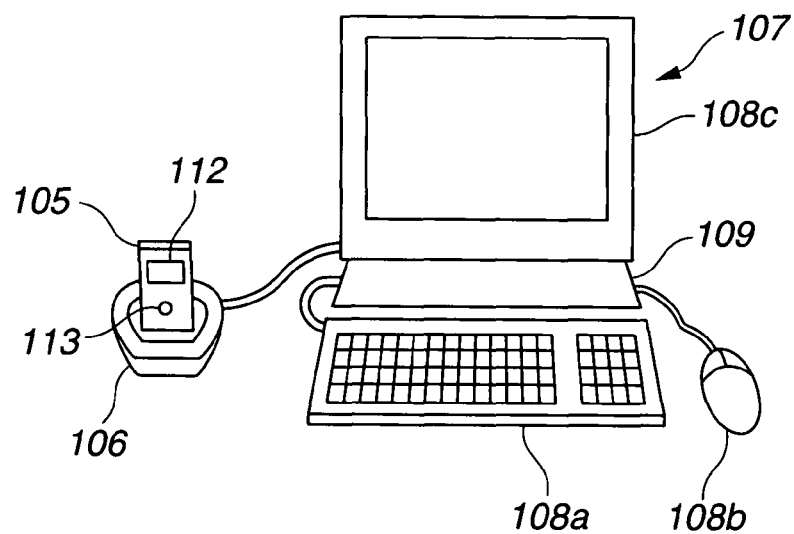
FIG. 30B is a block diagram showing the general configuration of a terminal apparatus serving as a luminal image processing apparatus in accordance with the fourth embodiment.

First, with reference to the drawings, description will be given of a luminal image processing apparatus utilizing a capsule endoscope apparatus as well as a method for the luminal image processing in accordance with a fourth embodiment. First, with reference to FIGS. 30A, 30B and 31, description will be given of the luminal image processing apparatus utilizing the capsule endoscope apparatus in accordance with the fourth embodiment. FIGS. 30A and 30B are block diagrams showing the general configuration of a capsule endoscope apparatus 101 and a terminal apparatus 107 serving as a luminal image processing apparatus in accordance with the present embodiment.

As shown in FIG. 30A, the capsule endoscope apparatus 101 using an image processing method in accordance with the present embodiment comprises a capsule endoscope 103, an antenna unit 104, and an external device 105. Although described below in detail, the capsule endoscope 103 is shaped so as to be swallowed through the mouth of a patient 102 that is a subject to advance through the esophagus and the gastrointestinal tract. The capsule endoscope 103 internally has an image pickup function of picking up images of the esophagus and the gastrointestinal tract to generate picked-up image information and a transmission function of transmitting the picked-up image information to the exterior of the living body. The antenna unit 104 has a plurality of reception antennas 111 installed on the body surface of the patient 102 to receive the picked-up image information transmitted by the capsule endoscope 103. The external device 105 is externally shaped like a box and has functions of, for example, executing various processes on the picked-up image information received by the antenna unit 104, recording the picked-up image information, and displaying the picked-up images on the basis of the picked-up image information. An armor of the external device 105 has a liquid crystal monitor 112 and an operation portion 113 on a surface thereof, the liquid crystal monitor 112 displaying the picked-up images, the operation portion 113 being used to give instructions on the operation of the various functions. Further, the external device 105 has an alarm display LED for the amount of power remaining in a battery serving as a driving power supply, and a power supply switch serving as the operation switch 113.

The external device 105 is installed on the body of the patient 102, and as shown in FIG. 30B, is installed on a cradle 106 to connect to the terminal apparatus 107. For example, a personal computer is used as the terminal apparatus 107, which is a luminal image processing apparatus and serves as a cardia detection apparatus. The terminal apparatus 107 comprises a terminal main body 109 having functions of processing and storing various data, a keyboard 108a and a mouse 108b which are used to input various operations, and a display 108c that displays the results of processing results. The basic function of the terminal apparatus 107 is to load, via the cradle 106, the picked-up image information recorded in the external device 105, and to write and record the picked-up image information in a rewritable memory contained in the terminal main body 109 or a portable memory such as a rewritable semiconductor memory that can be freely installed in and removed from the terminal main body 109, and to execute image processing such that the recorded picked-up image information is displayed on the display 108c. Moreover, the terminal apparatus 107 executes a cardia detection process using an image processing method in accordance with an embodiment described below. The picked-up image information stored in the external device 105 may be loaded into the terminal apparatus 107 via a USB cable or the like instead of the cradle 106. The cradle 106 and the like constitute an image input section via which images picked up by the capsule endoscope 3 are inputted.

Figure 31:
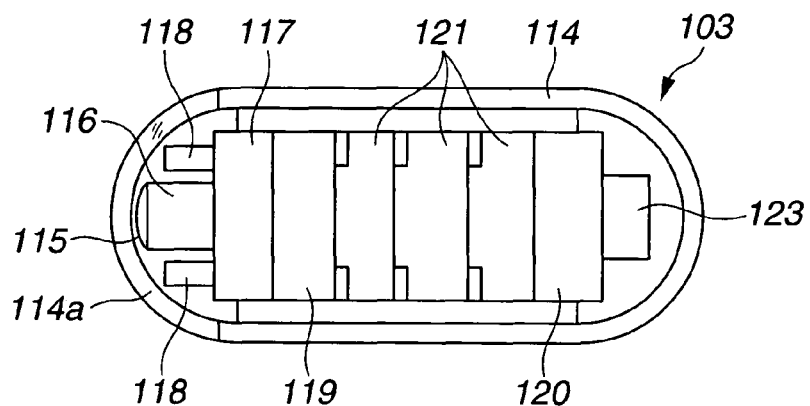
FIG. 31 is a diagram illustrating the general structure of the capsule endoscope in accordance with the fourth embodiment.

Now, the external shape and internal structure of the capsule endoscope 103 will be described with reference to FIG. 31. The capsule endoscope 103 is shaped like a capsule comprising an armor member 114 having a U-shaped cross section and a hemispherical cover member 114a installed at a distal open end of the armor member 114 in a water tight manner via an adhesive and formed of a transparent member.

In an internal hollow portion of the capsule shape, comprising the armor member 114 and the cover member 114a and inside a central portion of the arc of the hemisphere of the cover member 114a, an objective lens 115 is housed in a lens frame 116 to capture an image of an observation target which is incident via the cover member 114a. A charge coupled device (hereinafter referred to as a CCD) 117 that is an image pickup device is located at an image formation position of the objective lens 115. Four white LEDs 118 are arranged on the same plane around the lens frame 116, in which the objective lens 115 is housed, to emit and radiate illumination light (only two LEDs are shown in the figure). The following are arranged in the hollow portion of the armor member 114 and behind the CCD 117: a processing circuit 119 that drivingly controls the CCD 117 to executes a process of generating a photoelectrically converted image pickup signal, an image pickup process of executing predetermined signal processing on the image pickup signal to generate a picked-up image signal, and a LED driving process of controlling an operation of illuminating and non-illuminating the LEDs 118, a communication processing circuit 120 that converts the picked-up image signal generated by the image pickup process executed by the processing circuit 119 into a radio signal to transmit the radio signal, a transmission antenna 123 that transmits the radio signal from the communication processing circuit 120 to the exterior, and a plurality of button cells 121 that supply driving power to the processing circuit 119 and the communication processing circuit 120. The CCD 117, LED 118, processing circuit 119, communication processing circuit 120, and transmission antenna 123 are arranged on circuit boards (not shown) that are connected together via flexible boards.

The capsule endoscope 103 picks up in vivo images at predetermined time intervals while moving through the body of the patient 102 and transmits the images to the external device 105. The external device 105 records each of the received endoscopic images in a built-in storage device. The endoscopic image recorded in the external device 105 is transferred via the cradle 106 to the terminal apparatus 107, where the image is stored in a storage device (not shown). The terminal apparatus 107 executes a cardia detection process on the basis of the transferred and stored endoscopic image. The cardia detection process is executed by image processing software, that is, a program, which executes image processing on image data on the endoscopic image. The image processing software is executed by a processing device such as the CPU in the terminal apparatus 107.

Image processing described below is implemented by software and may be executed by any of the capsule endoscope 103, the external device 105, and the terminal apparatus 107. The description below takes an example in which the image processing is executed by the terminal apparatus 107, which uses the personal computer. In the description of the contents of the image processing, the size of one frame image corresponds to 3 planes of ISX×ISY ($1 \leq$ ISX, ISY. For example, ISX=640, ISY=480) for red (R), green (G), and blue (B). Gray scales for the pixels in each plane correspond to 8 bits, that is, have a value of 0 to 255.

Further, the capsule endoscope 103 picks up 15 to 30 images per second (15 fps to 30 fps) to, for example, examine the esophagus. The image pickup function is controlled such that after passing through the esophagus, the capsule endoscope 103 performs a slower image pickup operation with the reduced number of images picked up per second. This is achieved by, for example, providing a timer circuit (not shown) and performing control such that when a timer count provided by the timer circuit indicates that a predetermined time has not passed yet, a faster image pickup operation is performed with the increased number of images picked up per second and such that after the predetermined time passes, a slower image pickup operation is performed with the reduced number of images picked up per second.

Figure 32:
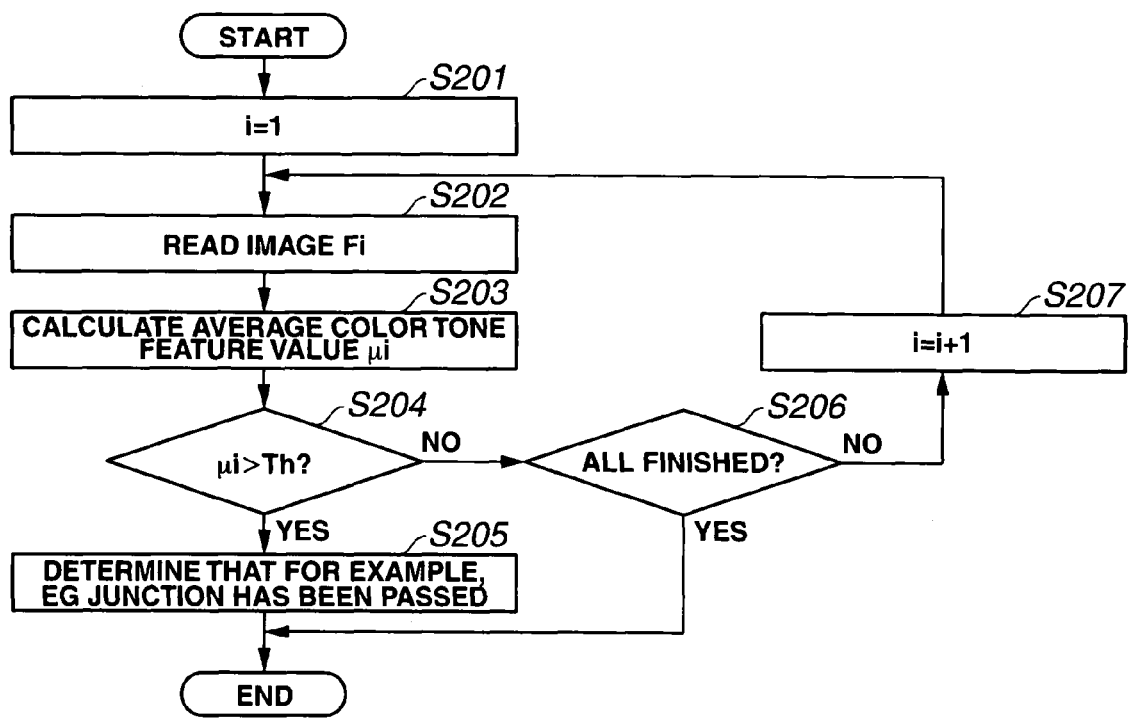
FIG. 32 is a flowchart showing an example of the flow of a process of detecting the cardia by passing through the EG junction, the process being executed by the terminal apparatus.

FIG. 32 is a flowchart showing an example of the flow of a process executed by the terminal apparatus 107 to detect the cardia by passing through the EG junction on the basis of a series of obtained endoscopic images. A series of endoscopic images picked up by the endoscope swallowed through the subject's mouth comprise a plurality of frames. A process shown in FIG. 32 is executed on each of the frames. Image data on each endoscopic image is subjected to a preprocess such as inverse gamma correction or noise removal before the process shown in FIG. 32 is executed.

To process the first frame of the series of images on which the process shown in FIG. 32 is to be executed, first, the frame number i is set at 1 (step S201). Reference character i denotes an integer from 1 to n.

Then, image data on an image Fi with the frame number i is read from the storage device (not shown) in the terminal apparatus 107 (step S202). The image Fi comprises three planes for R, G, and B.

On the basis of the read image data on the image Fi, a predetermined feature value for the endoscopic image, that is, a color tone feature value, in this case, an average color tone feature value μi, is calculated (step S203). The average color tone feature value μi is the average value of the color tone feature values for all the pixels contained in each image. Step S203 constitutes a feature value calculation step or a feature value calculation section which calculates the average color tone feature value, the color tone feature value for each image Fi based on the values for all the pixels.

Then, the apparatus determines whether or not the average color tone feature value μi exceeds a predetermined threshold Th (step S204). If a value R/(R+G+B) described below is used as the color tone feature value, the threshold Th is, for example, 0.5.

Adjusting the value of the threshold Th makes it possible to determine whether the read image Fi shows the vicinity of the EG junction, that is, the boundary of the gastrointestinal tract, the central portion of the EG junction, or the inlet of the stomach. This will be described below with reference to FIG. 33.

If the determination in step S204 is YES, that is, the average color tone feature value μi exceeds the predetermined threshold Th, the capsule endoscope 103 is about to enter the EG junction or is passing through the EG junction. Consequently, the apparatus determines that the read image Fi was picked up at that time (step S205). Steps S204 and S205 constitute a boundary detection section that detects the boundary of the gastrointestinal tract on the basis of the calculated average color tone feature value μi and a determination section that the intraluminal image shows an area extending from the esophagus to the cardia on the basis of the detection result of the EG junction, corresponding to the boundary.

If the determination in step S204 is NO, that is, the average color tone feature value μi does not exceed the predetermined threshold Th, the apparatus determines whether or not the process shown in FIG. 32 has been finished on all of the series of images to be subjected to the process shown in FIG. 32 (step S206). Once the process is finished on all the images, the determination in step S206 is YES and the process is ended. If the determination in step S206 is NO, there remains an unprocessed image and a process of changing i to i+1 is thus executed (step S207). The process from step S202 to step S204 is repeated on the next image.

As described above, in step S205, when the average color tone feature value μi exceeds the predetermined threshold Th, the apparatus determines that the capsule endoscope 103 is passing through the EG junction or is about to enter the EG junction. In other words, the process can also determine that the capsule endoscope 103 will subsequently reach the cardia or the stomach. That is, the process can also determine that the cardia is being detected.

Figure 33:
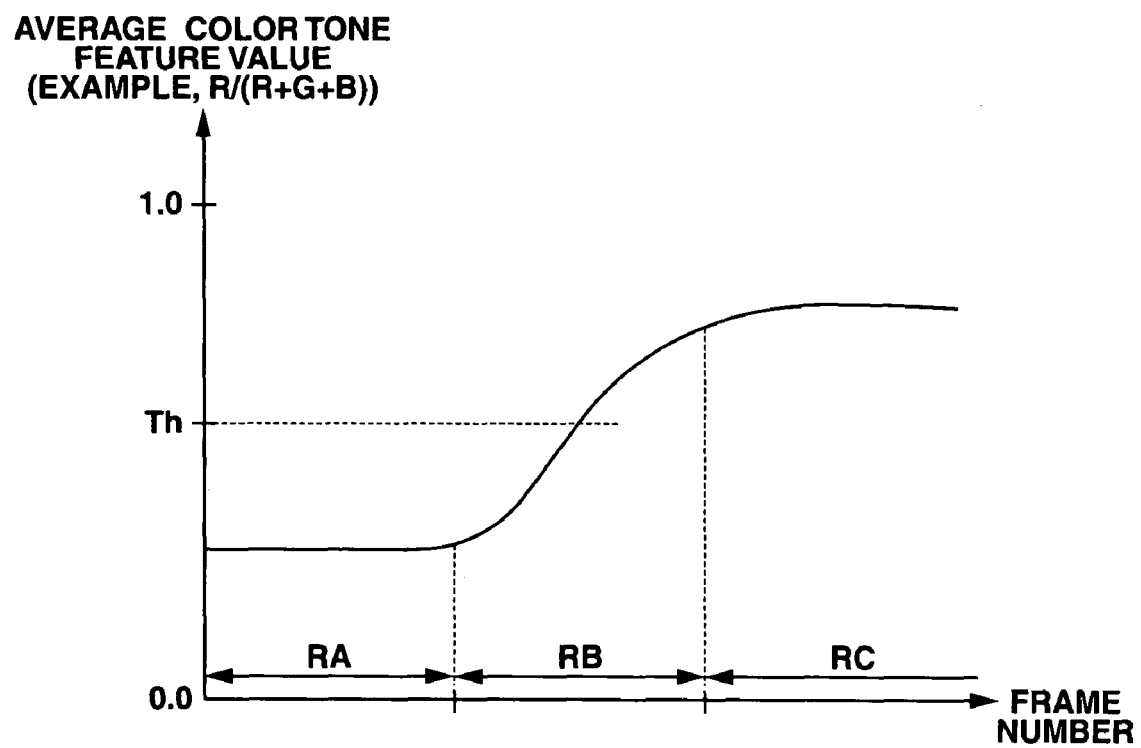
FIG. 33 is a schematic graph illustrating a variation in the color tone in a series of endoscopic images obtained.

Now, description will be given of the color tone of the biological tissue extending from the esophagus to the stomach. FIG. 33 is a schematic graph illustrating a variation in color tone among a series of endoscopic images obtained. In FIG. 33, the axis of abscissa indicates the image numbers (frame numbers), along the time series, of the endoscopic images picked up along a path from the esophagus squamous epithelium through the EG junction to the stomach. The axis of ordinate indicates the color tone feature value for the endoscopic image corresponding to each of the image numbers.

The color tone of images picked up by the capsule endoscope 103 swallowed through the subject's mouth varies as shown in FIG. 33. That is, the color tone varies between the squamous epithelium RA of the esophagus and the stomach portion RC of the columnar epithelium. The color tone varies gradually step by step in the EG junction RB, located between the squamous epithelium RA and the stomach portion RC. In FIG. 33, for example, with a color tone feature value R/(R+G+B) calculated from three pixel values for R, G, and B as described below, the esophagus squamous epithelium RA has a white color tone and thus a small color tone feature value. The stomach portion RC has a red color tone and thus a great color tone feature value. For the EG junction RB, located between the squamous epithelium RA and the stomach portion RC, the color tone feature value varies gradually from the white color tone to the red color tone.

Thus, when such a color tone feature value as shown in step S204 in FIG. 32, which varies gradually, exceeds the predetermined threshold Th (the color tone changes to red), the apparatus determines that the image was picked up when the capsule endoscope 103 was about to enter the EG junction or was passing through the EG junction. In other words, the cardia, the boundary of the gastrointestinal tract, is detected. That is, the cardia is detected on the basis of the difference in color tone between the esophagus mucosa and the stomach mucosa. Specifically, the average value of the color tone feature values or the like is utilized to make a reliable determination for the passage or the like.

Now, description will be given of a specific example of the average color tone feature value μi, described with reference to FIG. 32.

Figure 34:
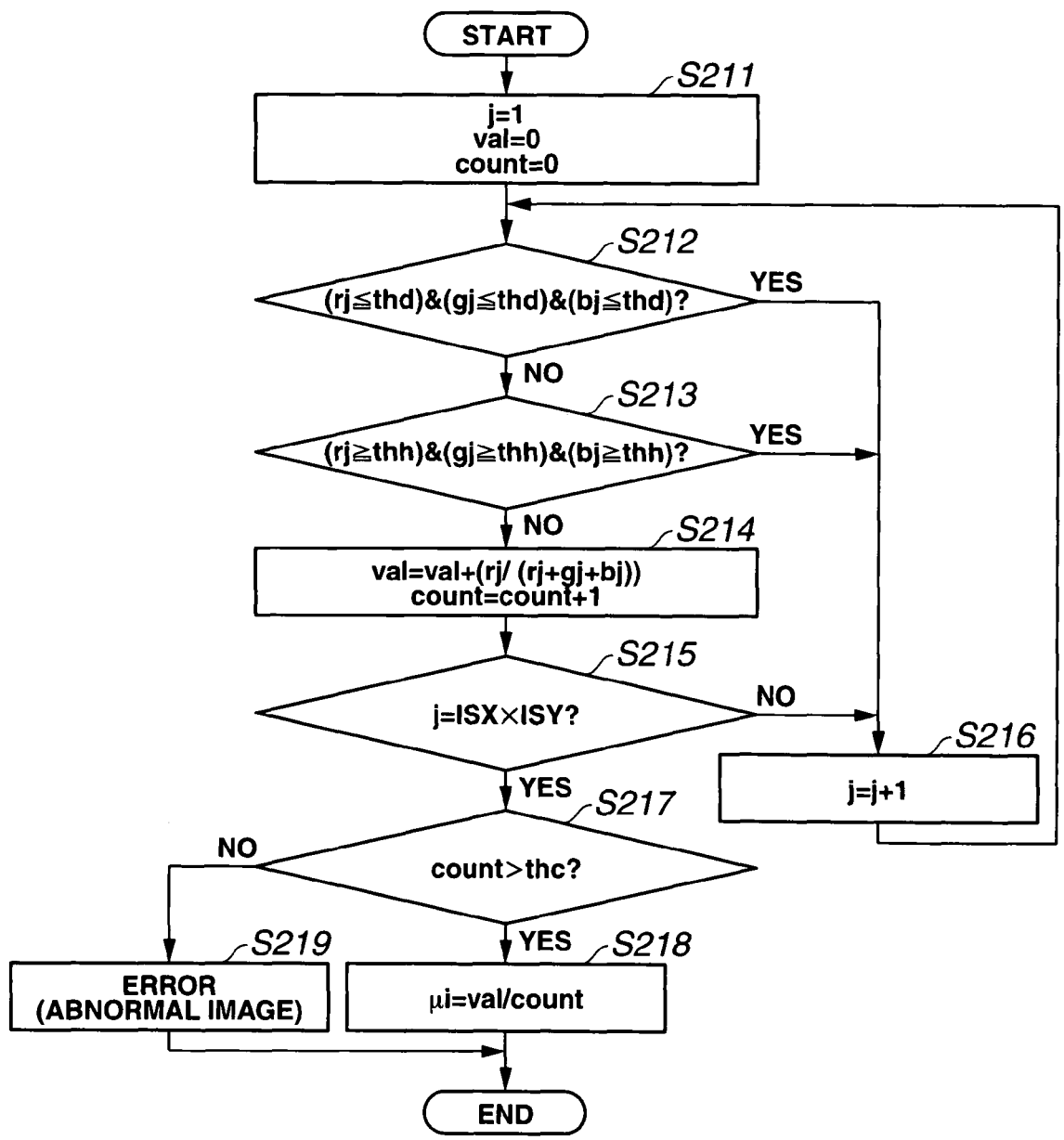
FIG. 34 is a flowchart showing an example of the flow of a process in step S203 shown in FIG. 32.

FIG. 34 is a flowchart showing an example of the flow of the process in step S203 in FIG. 32 which is executed on each frame image and in which R/(R+G+B), calculated from the three pixel values for R, G, and B, is used as the average color tone feature value μi. The process shown in FIG. 34 calculates a chromaticity rj/(rj+gj+bj) on the basis of three pixel values rj, gj, bj for R, G, and B for each of the pixels in one frame to determine the average color tone feature value μi. Reference character j denotes a number identifying a pixel in the image data on each frame.

First, j is set at 1, val is set at 0, and count is set at 0 (step S211). Here, val denotes a variable required to determine the sum of color tone feature values, and count denotes a variable required to determine the number of pixels used to calculate the average color tone feature value μi.

Then, the apparatus determines in step S212 whether or not the jth pixel belongs to a dark portion. Specifically, the values of the jth pixel in each of an R image, a G image, and a B image are defined as rj, gj, and bj. Then, if $rj \leq thd$, $gj \leq thd$, and $bj \leq thd$, that pixel is determined to belong to the dark portion. Here, thd denotes a threshold for each color which is used to determine whether or not the pixel belongs to the dark portion. In the present embodiment, thd is set at 10. If the jth pixel is determined to belong to the dark portion, the process proceeds to step S216. If the jth pixel is determined not to belong to the dark portion, the process proceeds to step S213.

Then, the apparatus determines in step S213 whether or not the jth pixel is extremely bright, that is, the jth pixel belongs to a halation portion. Specifically, if $rj \geq thh$, $gj \geq thh$, and $bj \geq thh$, the pixel is determined to be a halation pixel. Here, thh denotes a threshold for each color which is used to determine whether or not the pixel is a halation pixel. In the present embodiment, Th is set at 200. If the jth pixel is determined to be a halation pixel, the process proceeds to step S216. If the jth pixel is determined not to be a halation pixel, the process proceeds to step S214.

In steps S212 and S213, for the R image, G image, and B image, each of the thresholds thd and thh has the same value for rj, gj, and bj. However, for the biological mucosa, the R image generally tends to be brightest. Accordingly, the threshold may be set higher for rj than for gj and bj. Alternatively, the threshold may vary among rj, gj, and bj.

In step S214, val=val+rj/(rj+gj+bj)) and count=count+1 are calculated. To determine the sum of the color tone feature values, the color tone feature value rj/(rj+gj+bj) is added to a variable val and the variable count is incremented by one.

In step S215, the apparatus determines whether or not the process from step S212 to step S214 has been executed on all the pixels. Specifically, if j<ISX×ISY, then in step S216, 1 is added to the number j identifying the pixel (j=j+1) and steps S212 to S214 are executed on the next pixel. If j=ISX×ISY, that is, the process from step S212 to step S214 has been executed on all the pixels, the apparatus determines whether or not count is greater than a threshold thc (step S217). The threshold thc is a value indicating the number of pixels insufficient for color tone evaluation; a value equal to or greater than the threshold thc means that a sufficient number of pixels are present which are effective for color tone evaluation. In step S217, if the determination is YES, that is, a sufficient number of pixels are present which are effective for color tone evaluation, the average color tone feature value μi is calculated by dividing the color tone feature value sum val by the number of pixels count used to calculate the average color tone feature value μi (step 218). Specifically, μi=val/count. As described above, the average color tone feature value μi is calculated for the pixels in the intraluminal image other than the dark portion pixels and the halation pixels.

If the determination is NO in step S217, that is, a sufficient number of pixels are not present which are effective for color tone evaluation, that frame image is considered to be an error, that is, an abnormal image (step S219). The average color tone feature value μi is determined to be, for example, 0 (zero). In step S204 in FIG. 32, the apparatus determines that the average color tone feature value μi does not exceed the threshold Th.

Now, variations of the present embodiment will be described.

In FIGS. 32 to 34, described above, the apparatus determines whether or not, for example, the capsule endoscope has passed through the EG junction or the cardia, on the basis of each frame image. However, as a first variation, the apparatus may determine that, for example, the capsule endoscope 103 has passed through the EG junction when the determination in step S4 is μi>Th for a plurality of consecutive images or at least a predetermined rate (for example, 80%) of the plurality of consecutive images.

Further, in the above description, the process is executed on the plurality of consecutive images. However, as a second variation, the process shown in FIG. 32 may be executed on one particular image.

Moreover, as a third variation, the moving average of the average color tone feature value μi for a plurality of consecutive images may be calculated so that the apparatus can determine whether or not, for example, the capsule endoscope 103 has passed through the EG junction, depending on whether or not the moving average value exceeds a predetermined threshold. For example, when m=2, 3, 4, . . . , and i>=m+1 (this means that m consecutive images are obtained from n images and that (m+1) is equal to or smaller than i), the moving average value is calculated on the basis of the average color tone feature value μi for images F(i−m) to Fi obtained from the m consecutive images. The apparatus then determines whether or not the moving average exceeds a predetermined threshold. Even with a very reddish intraesophageal image or the like possibly resulting from a variation in illumination conditions caused by a variation in observation distance, angle, or the like, the use of such a moving average makes it possible to eliminate the adverse effect of a slight variation in average color tone feature value to more accurately determine that, for example, the capsule endoscope 103 has passed through the EG junction.

Further, as a fourth variation, in the above example, R/(R+G+B), the ratio of pixel values calculated from the three pixel values for R, G, and B, is used as a color tone feature value. The fourth variation may use another parameter. Another parameter for the color tone feature value may be, for example, G/(R+G+B) or IHb (=32 $\log_2(R/G)$), hue, or color saturation.

Moreover, as a fifth variation, a plurality of color tone feature values may be used. For example, in step S203 in FIG. 32, R/(R+G+B) and G/(R+G+B) may be used as the ratios of pixel values calculated from the three pixel values for R, G, and B, and calculation is made of the average values of these color tone feature values, that is, the average value μ1$i$ of the color tone feature value (R/(R+G+B)) for all the pixels in each image and the average value μ2$i$ of the color tone feature value (G/(R+G+B)) for all the pixels in the image. In step S204, the apparatus determines whether or not for the average values μ1$i$ and μ2$i$, μ1$i$>Th1 and μ2$i$>Th2.

Further, as a sixth variation, the passage of the capsule endoscope 103 through the EG junction or the like may be detected on the basis of the amount of variation in average color tone feature value. That is, the apparatus may determine, instead of whether or not the average color tone feature value obtained from each of the series of consecutive images exceeds a predetermined threshold, whether or nor the amount of variation in the average color tone feature value for two images exceeds a predetermined threshold. That is, the average color tone feature value for each image is compared with that for the preceding or succeeding image. If the difference between the two average color tone feature values exceeds a predetermined threshold, the apparatus may determine that, for example, the capsule endoscope 103 has moved from the esophagus into the EG junction or from the EG junction into the stomach. The apparatus determines whether or not the differential value (μi−μ(i−m1)) between the average color tone feature values μ(i−m1) and μi for the images F(i−m1) and Fi has varied by a predetermined threshold or more. m1 is 1, 2, 3, . . . .

The color tone of the mucosa may vary owing to individual differences in mucosa color, the presence of a lesion such as the Barrett esophagus, or a variation among image pickup systems. The sixth variation thus makes it possible to determine whether or not, for example, the capsule endoscope 103 has passed through the EG junction without undergoing the adverse effect of the individual differences or the like.

Moreover, in this case, a variation in average color tone feature value may be detected by calculating the differential value of the average color tone feature values.

Figure 35:
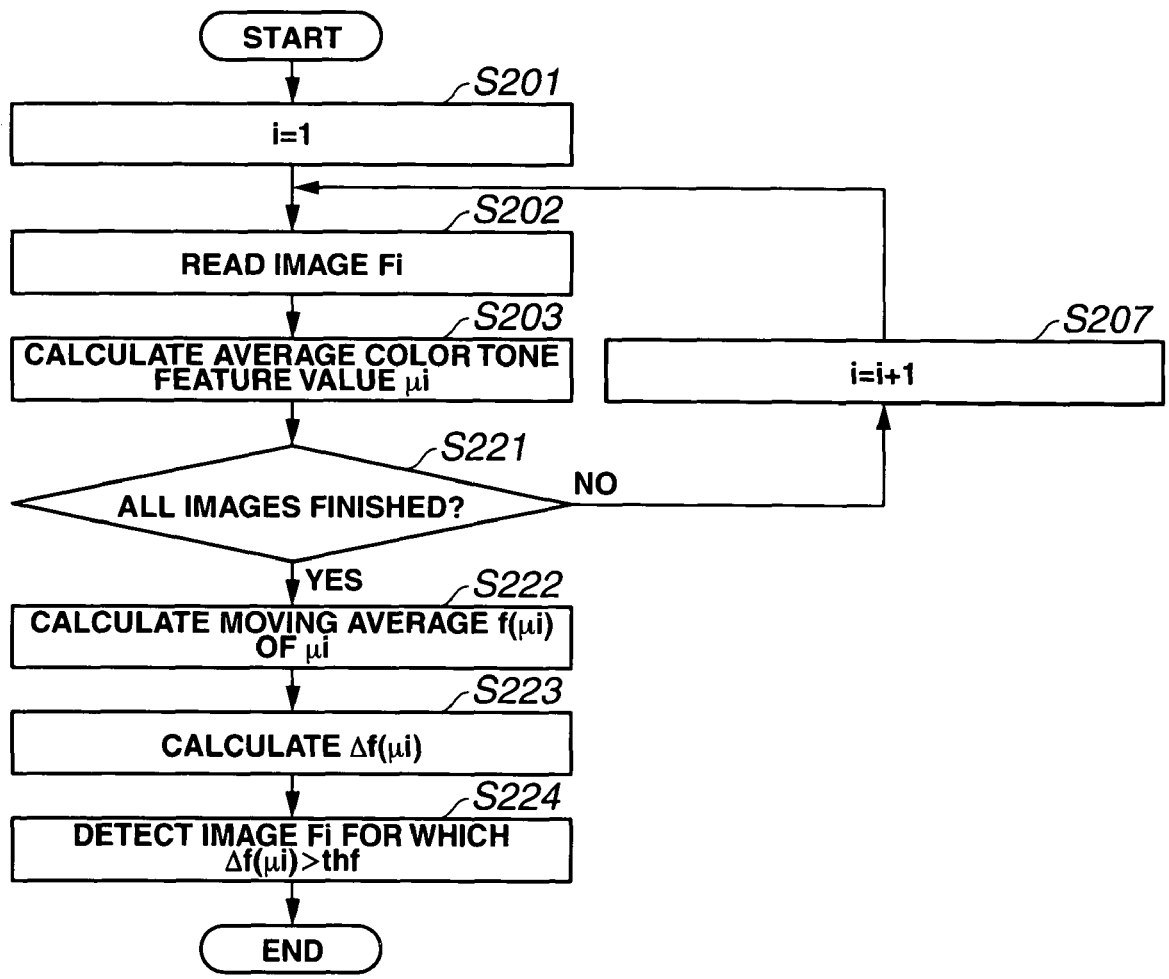
FIG. 35 is a flowchart showing an example of the flow of a process of detecting a variation in average color tone feature value by calculating a differential value for average color tone feature, values.

FIG. 35 is a flowchart showing an example of the flow in which a variation in average color tone feature value is detected by calculating the differential value of the average color tone feature values.

Image data on each image is subjected to a preprocess such as inverse gamma correction or noise removal before the process shown in FIG. 35 is executed, as described in conjunction with the process shown in FIG. 32. The processing from step S201 to step S203 is the same as the processing from step S201 to step S203 shown in FIG. 32. That is, to start the process with the first frame, first, the frame number i is set at 1 (step S201). Then, image data on the image Fi with the frame number i is read from the storage device (not shown) in the terminal apparatus 7 (step S202). The average color tone feature value µi is calculated on the basis of the read image data on the image Fi (step S203).

The apparatus determines whether or not the process has been executed on all the images, that is, the process has been finished on all the images (step S221). If the process has not been finished on all the images, the determination in step S221 is NO. Then, a process of changing i to i+1 is executed (step S207), and the process shifts to step S202.

When the process has been finished on all the images, the determination in step 221 is YES, and for obtained plural average color tone feature value µi, a moving average value f(µi) is calculated over a predetermined range, that is, over a predetermined number of consecutive images for smoothing (step S222). A differential value ∆f(µi) is calculated on the basis of a temporal variation in the moving average value f(µi) (step S223).

The image Fi is identified and detected which corresponds to the differential value ∆f(µi) exceeding a predetermined threshold thf (step S224). Steps S3 to S24 constitute a detection section that detects the boundary of the gastrointestinal tract.

This enables the detection of a plurality of images for which the amount of variation in color tone exceeds the threshold. Even with individual differences in mucosa color or the like, the apparatus can determine whether or not, for example, the capsule endoscope 103 has passed through the EG junction without undergoing the adverse effects of the individual differences or the like.

Moreover, as a seventh variation, a standard deviation or a variance may be used in place of the average value of color tone feature values.

Figure 36:
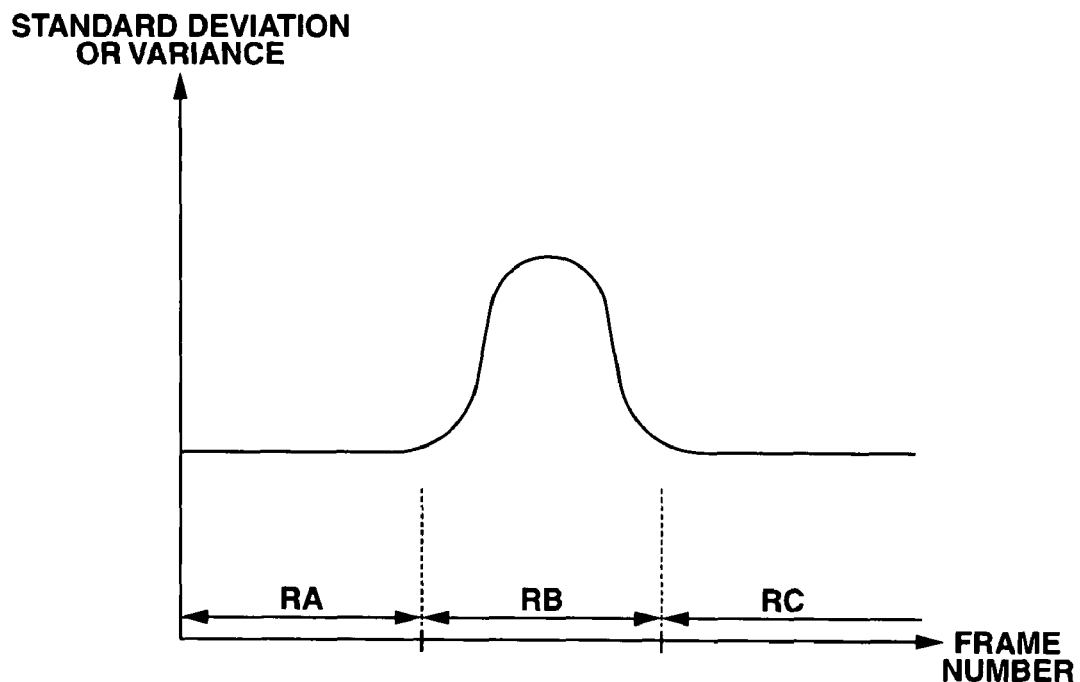
FIG. 36 is a graph illustrating a variation in the standard deviation or variance of the color tone feature in a series of endoscopic images obtained in accordance with a seventh variation of the fourth embodiment.

For example, FIG. 36 is a graph illustrating a variation in the standard deviation or variance of the color tone feature value for a series of endoscopic images obtained. In FIG. 36, the axis of abscissa indicates the image numbers (frame numbers), along the time series, of endoscopic images of the area extending from the esophagus squamous epithelium through the EG junction to the stomach. The axis of ordinate indicates the standard deviation σi or variance vi of the color tone feature value for the endoscopic image corresponding to each of the image numbers.

The color tone of the images picked up by the capsule endoscope 103 swallowed through the subject's mouth varies as shown in FIG. 33. However, the calculated standard deviation or variance of the color tone feature value R/(R+G+B) varies as shown in FIG. 36. That is, in each of the images of the squamous epithelium RA of the esophagus and the stomach portion RC of the columnar epithelium, the color tone is uniform, and the standard deviation vi or variance vi of the color tone feature value R/(R+G+B) is thus small. However, for the EG junction RB, located between the squamous epithelium RA of the esophagus and the stomach portion RC of the columnar epithelium, a greater standard deviation σi or variance vi is observed.

Consequently, on the basis of the standard deviation σi or variance vi of the color tone feature value for each image, the apparatus can determine whether or not, for example, the capsule endoscope 103 is passing through the EG junction.

Moreover, instead of the standard deviation σi or variance vi of the color tone feature value, a variation coefficient for the standard deviation σi or variance vi (=standard deviation σi/average color tone feature value µi) may be used.

Figure 37:
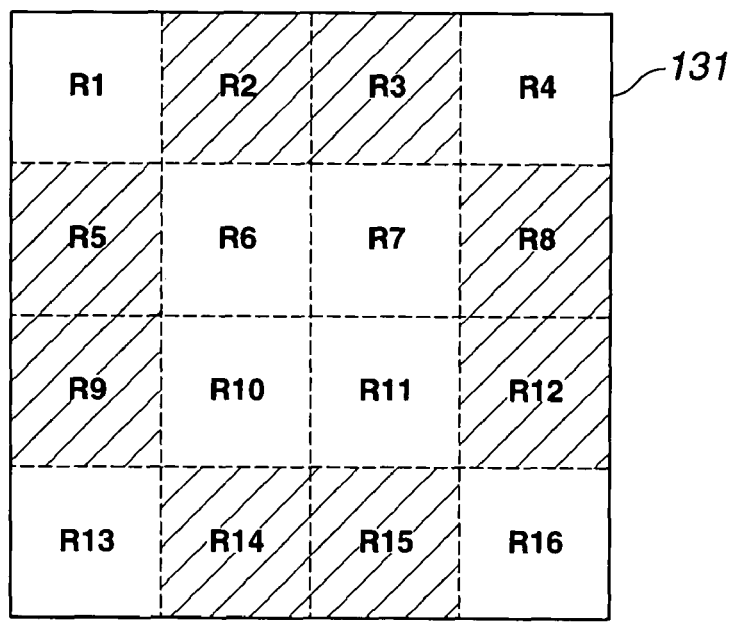
FIG. 37 is a diagram showing an example of areas of a frame image which are subjected to image processing in accordance with the fourth embodiment and a variation thereof.

Moreover, the above examples use the image data on all the pixels in each frame image. However, as an eighth variation, instead of processing all the pixels, only the pixels in predetermined regions of each frame may be sampled for processing as shown in FIG. 37. FIG. 37 shows an example of regions in each frame image 131 which are to be subjected to the image processing in accordance with the above present embodiment and variations.

Each frame image 131 is divided into predetermined regions. In FIG. 37, each image 131 is divided into 16 rectangular regions. The above processing is executed only on predetermined ones (R2, R3, R5, R8, R9, R12, R14, and R15) of the resulting regions, that is, only on the regions of interest (ROI). In particular, since the esophagus is a luminal organ, the regions other than the one corresponding to the center of the visual field may be set to be the regions of interest (ROI) in order to more accurately calculate the color tone of the mucosa surface.

Accordingly, processing only the regions of interest (ROI) reduces the amount of calculation required, enabling an increase in processing speed.

Moreover, when only the regions of interest (ROI) are processed, the processing speed may further be increased by, instead of processing all the frames, processing only the pixels in the regions of interest (ROI) in every k (k=1, 2, 3, . . . ) frames. In particular, a large number of images are picked up for the interior of the esophagus. Consequently, accurate determinations may be made in spite of minor decimations.

As described above, the present embodiment (including the variations) makes it possible to determine, on the basis of the color tone feature value for each luminal image, whether or not the image shows that the capsule endoscope is about to enter the EG junction or is passing through the EG junction.

In accordance with the present embodiment, the threshold process is applied to the calculated feature value to detect whether or not each image shows that the capsule endoscope is about to enter the EG junction or is passing through the EG junction. However, for example, an identification function such as a well-known linear discrimination function may be used for the detection. Alternatively, a feature value in accordance with another embodiment may be combined with the present embodiment.

Fifth Embodiment

Now, with reference to the drawings, description will be given of a cardia detection apparatus utilizing a capsule endoscope apparatus and a method for the cardia detection in accordance with a fifth embodiment. Endoscopic images to be processed in accordance with the present embodiment are a series of endoscopic images picked up by the capsule endoscope apparatus 101 as in the case of the fourth embodiment. Accordingly, the configuration of the cardia detection apparatus is similar to that in the fourth embodiment and will not be described below.

The above fourth embodiment uses the color tone feature value. The cardia detection apparatus, a luminal image processing apparatus in accordance with the present embodiment, is different from the fourth embodiment in that the apparatus uses brightness information on each image to determine whether or not, for example, the image shows that the capsule endoscope is passing through the EG junction.

Figure 38:
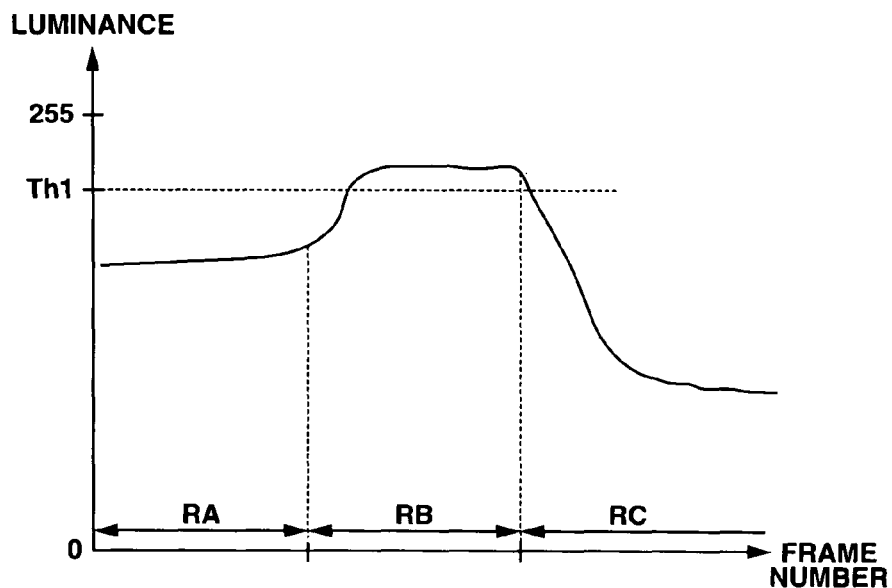
FIG. 38 is a schematic graph illustrating a variation in the brightness of a series of endoscopic images obtained, specifically, a variation in luminance, in accordance with a fifth embodiment.

FIG. 38 is a schematic graph illustrating a variation in brightness among a series of endoscopic images obtained, specifically a variation in luminance among the images. In FIG. 38, the axis of abscissa indicates the image numbers (frame numbers), along the time series, of endoscopic images of the area extending from the esophagus squamous epithelium through the EG junction to the stomach. The axis of ordinate indicates the luminance of the endoscopic image corresponding to each of the image numbers.

The luminance of images picked up by the capsule endoscope 103 swallowed through the subject's mouth indicates the brightness of the images. The luminance varies as shown in FIG. 38. That is, the luminance varies between the squamous epithelium RA of the esophagus and the stomach portion RC of the columnar epithelium. Further, the luminance for the EG junction RB, located between the squamous epithelium RA and the stomach portion RC, is different from those for the squamous epithelium RA and the stomach portion RC. As shown in FIG. 38, for example, with the luminance calculated on the basis of the three pixel values for R, G, and B, the esophagus squamous epithelium RA exhibits a large average luminance value except for a dark portion and a halation portion of the image because the esophagus squamous epithelium RA is a relatively narrow luminal organ and lies close to the mucosa wall. The stomach portion RC exhibits a relatively low luminance. The EG junction RB, located between the esophagus squamous epithelium RA and the stomach portion RC, exhibits a larger luminance value than the esophagus squamous epithelium RA because the closed cardia is viewed from the front in the esophagus, composed of a lumen.

Thus, when the brightness information on the image, varying gradually, exceeds a predetermined threshold Th1, the apparatus determines that, for example, the endoscope is passing through the EG junction or is about to enter the EG junction. That is, on the basis of a variation in the brightness information on the picked-up image, the closed cardia is detected when the capsule endoscope 103 is about to enter the EG junction or is passing through the EG junction. Specifically, an average luminance value or the like is used as the brightness information in order to allow the passage or the like to be reliably determined.

Figure 39:
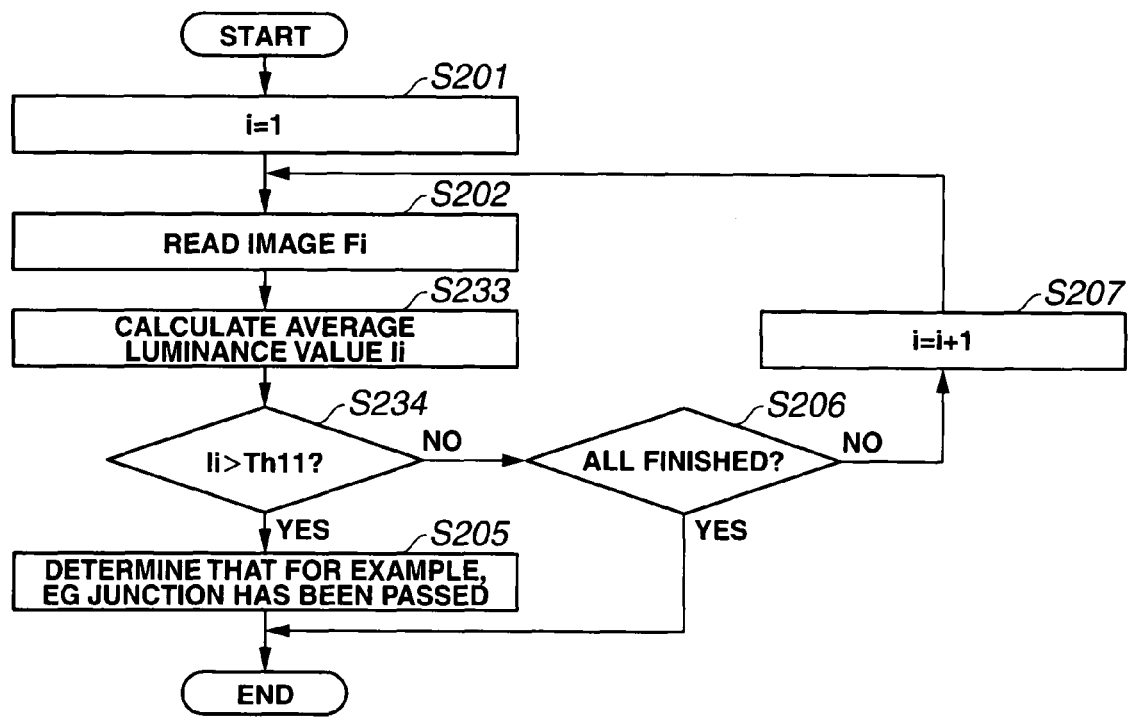
FIG. 39 is a flowchart showing an example of the flow of a process of detecting the cardia upon passage through the EG junction, the process being executed by a terminal apparatus on the basis of the series of endoscopic images obtained in accordance with the fifth embodiment.

Like FIG. 32, FIG. 39 is a flowchart showing an example of the flow of a process of detecting the cardia when the EG junction is passed; the process is executed by the terminal apparatus 107 on the basis of a series of endoscopic images obtained. The process shown in FIG. 39 is substantially similar to that shown in FIG. 32. A series of endoscopic images picked up by the endoscope swallowed through the subject's mouth comprise a plurality of frames. The process shown in FIG. 39 is executed on each frame. The image data on each endoscopic image is subjected to a preprocess such as inverse gamma correction or noise removal before the process shown in FIG. 39 is executed. In FIG. 39, steps similar to those shown in FIG. 32 are denoted by the same step numbers, and the description of these steps is simplified. Further, in the description below, the luminance value is used as brightness information. The case in which the G or B pixel data value is used brightness information will not be described because this case differs from the one in which the luminance value is used as brightness information only in threshold data used and in that the determination depends on whether or not the value of the pixel data is smaller than the threshold.

First, to start processing with the first one of a series of images to be subjected to the process shown in FIG. 39, the frame number i is set at 1 (step S201). Then, the image data on the image Fi with the frame number i is read from the storage device (not shown) in the terminal apparatus 107 (step S202).

An average luminance value Ii is calculated from the read image data on the image Fi (step S233). The average luminance value Ii is the average of the luminance values of all the pixels contained in each image. In this case, the luminance value I is a feature value indicating the brightness of the image as described above. For example, the luminance I is calculated by 0.6R+0.3G+0.1B. Step S233 constitutes a feature value calculation step or a feature value calculation section which calculates the average luminance value based on the luminance values of all the pixels in each image Fi.

Then, the apparatus determines whether or not the average luminance value Ii exceeds a predetermined threshold Th11 (step S234).

Adjusting the threshold Th11 makes it possible to determine whether or not the read image Fi was picked up in the vicinity of the inlet to the EG junction or in the central portion of the EG junction.

If the determination in step S234 is YES, that is, when the average luminance value Ii exceeds the predetermined threshold Th11, the apparatus determines that the image Fi was picked up when the capsule endoscope 103 was about to enter the EG junction or was passing through the EG junction (step S205). Steps 234 and 205 constitute a boundary detection section that detects the boundary of the gastrointestinal tract on the basis of the calculated average luminance value Ii and a determination section that determines that the intraluminal image shows the area between the esophagus and the cardia on the basis of the detection result for the EG junction, corresponding to the boundary.

If the determination in step S234 is NO, that is, when the average luminance value Ii does not exceed the predetermined threshold Th11, the apparatus determines whether or not the process shown in FIG. 39 has been finished on the series of images to be subjected to the process shown in FIG. 39 (step S206). When the process has been finished on all the images, the determination in step S206 is NO. The process is thus ended. If the determination in step S206 is NO, there remains an unprocessed image. Accordingly, a process of changing i to i+1 is executed (step S207), and the process from step S202 to step S234 is subsequently repeated. Steps S233 to S205 constitute a detection section that detects the boundary of the gastrointestinal tract.

Also in the present embodiment, in step S205, when the average luminance value Ii, brightness information, exceeds the threshold Th11, the image Fi was picked up when the capsule endoscope 103 was about to enter the EG junction or was passing through the EG junction. In other words, the apparatus may also determine that the capsule endoscope 103 will subsequently pass through the closed cardia or reach the interior of the stomach. This allows the cardia to be detected.

Now, description will be given of a specific example of the average luminance value Ii, described with reference to FIG. 39.

Figure 40:
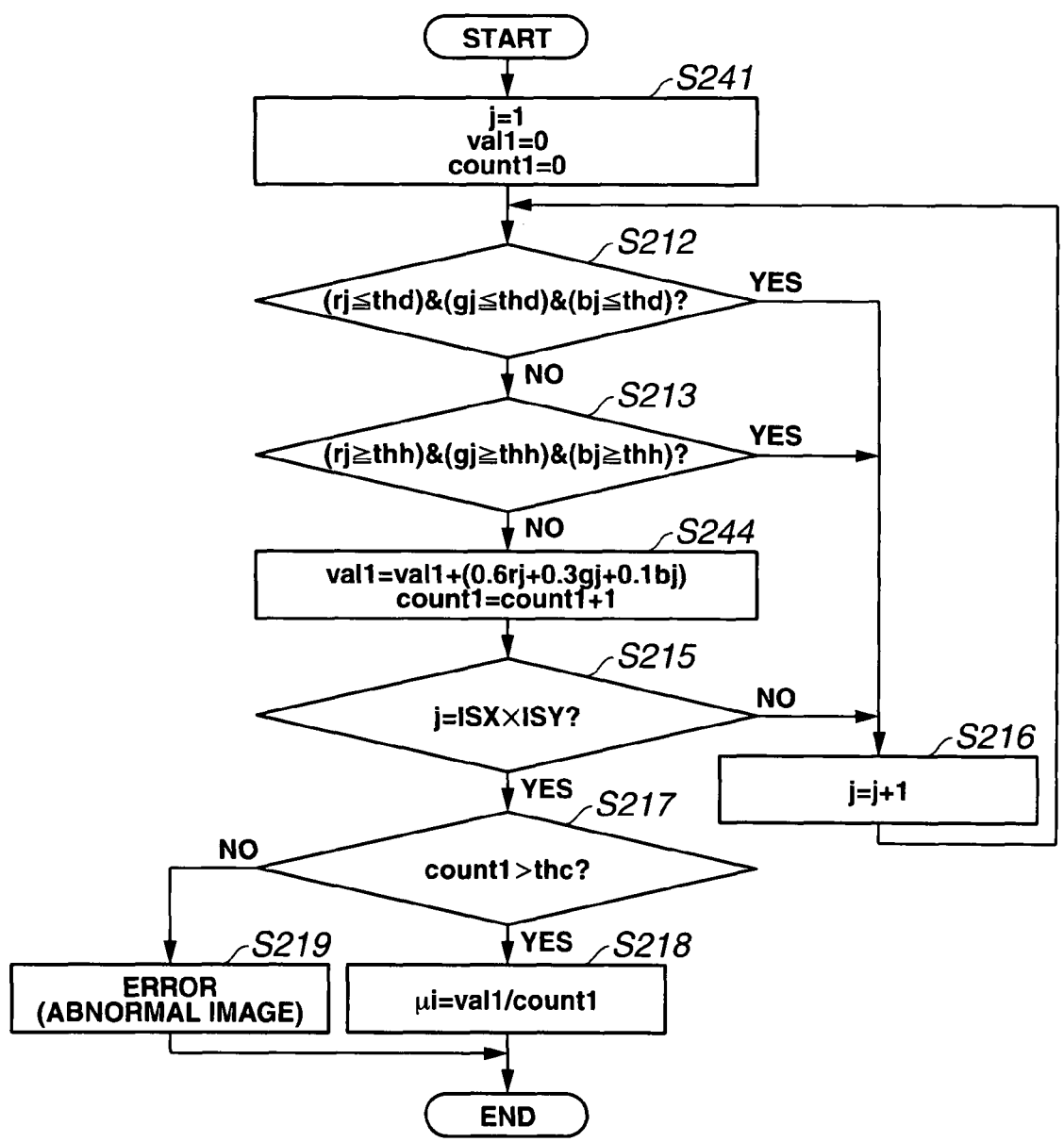
FIG. 40 is a flowchart showing an example of the flow of a process in step S33 shown in FIG. 39.

FIG. 40 is a flowchart showing an example of the flow of the process in step S233 which uses, as the average luminance value Ii, (0.6R+0.3G+0.1B) calculated from the three pixel values for R, G, and B executed on each frame image. The process shown in FIG. 40 calculates the average luminance value Ii by calculating the luminance value (0.6R+0.3G+0.1B) from three pixel values rj, gj, bj for R, G, and B for each of the pixels in each frame.

FIG. 40 includes process steps similar to those shown in FIG. 34. A similar process is denoted by the same step numbers and will not be described below. Reference character j denotes a number identifying a pixel in the image data on each frame.

First, j is set at 1, val1 is set at 0, and count1 is set at 0 (step S241). Here, val1 denotes a variable required to determine the sum of brightness feature values, and count1 denotes a variable required to determine the number of pixels used to calculate the average luminance value Ii.

Then, the apparatus determines in step S212 whether or not the jth pixel belongs to the dark portion. If the jth pixel is determined to belong to the dark portion, the process proceeds to step S216. If the jth pixel is determined not to belong to the dark portion, the process proceeds to step S213.

Then, the apparatus determines in step S213 whether or not the jth pixel is extremely bright, that is, the jth pixel belongs to a halation portion. If the jth pixel is determined to be a halation pixel, the process proceeds to step S216. If the jth pixel is determined not to be a halation pixel, the process proceeds to step S244.

In steps S212 and S213, for the R image, G image, and B image, each of the thresholds thd and thh has the same value for rj, gj, and bj. However, for the biological mucosa, the R image generally tends to be brightest. Accordingly, the threshold may be set higher for rj than for gj and bj. Alternatively, the threshold may vary among rj, gj, and bj.

In step S244, val1=val1+(0.6rj+0.3gj+0.1bj) and count1=count1+1 are calculated. To determine the sum of the brightness feature values, the luminance feature value (0.6rj+0.3gj+0.1bj), which is a brightness feature value, is added to the variable val1 and the variable count1 is incremented by one.

In step S215, the apparatus determines whether or not the process from step S212 to step S244 has been executed on all the pixels. If the process from step S212 to step S244 has not been executed on all the pixels, then in step S216, 1 is added to the number j identifying the pixel (=j+1) and steps S212 to S244 are executed on the next pixel. If the process from step S212 to step S244 has been executed on all the pixels, the apparatus determines whether or not count1 is greater than the threshold thc (step S217). If a sufficient number of pixels are present which are effective for brightness evaluation, the average luminance value Ii is calculated by dividing the variable val1 by the variable count1 (step 218). Specifically, Ii=val1/count1.

If a sufficient number of pixels are not present which are effective for brightness evaluation, that frame image is considered to be an error, that is, an abnormal image (step S219). The average brightness value Ii is determined to be, for example, 0 (zero). In step S234 in FIG. 39, the apparatus determines that the average brightness value Ii does not exceed the threshold Th1.

In the above description, the cardia is closed. However, the present embodiment is also applicable to the open cardia. The cardia can be detected on the basis of whether or not the luminance exceeds the predetermined threshold.

Now, variations of the present embodiment will be described.

In FIGS. 39 and 40, described above, the apparatus determines whether or not, for example, the capsule endoscope has passed through the EG junction or the cardia, on the basis of each frame image. However, as a first variation, the apparatus may determine that, for example, the capsule endoscope 103 has passed through the EG junction when the determination in step S234 is Ii>Th11 for a plurality of consecutive images or at least a predetermined rate (for example, 80%) of the plurality of consecutive images.

Further, in the above description, the process is executed on the plurality of consecutive images. However, as a second variation, the process shown in FIG. 39 may be executed on one particular image.

Moreover, as a third variation, the moving average of the average brightness value Ii for a plurality of consecutive images may be calculated so that the apparatus can determine whether or not, for example, the capsule endoscope 103 has passed the EG junction, depending on whether or not the moving average value exceeds a predetermined threshold. For example, when m=2, 3, 4, . . . , and i>=m+1 (this means that m consecutive images are obtained from n images and that (m+1) is equal to or smaller than i), the moving average value is calculated on the basis of the average brightness value for images F(i-m) to Fi obtained from the m consecutive images. The apparatus then determines whether or not the moving average exceeds a predetermined threshold. Even with a very reddish intraesophageal image or the like possibly resulting from a variation in illumination conditions caused by a variation in observation distance, angle, or the like, the use of such a moving average makes it possible to eliminate the adverse effect of a slight variation in average brightness value to more accurately determine that, for example, the capsule endoscope 103 has passed through the EG junction.

Further, in the above example, the luminance calculated from the three pixel values for R, G, and B as described above is used as a brightness feature value. As a fourth variation, G or B pixel data may be used in place of the luminance.

Figure 41:
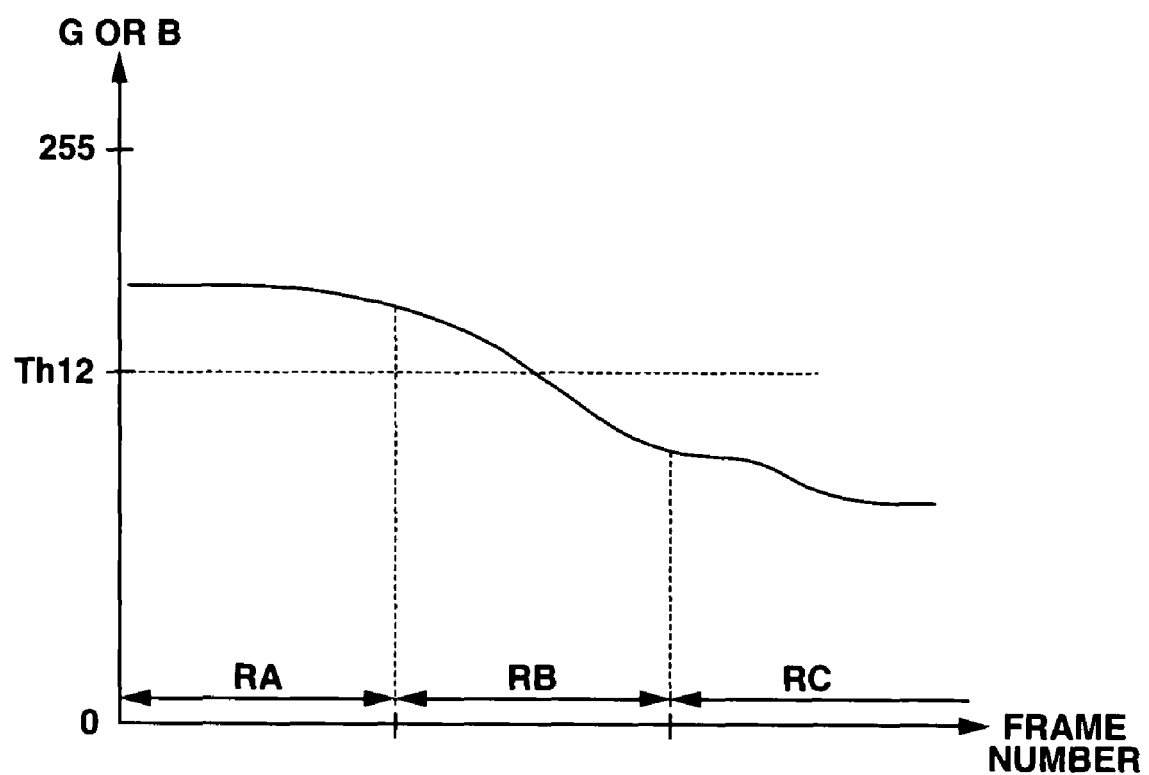
FIG. 41 is a schematic graph illustrating a variation in G or B pixel data in the series of endoscopic images, the G or B pixel data being used as brightness information on the images instead of the luminance calculated from the three pixel values for R, G, and B as described above.

FIG. 41 is a schematic graph illustrating a variation in G or B pixel data on a series of endoscopic images in the case in which G or B pixel data is used in place of the luminance calculated from the three pixel values for R, G, and B as described above. In FIG. 41, the axis of abscissa indicates the image numbers (frame numbers), along the time series, of endoscopic images of the area extending from the esophagus squamous epithelium through the EG junction to the stomach. The axis of ordinate indicates the G or B pixel data value for the endoscopic image corresponding to each of the image numbers.

That is, as shown in FIG. 41, the G or B pixel data value varies between the squamous epithelium RA of the esophagus and the stomach portion RC of the columnar epithelium. Further, the G or B pixel data value for the EG junction RB, located between the squamous epithelium RA and the stomach portion RC, is different from those for the squamous epithelium RA and the stomach portion RC. Specifically, in the EG junction RB, the G or B pixel data value decreases gradually from the squamous epithelium RA of the esophagus, which has a white color tone and thus a greater pixel data value, to the stomach portion RC of the columnar epithelium, which has a smaller pixel data value.

Accordingly, when the brightness information on the image, varying gradually, exhibits a value smaller than a predetermined threshold Th 12, the apparatus determines that, for example, the capsule endoscope 103 is passing through the EG junction or is about to enter the EG junction. That is, on the basis of a variation in the brightness information on the picked-up image, the apparatus determines that, for example, the capsule endoscope 103 is passing through the EG junction. Specifically, to make a reliable determination for the passage or the like, the average value of the G or B pixel data value is utilized as brightness information.

Moreover, as a fifth variation, a plural pieces of brightness information may be used. For example, in step S233 in FIG. 39, the luminance value and G pixel data for the pixel calculated from the three pixel values for R, G, and B are used to calculate the average values of these values, that is, the average brightness value I1$i$ of all the pixels in each image and the average value I2$i$ of the G pixel data. In step S234, the apparatus determines whether or not for the average brightness value I1$i$ and the average value I2$i$ for the G pixel data, I1$i$>Th13 and I2$i$<Th14.

Further, as a sixth variation, the passage of the capsule endoscope 103 through the EG junction or the like may be detected on the basis of the amount of variation in brightness information. That is, the apparatus may determine, instead of whether or not the brightness information obtained from each image of the series of consecutive images exceeds a predetermined threshold, whether or nor the amount of variation in the brightness information on two consecutive images exceeds a predetermined threshold. That is, for the brightness information on each image, the average luminance value for the image is compared with that for the preceding or succeeding image. If the difference between the two average luminance values exceeds a predetermined threshold, the apparatus may determine that, for example, the capsule endoscope 103 has moved from the esophagus into the EG junction or from the EG junction into the stomach. The apparatus determines whether or not the differential value (Ii−I(i−m1)) between the average luminance values I(i−m1) and Ii for the images F(i−m1) and Fi has varied by a predetermined threshold or more. m1 is 1, 2, 3, . . . .

The color tone of the mucosa may vary owing to individual differences in mucosa color, the presence of a lesion such as the Barrett esophagus, or a variation among image pickup systems. The sixth variation thus makes it possible to determine whether or not, for example, the capsule endoscope 3 has passed through the EG junction without undergoing the adverse effect of the individual differences or the like.

Moreover, in this case, a variation in brightness information may be detected by calculating the differential value of the average luminance values.

Figure 42:
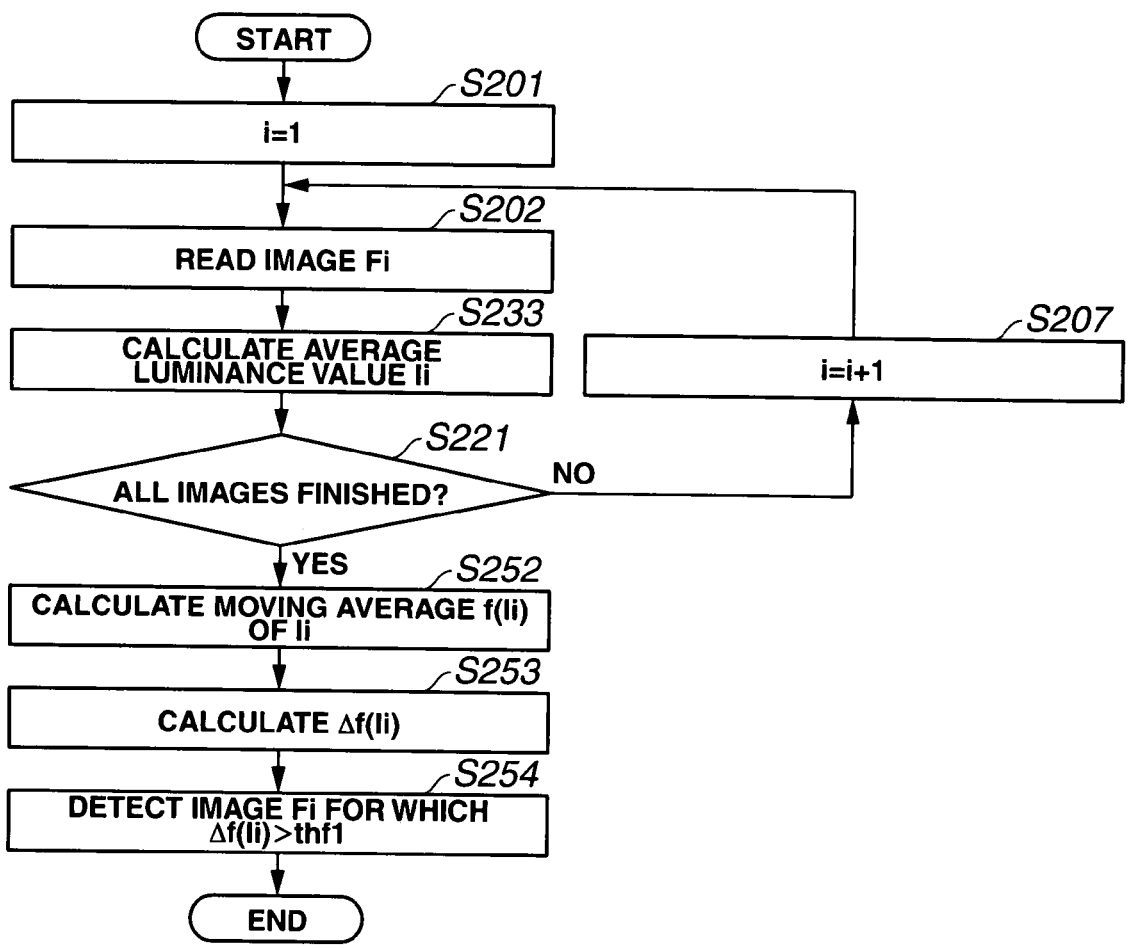
FIG. 42 is a flowchart showing an example of the flow of a process of detecting a variation in brightness by calculating a differential value for average luminance values in accordance with the fifth embodiment.

FIG. 42 is a flowchart showing an example of the flow of a process of detecting a variation in brightness by calculating the differential value of the average luminance values. Steps similar to those shown in FIG. 35 are denoted by the same step numbers and the description of these steps is simplified.

As described above in conjunction with the process shown in FIG. 39, the image data on each image is subjected to a preprocess such as inverse gamma correction or noise removal before the process shown in FIG. 42 is executed. The process from step S201 to step S233 is the same as that from step S201 to step S233 shown in FIG. 39.

The apparatus determines whether or not the process has been executed on all the images, that is, the process has been finished on all the images (step S221). If the process has not been finished on all the images, the determination in step S221 is NO. Then, a process of changing i to i+1 is executed (step S207), and the process shifts to step S202.

When the process has been finished on all the images, the determination in step 221 is YES, and a moving average value f(Ii) is calculated over a predetermined range, that is, over a predetermined number of consecutive images for smoothing (step S252). A differential value Δf(Ii) is calculated on the basis of a temporal variation in the moving average value f(Ii) (step S253).

The image Fi is identified and detected which corresponds to the differential value Δf(Ii) exceeding a predetermined threshold thf1 (step S254). Steps S233 to S254 constitute a detection section that detects the boundary of the gastrointestinal tract.

This enables the detection of a plurality of images for which the amount of variation in brightness exceeds the threshold. Even with individual differences in mucosa color or the like, the apparatus can determine whether or not, for example, the capsule endoscope 103 has passed through the EG junction without undergoing the adverse effects of the individual differences or the like.

Moreover, as a seventh variation, the closed cardia may be detected on the basis of the distribution of brightness. For example, instead of the average value for brightness information, the standard deviation or the variance may be used as is the case with the fourth embodiment. This makes it possible to determine whether or not, for example, the capsule endoscope 103 is passing through the EG junction on the basis of the standard deviation or variance of brightness information on a series of endoscopic images obtained. Specifically, the standard deviation of the brightness of R image data is determined. If the standard deviation is smaller than a predetermined threshold, the apparatus determines that the closed cardia is being viewed from the front. This is because the brightness of the image is relatively uniform when the closed cardia is viewed from the front. Moreover, instead of the standard deviation or variance of the average luminance value, a variation coefficient for the standard deviation or variance (=standard deviation/average brightness value) may be used.

Moreover, the above examples use the pixel data on all the pixels in each frame image. However, as an eighth variation, instead of processing all the pixels, only the pixels in predetermined regions of each frame may be sampled for processing as described above with reference to FIG. 37 for the fourth embodiment. FIG. 37 shows an example of regions in each frame image which are to be subjected to the image processing in accordance with the above present embodiment and variations.

Each frame image is divided into predetermined regions. In FIG. 37, each image is divided into 16 rectangular regions. The above process is executed only on preset ones (R2, R3, R5, R8, R9, R12, R14, and R15) of the resulting regions, that is, only on the regions of interest (ROI). In particular, since the esophagus is a luminal organ, the regions other than the one corresponding to the center of the visual field may be set to be the regions of interest (ROI) in order to more accurately calculate the color tone of the mucosa surface.

Accordingly, processing only the regions of interest (ROI) reduces the amount of calculation required, enabling an increase in processing speed.

Moreover, when only the regions of interest (ROI) are processed, the processing speed may further be increased by, instead of processing all the frames, processing only the pixels in the regions of interest (ROI) in every k (k=1, 2, 3, . . . ) frames. In particular, a large number of images are picked up for the interior of the esophagus. Consequently, accurate determinations may be made in spite of minor decimations.

As described above, the present embodiment (including the variations) makes it possible to determine, on the basis of brightness information on each image, whether or not, for example, the image shows that the capsule endoscope is about to enter the EG junction or is passing through the EG junction.

In accordance with the present embodiment, the threshold process is applied to the calculated feature value to detect whether or not each image shows that the capsule endoscope is about to enter the EG junction or is passing through the EG junction. However, for example, an identification function such as a well-known linear discrimination function may be used for the detection. Alternatively, a feature value in accordance with another embodiment may be combined with the present embodiment.

Sixth Embodiment

Now, with reference to the drawings, description will be given of a cardia detection apparatus utilizing a capsule endoscope apparatus and a method for the cardia detection in accordance with a sixth embodiment. Endoscopic images to be processed in accordance with the present embodiment are a series of endoscopic images picked up by the capsule endoscope apparatus 101 as in the case of the fourth embodiment. Accordingly, the configuration of the cardia detection apparatus is similar to that in the fourth embodiment and will not be described below.

The above fourth embodiment uses the color tone feature value. However, the cardia detection apparatus, a luminal image processing apparatus in accordance with the present embodiment, is characterized by detecting the open cardia to determine whether or not each image shows that, for example, the capsule endoscope moving from the esophagus toward the stomach is located near and in front of the cardia.

Figure 43:
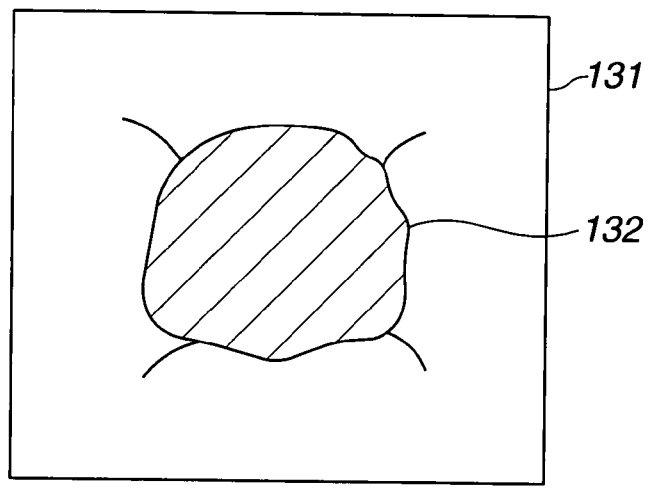
FIG. 43 is a diagram showing an example of an image in which a capsule endoscope is located in front of the open cardia in accordance with a sixth embodiment.

FIG. 43 is a diagram showing an example of an image in which the capsule endoscope 103 is located in front of the open cardia.

When the capsule endoscope 103 picks up an image of the open cardia in the lumen, the brightness of the open cardia is significantly lower than that of the surroundings. As shown in FIG. 43, when the cardia 132 is open, in the image 131 picked up by the capsule endoscope 103, the open cardia 132 appears to be a dark area. Accordingly, as the capsule endoscope 103 moves from the esophagus, through the EG junction, and closer to the cardia, the area of the cardia 132 in the image 131 increases. According to the present embodiment, when the area of the open cardia exceeds a predetermined size, the apparatus determines that the capsule endoscope 103 moving from the stomach side of the esophagus is passing through the cardia.

Figure 44:
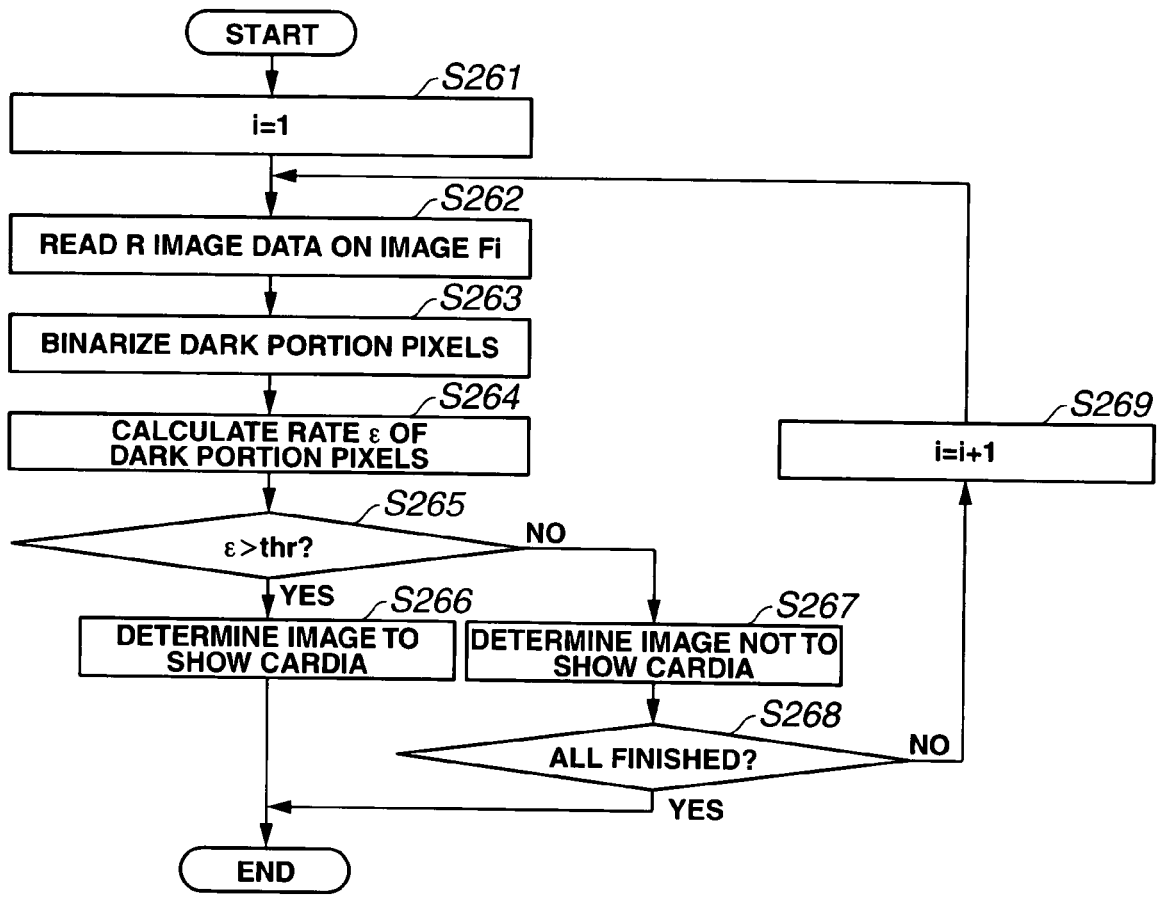
FIG. 44 is a flowchart showing an example of the flow of a process of detecting the open cardia on the basis of a series of endoscopic images in accordance with the sixth embodiment.

FIG. 44 is a flowchart showing an example of the flow of a process of detecting the open cardia on the basis of a series of endoscopic images obtained. The series of endoscopic images picked up by the endoscope swallowed through the subject's mouth comprise a plurality of frames. The process shown in FIG. 44 is executed on each of the frames. The image data on each endoscopic image is subjected to a preprocess such as inverse gamma correction or noise removal before the process shown in FIG. 44 is executed.

To start processing with the first frame of the series of images to be subjected to the process shown in FIG. 44, first, the frame number i is set at 1 (step S261). Reference character i denotes an integer from 1 to n.

Then, R image data on the image Fi with the frame number i is read from the storage device (not shown) in the terminal apparatus 7 (step S262). The image Fi comprises three planes for R, G, and B. In this case, only the R image data is read.

Although in this case, the R image data is read in order to make a cardia determination as described below, G image data or B image data on the image Fi may be used.

A dark portion pixel binarization is executed on all the pixels in the read R image data on the image Fi (step S263). Specifically, the pixel value of each pixel is compared with the predetermined threshold Th2 to execute a binarization such that dark portion pixels are set to have a value of 1, whereas the other pixels are set to have a value of 0 (zero). Reference character j denotes a number identifying a pixel in the image data on each frame. Then, whether or not the value rj for each pixel is smaller than the threshold Th2 is checked to set 1 for pixels having a value smaller than the threshold Th2, while setting 0 (zero) for the other pixels.

Then, the ratio $\epsilon$ of the dark pixels to all the pixels is calculated (step S264). In other words, the ratio $\epsilon$ is the rate of the area of the dark portion in the image. Specifically, the ratio $\epsilon$ is calculated by dividing the number of pixels determined to be dark portion pixels by the binarization in step S263, by the total number of the pixels in the R image data. When the number of dark portion pixels is defined as p1 and the size of the image Fi is defined as ISX×ISY, the ratio $\epsilon$ is p1/(ISX'ISY). Step S264 constitutes a dark portion ratio calculation step or a dark portion ration calculation section which calculates the ratio of the dark portion pixels in each image Fi.

The ratio $\epsilon$ is compared with the predetermined threshold Thr to determine whether or not the ratio $\epsilon$ of the dark portion pixels exceeds the predetermined threshold Thr (step S265). The threshold Thr is, for example, 0.8.

If the determination in step S265 is YES, that is, the dark portion accounts for more than 80% of the entire image, the image is determined to show the open cardia (step S266). The process is then ended.

If the determination in step S265 is NO, that is, the dark portion accounts for at most 80% of the entire image, the image is determined not to show the cardia (step S267). The apparatus determines whether or not the process shown in FIG. 44 has been finished on all of the series of images to be subjected to the process shown in FIG. 44 (step S268). When the process has been finished on all the images, the determination in step S268 is YES and the process is ended. If the determination in step S268 is NO, there remains an unprocessed image. Thus, a process of changing to i+1 is executed (step S269). Subsequently, steps S262 to S265 are repeatedly executed on the next image.

In step S266, when the ratio c of the dark portion pixels exceeds the predetermined threshold Thr, the apparatus determines that the open cardia has been detected. In other words, the apparatus may also determine that the endoscope will subsequently pass through the cardia or reach the interior of the stomach. Steps S263 to S266 constitute a detection section that detects the boundary of the gastrointestinal tract.

Now, variations of the present embodiment will be described below.

In the above example, only the R image data is read in order to make a cardia determination. However, G or B image data or G and B image data may further be read, and a dark portion pixel binarization may be executed on the at least two image data. Then, when the ratios $\epsilon$ of the dark portion pixels in the at least two image data all exceed the predetermined threshold Thr, the apparatus may determine that the cardia has been detected.

In FIG. 44, described above, the cardia is detected on the basis of each frame image. However, as a second variation, the apparatus may determine that the cardia has been detected when the determination in step S265 is $\epsilon$>Thr for a plurality of consecutive images or at least a predetermined rate (for example, 80%) of the plurality of consecutive images.

Further, in the above description, the process is executed on the plurality of consecutive images. However, as a third variation, the process shown in FIG. 44 may be executed on one image.

Moreover, as a fourth variation, a cardia determination may be made by, instead of calculating the ratio $\epsilon$ of the dark portion pixels to all the pixels, for example, calculating and dividing the total number of pixels in the non-dark portion, in the above example, pixels P0 having a value of at least the threshold Th2, by the total number of pixels in the image to calculate the ratio cl of the pixels in the non-dark portion, or calculating the ratio of the number p0 of the non-dark portion pixels to the number p1 of the dark portion pixels (p0/p1; p1 is not 0 (zero)).

Further, as a fifth variation, the threshold Thr may be varied depending on the distance between the capsule endoscope 103 and the cardia observed when the cardia is detected. In other words, the threshold Thr may be varied depending on the distance between the capsule endoscope 3 and the cardia observed when the cardia is to be detected. For example, setting Thr at 0.5 enables the cardia to be detected more quickly than setting Thr at 0.8 as described above.

As described above, the present embodiment enables the cardia to be detected on the basis of the area of the dark portion in the image.

In accordance with the present embodiment, the threshold process is applied to the calculated feature value to detect the open cardia. However, for example, an identification function such as a well-known linear discrimination function may be used for the detection. Alternatively, a feature value in accordance with another embodiment may be combined with the present embodiment.

Seventh Embodiment

Now, with reference to the drawings, description will be given of a cardia detection apparatus utilizing a capsule endoscope apparatus and a method for the cardia detection in accordance with a seventh embodiment. The present embodiment is characterized by detecting the open cardia on the basis of a shape. Endoscopic images to be processed in accordance with the present embodiment are a series of endoscopic images picked up by the capsule endoscope apparatus 101 as in the case of the fourth embodiment. Accordingly, the configuration of the cardia detection apparatus is similar to that in the fourth embodiment and will not be described below.

The cardia detection apparatus, a luminal image processing apparatus in accordance with the present embodiment, is characterized by detecting the shape of the open cardia to determine whether or not each image shows that, for example, the capsule endoscope moving from the esophagus toward the stomach is located near and in front of the cardia.

Figure 45:
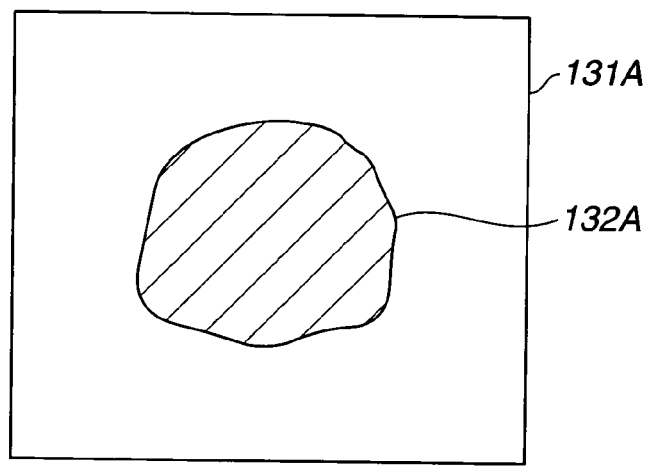
FIG. 45 is a diagram showing an example of an image obtained when the capsule endoscope passes through the open cardia in accordance with a seventh embodiment.

FIG. 45 is a diagram showing an example of an image picked up when the capsule endoscope 103 passes through the open cardia. An image 131A contains the open cardia 132A, corresponding to a dark image.

Figure 46:
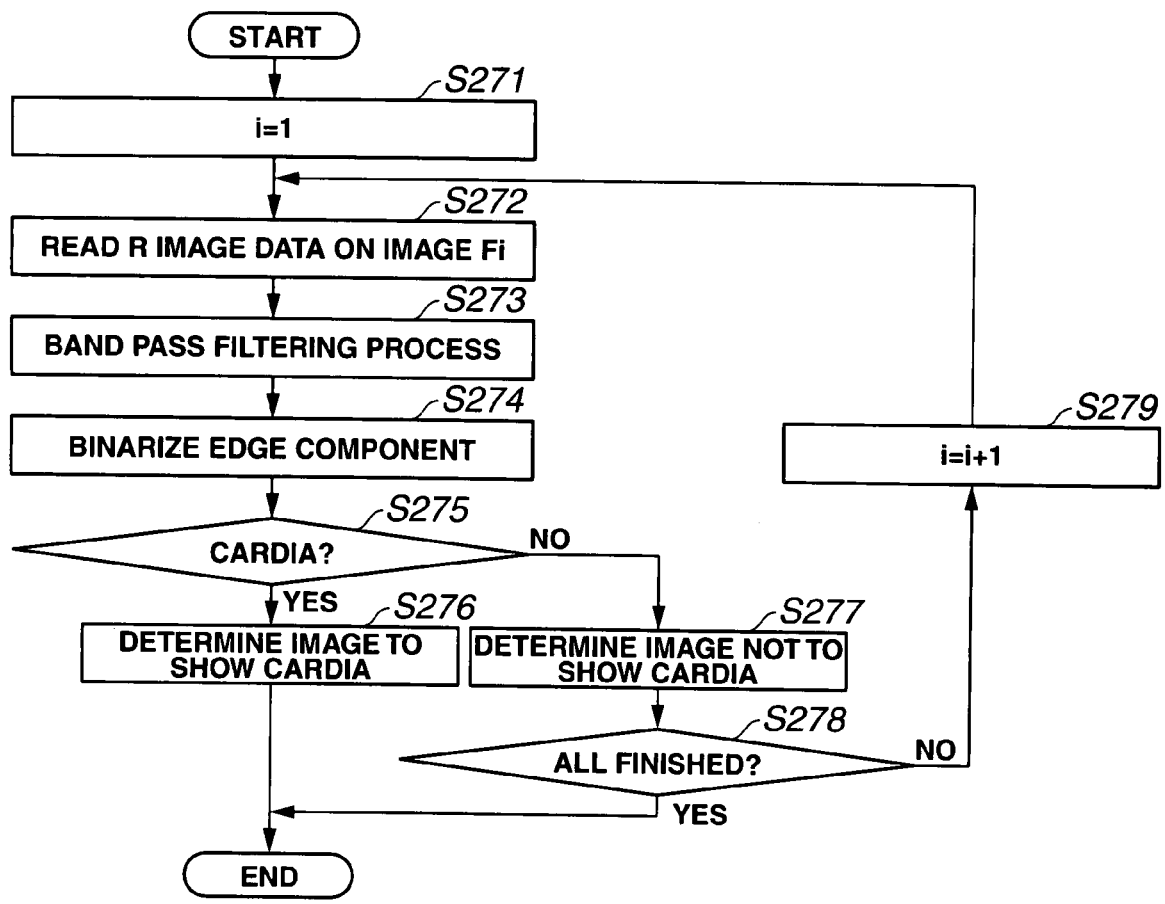
FIG. 46 is a flowchart showing an example of a process of detecting the open cardia on the basis of a series of endoscopic images in accordance with the seventh embodiment.

FIG. 46 is a flowchart showing an example of the flow in which the open cardia is detected on the basis of a series of endoscopic images obtained. The series of endoscopic images picked up by the endoscope swallowed through the subject's mouth comprise a plurality of frames. The process shown in FIG. 46 is executed on each of the frames. The image data on each endoscopic image is subjected to a preprocess such as inverse gamma correction or noise removal before the process shown in FIG. 46 is executed.

To start processing with the first frame of the series of images to be subjected to the process shown in FIG. 46, first, the frame number i is set at 1 (step S271). Reference character i denotes an integer from 1 to n.

Then, R image data on the image Fi with the frame number i is read from the storage device (not shown) in the terminal apparatus 7 (step S272). The image Fi comprises three planes for R, G, and B. In this case, only the R image data is read.

A bandpass filtering process is executed on the read R image data on the image Fi (step S273). The bandpass filtering is implemented by a convolution process using a well-known digital filter or on a Fourier surface.

Figure 47:
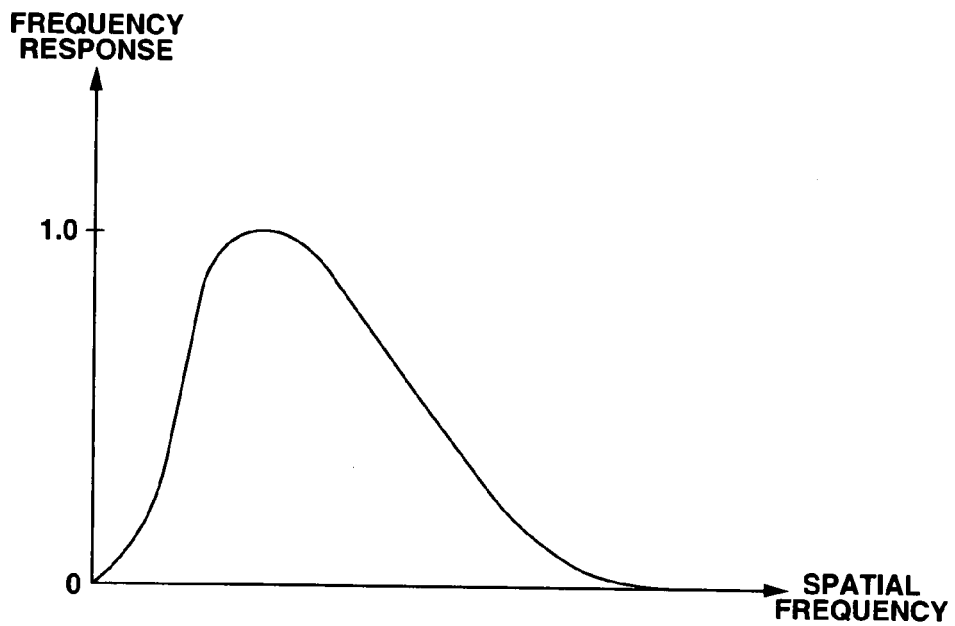
FIG. 47 is a diagram showing a filter property observed during a bandpass filtering process in accordance with the seventh embodiment.

The bandpass filter has, for example, such a property as shown in FIG. 47. FIG. 47 is a diagram showing the filter property of a bandpass filtering process. The filter property is such that a large number of passing components are present in a slightly low frequency band in order to suppress the adverse effect of fine edge components such as vessels as shown in FIG. 47. The filter property is such that, for example, within a spatial frequency band from 0 (zero) to $\pi$ (rad), the passing property exhibits a peak value of (1.0) at $\pi/4$.

Then, a binarization is executed on edge components of an image resulting from the bandpass filtering process, using a threshold (step S274). The binarization sets a predetermined threshold Th3 at 10.0 and extracts an edge component exhibiting a variation of a value larger than the threshold Th3. Pixels with the edge component exhibiting a variation of a value larger than the threshold Th3 are set to have a value 1, whereas the other pixels are set to have a value of 1. The other pixels are set have a value of 0 (zero). Reference character j denotes a number identifying a pixel in the image data on each frame. Then, whether or not the value for the edge component of each pixel exceeds the threshold Th3 is checked to set 1 for the pixels rj having a value larger than the threshold Th3, while setting 0 (zero) for the other pixels. As described above, an image containing the cardia exhibits a rapid variation in brightness. Accordingly, setting a higher threshold Th3 enables the exclusion of other edge components, for example, wrinkles resulting from the deformation of the mucosa.

Then, a cardia determination process is executed to determine whether or not the image with the extracted edge component results from the cardia to determine whether or not the image shows the cardia (step S275). The present embodiment determines whether or not the image shows the cardia by thinning the extracted edge component and using a coincidence with an approximate circle as an evaluation value to determine whether or not the edge component is shaped generally like a circle. Whether or not the edge component is shaped generally like a circle is determined by a Haff conversion or the like.

Figure 48:
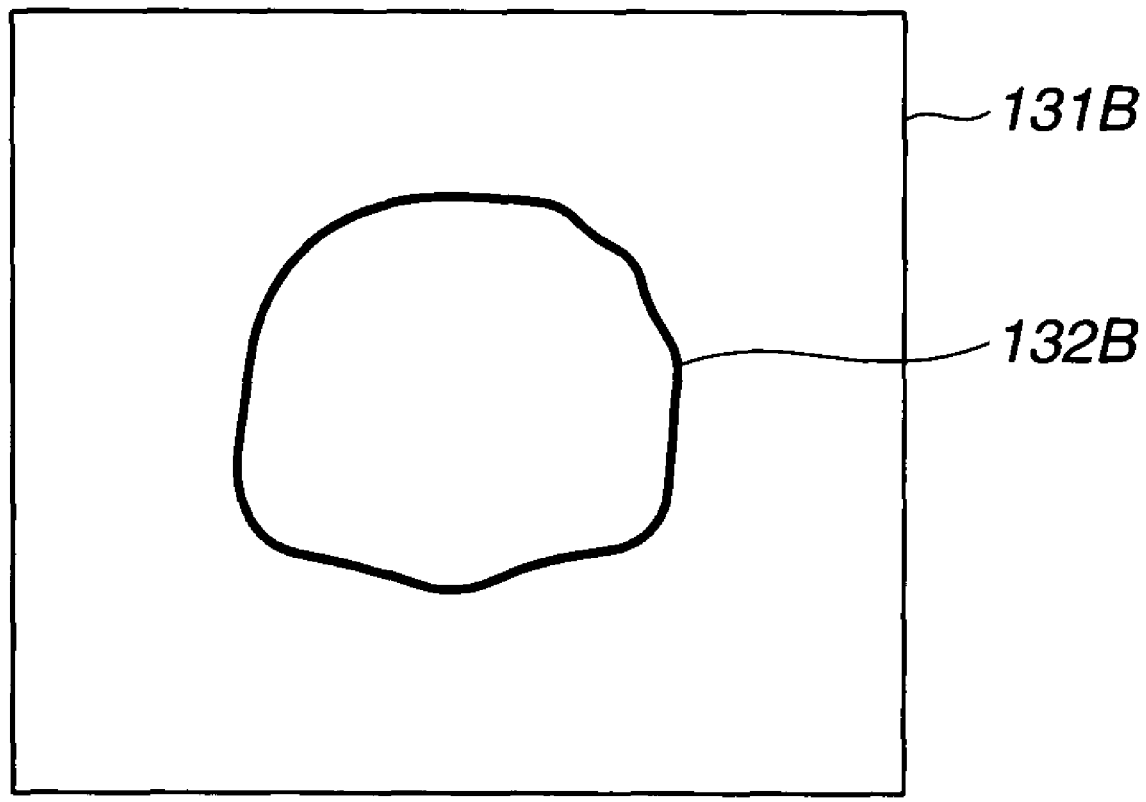
FIG. 48 is a diagram showing an example of an image resulting from the process of predetermined bandpass filtering and binarization executed on the image shown in FIG. 45.

FIG. 48 is a diagram showing an example of an image showing the result of execution of a predetermined process of bandpass filtering and binarization on the image shown in FIG. 45. As shown in FIG. 48, the open cardia has a generally circular shape 132B. Accordingly, the Haff conversion or the like is executed on the edge component image 131B in FIG. 48 to determine whether or not the edge component 132B is shaped like a circle.

If the image is determined to show the cardia on the basis of the result of the cardia determination process, the determination in step S275 is YES. The apparatus thus determines that the cardia has been detected (step S276). The process is then ended.

If the determination in step S275 is NO, that is, the image does not show the cardia, then the apparatus determines that the target site is not the cardia (step S277). The apparatus then determines whether or not the process shown in FIG. 46 has been finished on all of the series of images to be subjected to the process shown in FIG. 46 (step S278). When the process has been finished on all the images, the determination in step S278 is YES. The process is then ended. If the determination in step S278 is NO, there remains an unprocessed image. Thus, a process of changing i to i+1 is executed (step S279). Subsequently, steps S272 to S274 are repeatedly executed on the next image. Steps S273 to S276 constitute a feature value calculation section and a detection section that detects the boundary of the gastrointestinal tract.

Now, variations of the present embodiment will be described below.

In the above example, only the R image data is read in order to make a cardia determination. However, G or B image data or G and B image data may further be read so that a dark portion pixel binarization can be executed on the at least two image data. Then, when the dark portion pixel is determined to have a circular shape in the at least two image data, the apparatus may determine that the cardia has been detected.

In FIG. 46, described above, the cardia is detected on the basis of each frame image. However, as a second variation, the apparatus may determine that the cardia has been detected when the dark portion pixel is determined to have a circular shape in a plurality of consecutive images or at least a predetermined rate (for example, 80%) of the plurality of consecutive images.

Further, in the above description, the process is executed on the plurality of consecutive images. However, as a third variation, the process shown in FIG. 46 may be executed on one image.

As described above, the present embodiment enables the cardia to be detected on the basis of the shape of the open cardia in the image.

In accordance with the present embodiment, the threshold process is applied to the calculated feature value to detect the open cardia. However, for example, an identification function such as a well-known linear discrimination function may be used for the detection. Alternatively, a feature value in accordance with another embodiment may be combined with the present embodiment.

Eighth Embodiment

Now, with reference to the drawings, description will be given of a cardia detection apparatus utilizing a capsule endoscope apparatus and a method for the cardia detection in accordance with an eighth embodiment. The present embodiment is characterized by, in detecting the open cardia on the basis of the shape, utilizing both the detection of the dark portion region boundary and the edge detection, described in the seventh embodiment, to determine whether or not a picked-up image contains the open cardia. Endoscopic images to be processed in accordance with the present embodiment are a series of endoscopic images picked up by the capsule endoscope apparatus 1 as in the case of the fourth embodiment. Accordingly, the configuration of the cardia detection apparatus, a luminal image processing apparatus, is similar to that in the fourth embodiment and will not be described below.

Figure 49:
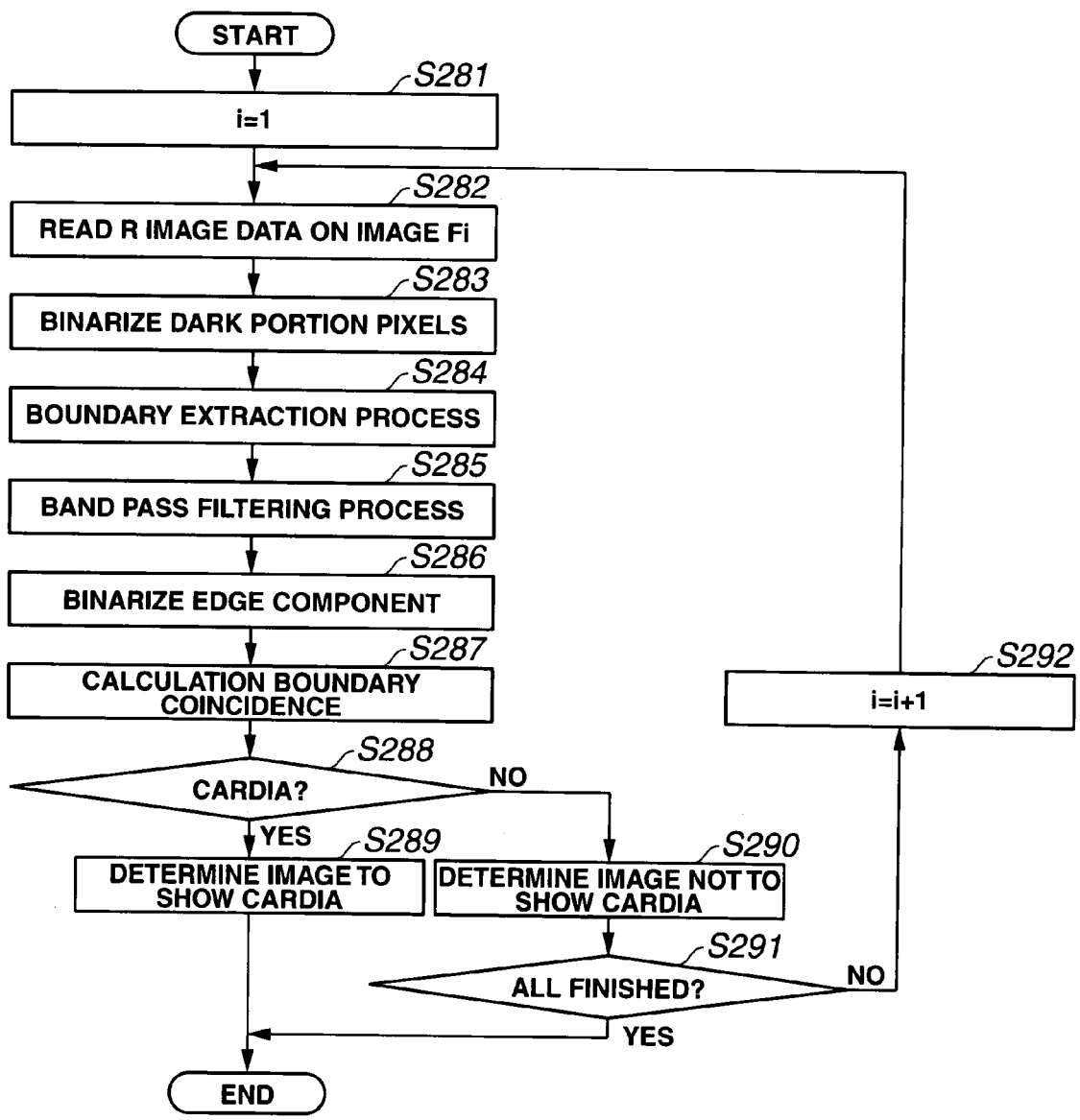
FIG. 49 is a flowchart showing an example of the flow of a process of detecting the cardia on the basis of a series of endoscopic images obtained in accordance with an eighth embodiment.

FIG. 49 is a flowchart showing an example of the flow in which the cardia is detected on the basis of a series of endoscopic images obtained. The series of endoscopic images picked up by the endoscope swallowed through the subject's mouth comprise a plurality of frames. The process shown in FIG. 49 is executed on each of the frames. The image data on each endoscopic image is subjected to a preprocess such as inverse gamma correction or noise removal before the process shown in FIG. 49 is executed.

To start processing with the first frame of the series of images to be subjected to the process shown in FIG. 49, first, the frame number i is set at 1 (step S281). Reference character i denotes an integer from 1 to n.

Then, R image data on the image Fi with the frame number i is read from the storage device (not shown) in the terminal apparatus 7 (step S282). The image Fi comprises three planes for R, G, and B. In this case, only the R image data is read.

A dark portion pixel binarization is executed on all the pixels in the read R image data on the image Fi (step S283). Specifically, the pixel value of each pixel is compared with the predetermined threshold Th2 to execute a binarization such that dark portion pixels are set to have a value of 1, whereas the other pixels are set to have a value of 0 (zero). Reference character j denotes a number identifying a pixel in the image data on each frame. Then, whether or not the value rj for each pixel is smaller than the threshold Th2 is checked to set 1 for pixels having a value smaller than the threshold Th2, while setting 0 (zero) for the other pixels.

Figure 50:
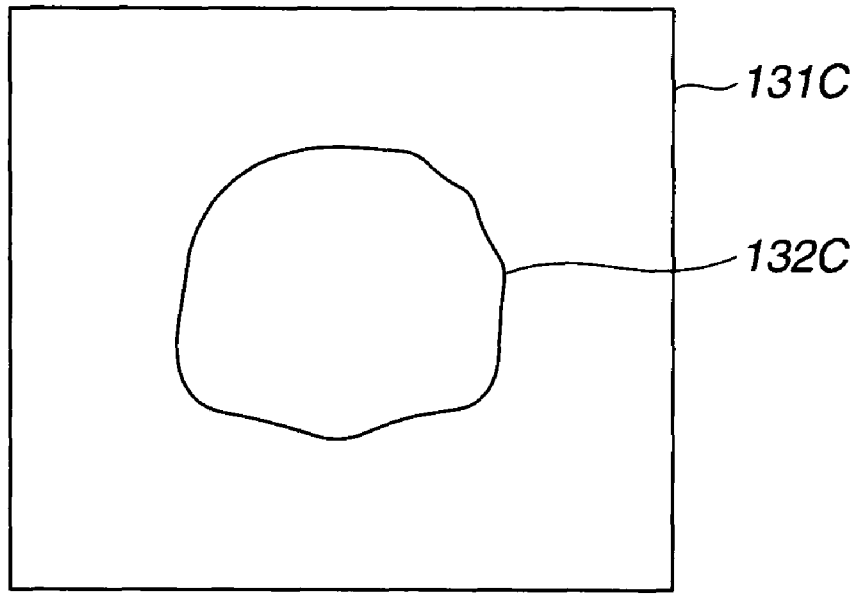
FIG. 50 is a diagram showing an image of an extracted boundary in accordance with the eighth embodiment.

Then, a boundary extraction process is executed to extract the boundary of the extracted dark portion, in other words, to extract the corresponding edge (step S284). The boundary extraction process involves, for example, using a pixel with a value of 1 (dark portion pixel) as a pixel of interest to set a mask region of size 3×3 around the pixel of interest, and if any of the eight pixels in the mask region has a value of 0 (zero), defining the pixel of interest as a boundary pixel having a value of 1. Step S284 constitutes a dark portion boundary extraction step or a dark portion boundary extraction section which extracts the boundary of the dark portion pixel from each image Fi. The boundary extraction process is executed on all the dark portion pixels. FIG. 50 shows an image of an extracted boundary. Executing boundary extraction on an image 131C shown in FIG. 50 results in a generally circular shape 132C along the boundary of the open cardia.

Then, a bandpass filtering process is executed on the read R image data on the image Fi (step S285). The bandpass filtering is implemented by a convolution process using a well-known digital filter or on a Fourier surface as described in the seventh embodiment.

The bandpass filter has, for example, such a property as shown in FIG. 47, described above. The filter property is such that a large number of passing components are present in a slightly low frequency band in order to suppress the adverse effect of fine edge components such as vessels.

Then, a binarization is executed on edge components of an image resulting from the bandpass filtering process, using a threshold (step S286). As described in the seventh embodiment, the binarization, for example, extracts an edge component exhibiting a variation of a value larger than the threshold Th3. Pixels with the edge component exhibiting a variation of a value larger than the threshold Th3 are set to have a value 1, whereas the other pixels are set to have a value of 0 (zero). Reference character j denotes a number identifying a pixel in the image data on each frame. Then, whether or not the value for the edge component of each pixel exceeds the threshold Th3 is checked to set 1 for the pixels rj having a value larger than the threshold Th3, while setting 0 (zero) for the other pixels. As described above, an image containing the cardia exhibits a rapid variation in brightness. Accordingly, setting a higher threshold Th3 enables the exclusion of other edge components, for example, wrinkles resulting from the deformation of the mucosa. An expansion process may be executed on the extracted pixel in order to suppress the adverse effect of the inaccurate detection of the dark portion boundary.

Then, a calculation is made of the coincidence between the boundary pixel extracted in step S284 and the edge component extracted pixel extracted in step S286 as an edge component (step S287). Specifically, the apparatus determines, for each extracted boundary pixel ek1 (k1=1, 2, 3, . . . , K; reference character K denotes the total number of pixels detected as boundary pixels), whether or not a pixel with the same coordinates on the image has also been extracted as an edge component pixel. The number n1 of pixels which are boundary pixels ek1 and which have also been extracted as edge component pixels is counted. This is achieved by performing the logical AND of the boundary pixel ek1 and the edge component of the pixel with the same coordinates on the image. The ratio (n1/K) of the number n1 to the total number K of boundary pixels is calculated.

Figure 51:
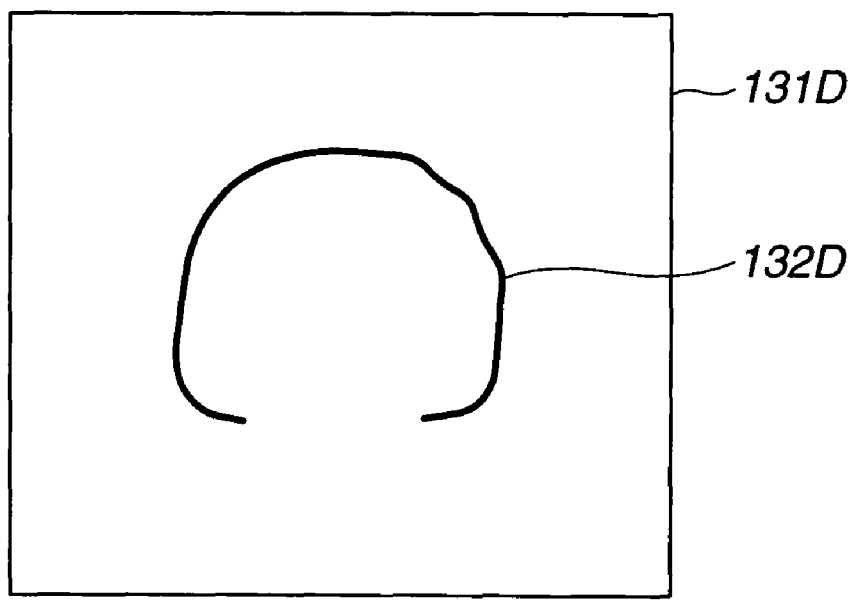
FIG. 51 is a diagram showing an example of an image resulting from the process of predetermined bandpass filtering and binarization executed on a processing target image in accordance with the eighth embodiment.

Then, the apparatus determines whether or not the image contains the cardia on the basis of the ratio (n1/K) indicating the coincidence between the boundary pixel and the edge component extracted pixel (step S288). FIG. 51 is a diagram showing an example of an image obtained by executing a predetermined process of bandpass filtering and binarization on the processing target image. The open cardia has a generally circular shape 32B. However, FIG. 51 shows a break in a part of the circle. In this case, the ratio of the boundary of the dark portion region in FIG. 50 to the edge component in FIG. 51 is calculated to determine whether or not the image shows the cardia.

If the image is determined to show the cardia on the basis of the result of the cardia determination process, the determination in step S288 is YES. The apparatus thus determines that the cardia has been detected (step S289). The process is then ended. Specifically, when the ratio (n1/K) exceeds a predetermined threshold the, the determination in step S288 is YES. The apparatus thus determines that the cardia has been detected (step S289). The process is then ended.

If the determination in step S288 is NO, that is, the ratio (n1/K) does not exceed the predetermined threshold the, then the apparatus determines that the target site is not the cardia (step S290). The apparatus then determines whether or not the process shown in FIG. 49 has been finished on all of the series of images to be subjected to the process shown in FIG. 49 (step S291). When the process has been finished on all the images, the determination in step S291 is YES. The process is then ended. If the determination in step S291 is NO, there remains an unprocessed image. Thus, a process of changing i to i+1 is executed (step S292). Subsequently, steps S282 to S288 are repeatedly executed on the next image. Steps S283 to S289 constitute a feature value calculation section and a detection section that detects the boundary of the gastrointestinal tract.

Now, variations of the present embodiment will be described below.

In the above example, only the R image data is read in order to make a cardia determination. However, G or B image data or G and B image data may further be read so that a dark portion pixel binarization can be executed on the at least two image data. Then, when the coincidence between the at least two image data exceeds the predetermined threshold, the apparatus may determine that the cardia has been detected.

In FIG. 49, described above, the cardia is detected on the basis of each frame image. However, as a second variation, the apparatus may determine that the cardia has been detected when the coincidence exceeds the predetermined threshold in a plurality of consecutive images or at least a predetermined rate (for example, 80%) of the plurality of consecutive images.

Further, in the above description, the process is executed on the plurality of consecutive images. However, as a third variation, the process shown in FIG. 49 may be executed on one image.

As described above, the present embodiment determines whether or not the area extracted as a dark portion has a large edge and can thus make an accurate cardia determination.

Further, the present embodiment can make an accurate cardia determination even if the cardia is not circularly open or if the long distance between the capsule endoscope 3 and the cardia results in a distant view of the cardia.

In accordance with the present embodiment, the threshold process is applied to the calculated feature value to detect the open cardia. However, for example, an identification function such as a well-known linear discrimination function may be used for the detection. Alternatively, a feature value in accordance with another embodiment may be combined with the present embodiment.

Ninth Embodiment

Now, with reference to the drawings, description will be given of a cardia detection apparatus utilizing a capsule endoscope apparatus and a method for the cardia detection in accordance with a ninth embodiment. The present embodiment is characterized by, in detecting the open cardia on the basis of the shape, utilizing both the detection of the dark portion centroid and the edge detection, described in the seventh embodiment, to determine whether or not a picked-up image contains the open cardia. Endoscopic images to be processed in accordance with the present embodiment are a series of endoscopic images picked up by the capsule endoscope apparatus 101 as in the case of the fourth embodiment. Accordingly, the configuration of the cardia detection apparatus, a luminal image processing apparatus, is similar to that in the fourth embodiment and will not be described below.

Process steps similar to those in the eighth embodiment are denoted by similar step numbers and the description of these steps is simplified.

Figure 52:
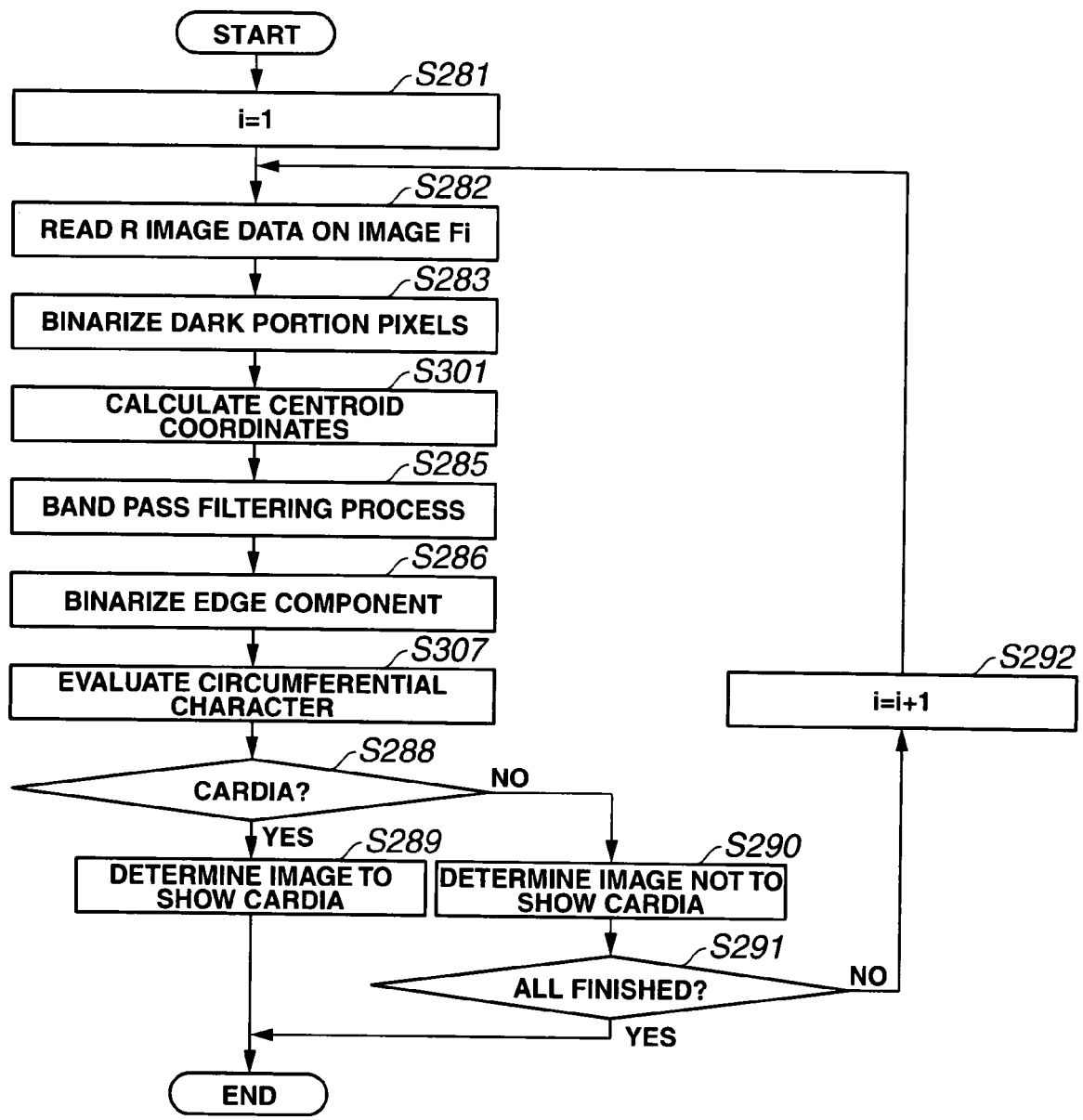
FIG. 52 is a flowchart showing an example of the flow of a process of detecting the cardia on the basis of a series of endoscopic images obtained in accordance with a ninth embodiment.

FIG. 52 is a flowchart showing an example of the flow in which the open cardia is detected on the basis of a series of endoscopic images obtained. In FIG. 52, process steps similar to those in the eighth embodiment are denoted by similar step numbers and the description of these steps is simplified.

The series of endoscopic images picked up by the endoscope swallowed through the subject's mouth comprise a plurality of frames. The process shown in FIG. 52 is executed on each of the frames. The image data on each endoscopic image is subjected to a preprocess such as inverse gamma correction or noise removal before the process shown in FIG. 52 is executed.

To start processing with the first frame of the series of images to be subjected to the process shown in FIG. 52, first, the frame number i is set at 1 (step S281). Reference character i denotes an integer from 1 to n.

Then, R image data on the image Fi with the frame number i is read from the storage device (not shown) in the terminal apparatus 7 (step S282).

A dark portion pixel binarization is executed on all the pixels in the read R image data on the image Fi (step S283). Specifically, the pixel value of each pixel is compared with the predetermined threshold Th2 to execute a binarization such that dark portion pixels are set to have a value of 1, whereas the other pixels are set to have a value of 0 (zero). Reference character j denotes a number identifying a pixel in the image data on each frame. Then, whether or not the value rj for each pixel is smaller than the threshold Th2 is checked to set 1 for pixels having a value smaller than the threshold Th2, while setting 0 (zero) for the other pixels.

Figure 53:
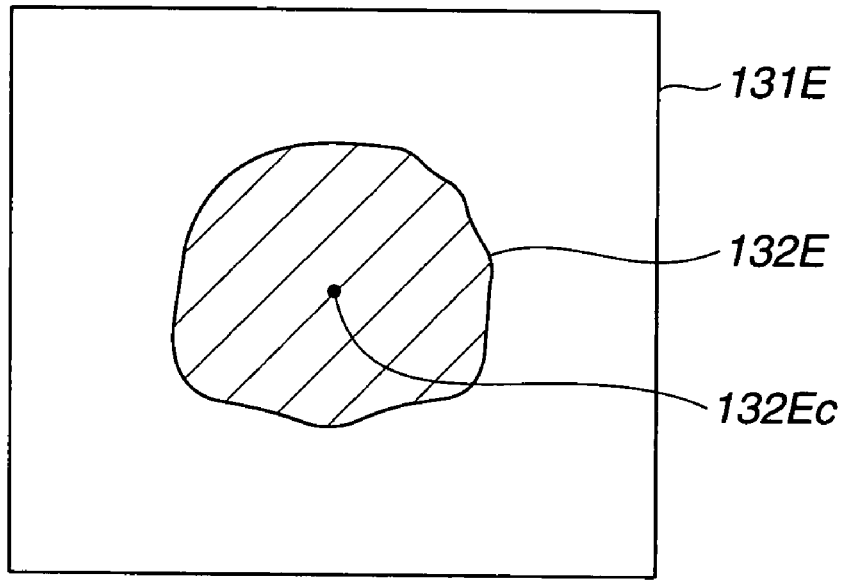
FIG. 53 is a diagram showing the position of a centroid calculated by a dark area centroid coordinate calculation process in accordance with the ninth embodiment.

Then, on the basis of coordinate data on the dark portion region detected by the binarization, the coordinates of the centroid of the dark portion region are calculated (step S301). Step S301 constitutes a dark portion region centroid coordinate calculation step or a dark portion region centroid coordinate calculation section which calculates the coordinates of the centroid of the dark portion region in the image Fi. FIG. 53 shows the centroid position calculated by the dark portion region centroid coordinate calculation section. In an image 131B in FIG. 53, the centroid 132Ec of the dark portion region 132E of the generally circular open cardia is shown at the position of the calculated centroid coordinates.

Then, a bandpass filtering process is executed on the read R image data on the image Fi as described in the eighth embodiment (step S285). Moreover, an edge component binarization is executed on the image resulting from the bandpass filtering process, using a threshold (step S286).

Figure 54:
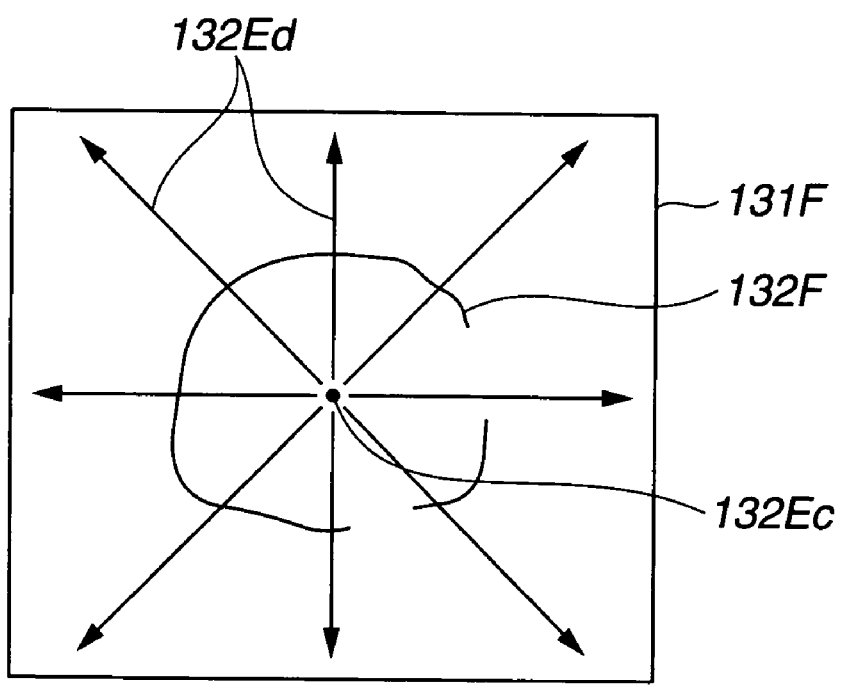
FIG. 54 is a diagram illustrating the evaluation of a circumferential character in accordance with the ninth embodiment.

In step S286, circumferential character is evaluated by determining whether or not the pixel of an edge component extracted in step S286 lies so as to surround the dark portion region (step S307). Specifically, as shown in FIG. 54, the apparatus determines whether or not the extracted edge component pixel is penetrated in predetermined radial directions from the calculated centroid coordinates 132Ec. FIG. 54 is intended to describe the evaluation of the circumferential character. In the example shown in FIG. 54, the number m2 of those of a plurality of radial lines 132Ed extending from the centroid coordinates 132Ec which cross the edge component pixel (this number is hereinafter referred to as the intersection count) is counted. Then, the lines 132Ed cross or penetrate the edge component in seven of the eight directions. Consequently, the intersection count m2 is 7.

Then, the apparatus determines whether or not the image contains the cardia on the basis of the intersection count m2 (step 288). As shown in FIG. 54, even with a break in a part of the circle formed by the edge component pixel, the apparatus determines the image to contain the cardia when the ratio (m2/m3) of the intersection count m2 to the number m3 of the plurality of lines 132Ed exceeds a predetermined threshold Thm. In other words, whether or not the image shows the cardia is determined on the basis of the ratio (m2/m3) of those of the plurality of lines extending radially from the centroid position of the dark portion region in FIG. 53 which cross the edge component pixel in FIG. 54.

If the ratio of the intersection count m2 to the number m3 of the plurality of segments 132Ed exceeds the threshold Thm, the determination in step S288 is YES. The apparatus thus determines that the cardia has been detected (step S289). The process is then ended. Specifically, when the ratio (m2/m3), indicating an evaluative value for the circumferential character, exceeds the predetermined threshold thm, for example, 0.7, the determination in step S88 is YES. The apparatus thus determines that the cardia has been detected (step S289). The process is then ended.

If the determination in step S288 is NO, that is, the ratio (m2/m3) does not exceed the predetermined threshold thm, then the apparatus determines that the target site is not the cardia (step S290). The apparatus then determines whether or not the process shown in FIG. 52 has been finished on all of the series of images to be subjected to the process shown in FIG. 52 (step S291). When the process has been finished on all the images, the determination in step S291 is YES. The process is then ended. If the determination in step S291 is NO, there remains an unprocessed image. Thus, a process of changing i to i+1 is executed (step S292). Subsequently, steps S282 to S288 in FIG. 52 are repeatedly executed on the next image. Steps S283 to S289 constitute a feature value calculation section and a detection section that detects the boundary of the gastrointestinal tract.

Now, variations of the present embodiment will be described below.

In the above example, only the R image data is read in order to make a cardia determination. However, G or B image data or G and B image data may further be read so that a dark portion pixel binarization can be executed on the at least two image data. Then, when the evaluative value for the circumferential character exceeds the predetermined threshold for the at least two image data, the apparatus may determine that the cardia has been detected.

In FIG. 52, described above, the cardia is detected on the basis of each frame image. However, as a second variation, the apparatus may determine that the cardia has been detected when the evaluative value for the circumferential character exceeds the predetermined threshold for a plurality of consecutive images or at least a predetermined rate (for example, 80%) of the plurality of consecutive images.

Further, in the above description, the process is executed on the plurality of consecutive images. However, as a third variation, the process shown in FIG. 52 may be executed on one image.

Figure 55:
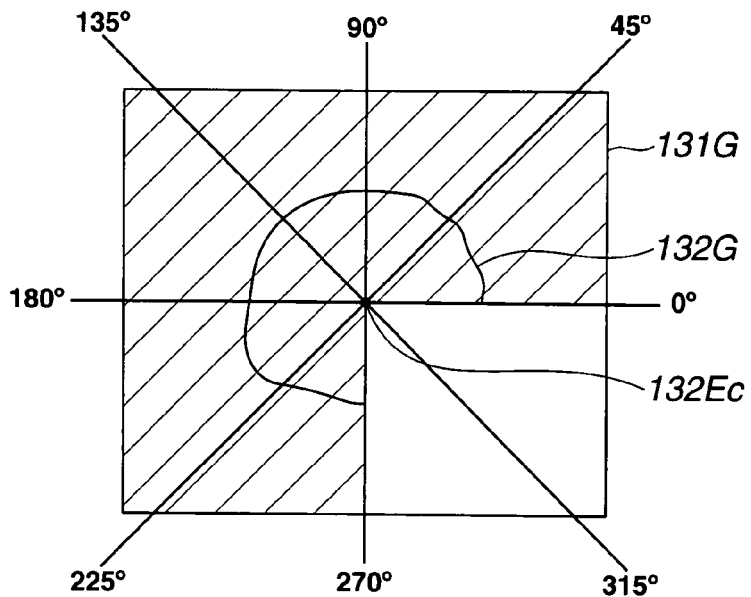
FIG. 55 is a diagram illustrating that the evaluation of the circumferential character is based on area rate in accordance with a fourth variation of the ninth embodiment.
Figure 56:
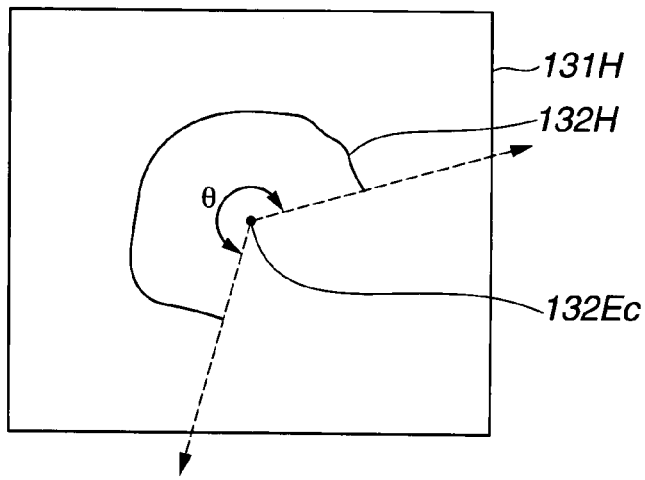
FIG. 56 is a diagram illustrating that the evaluation of the circumferential character is based on angular range in accordance with a fourth variation of a tenth embodiment.

As a fourth variation, the circumferential character may be evaluated on the basis of the number or ratio of those of a plurality of predetermined regions in which the edge component image is present. FIG. 55 is a diagram illustrating that the evaluation of the circumferential character in accordance with the fourth variation is based on the ratio of regions. For example, as shown in FIG. 55, the image is divided into, for example, eight regions around the centroid 132Ec, the regions spanning between 0° and 45°, between 45° and 90°, between 90° and 135°, between 135° and 180°, between 180° and 225°, between 225° and 270°, between 270° and 315°, and between 315° and 360°. The apparatus then determines whether or not each of the regions contains the edge component pixel obtained in step S286. When the number of regions containing the edge component pixel 132G is at least the predetermined threshold, the apparatus may determine that the cardia has been detected. FIG. 56 shows that the edge component pixel is present in 6 shaded regions. If the threshold is 6, the apparatus determines, in the case of FIG. 55, that the cardia has been detected.

Moreover, the apparatus may determine that the cardia has been detected on the basis of the angular range in which the edge component pixel is present, instead of the number of regions. For example, as shown in FIG. 56, the angular range θ around the centroid 132Ec in which the edge component pixel is present is determined. The apparatus may determine that the cardia has been detected on the basis of whether or not the angular range θ is equal to at least the predetermined threshold, for example, at least 270°. FIG. 56 is a diagram illustrating that the circumferential character is evaluated on the basis of the angular range. If a plurality of edge component pixel lines are present, the apparatus may determine whether or not the cardia has been detected by comparing the edge component pixel in the greatest angular range with the predetermined threshold.

As described above, although the dark portion region binarization may undergo a variation in the position of the boundary depending on the threshold Th2, the present embodiment can make an accurate cardia determination without suffering from the adverse effect of a possible variation in boundary position.

Further, the present embodiment can make an accurate cardia determination even if the cardia is not circularly open or if the long distance between the capsule endoscope 103 and the cardia results in a distant view of the cardia.

In accordance with the present embodiment, the threshold process is applied to the calculated feature value to detect the open cardia. However, for example, an identification function such as a well-known linear discrimination function may be used for the detection. Alternatively, a feature value in accordance with another embodiment may be combined with the present embodiment.

Tenth Embodiment

Now, with reference to the drawings, description will be given of a cardia detection apparatus utilizing a capsule endoscope apparatus and a method for the cardia detection in accordance with a tenth embodiment. Endoscopic images to be processed in accordance with the present embodiment are a series of endoscopic images picked up by the capsule endoscope apparatus 101 as in the case of the fourth embodiment. Accordingly, the configuration of the cardia detection apparatus, a luminal image processing apparatus, is similar to that in the fourth embodiment and will not be described below.

In the above sixth to ninth embodiments, the open cardia is detected. However, the cardia may be closed. The cardia detection apparatus in accordance with the present embodiment is characterized by detecting the closed cardia to determine whether or not each image shows that, for example, the capsule endoscope moving from the esophagus toward the stomach is located near and in front of the cardia.

Figure 57:
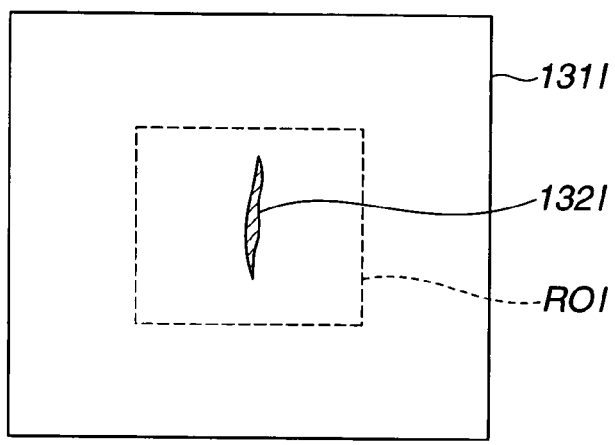
FIG. 57 is a diagram showing an example of an image in which the capsule endoscope is located in front of the closed cardia in accordance with the tenth embodiment.

FIG. 57 is a diagram showing an example of an image in which the capsule endoscope 103 is located in front of the cardia.

When the capsule endoscope 103 picks up an image of the closed cardia in the lumen, the picked-up image contains no definite dark portion region owing to the closed cardia. Moreover, the brightness in the screen is relatively uniform because the periphery of the cardia is viewed from the front at the terminal of the esophagus. The present embodiment determines that the closed cardia has been detected when the area of the closed cardia is smaller than a predetermined size.

Figure 58:
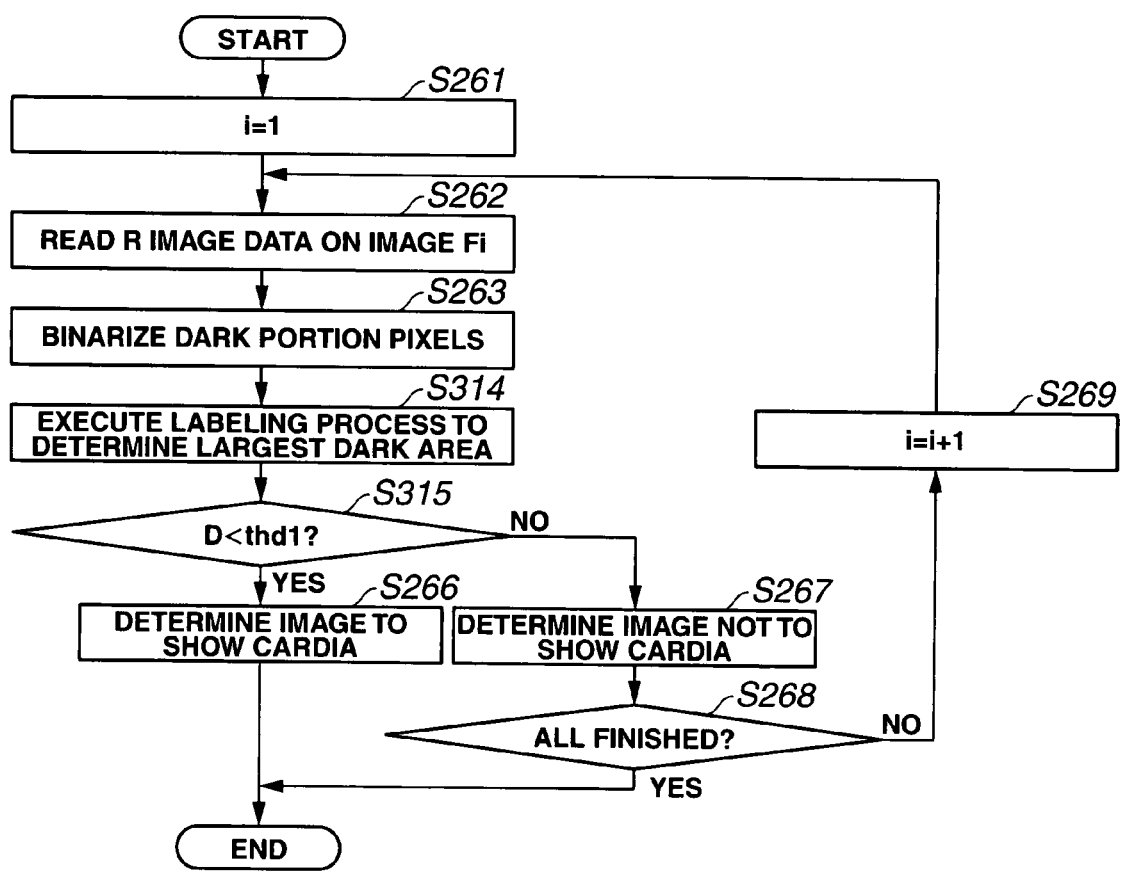
FIG. 58 is a flowchart showing an example of the flow of a process of detecting the cardia on the basis of a series of endoscopic images obtained in accordance with the tenth embodiment.

FIG. 58 is a flowchart showing an example of the flow in which the closed cardia is detected on the basis of a series of endoscopic images obtained. The series of endoscopic images picked up by the endoscope swallowed through the subject's mouth comprise a plurality of frames. The process shown in FIG. 58 is executed on each of the frames. The image data on each endoscopic image is subjected to a pre-process such as inverse gamma correction or noise removal before the process shown in FIG. 58 is executed. The process shown in FIG. 58 includes process steps similar to those of the process shown in FIG. 44. Accordingly, process steps similar to those shown in FIG. 44 are denoted by similar step numbers and the description of these steps is simplified.

To start processing with the first frame of the series of images to be subjected to the process shown in FIG. 58, first, the frame number i is set at 1 (step S261). Reference character i denotes an integer from 1 to n.

Then, R image data on the image Fi with the frame number i is read from the storage device (not shown) in the terminal apparatus 7 (step S262). The image Fi comprises three planes for R, G, and B. In this case, only the R image data is read.

Although in this case, the R image data is read in order to make a cardia determination described below, G or B image data on the image Fi may be used.

A dark portion pixel binarization is executed on all the pixels in the read R image data on the image Fi (step S263). Specifically, the pixel value of each pixel is compared with the predetermined threshold Th2 to execute a binarization such that dark portion pixels are set to have a value of 1, whereas the other pixels are set to have a value of 0 (zero). Reference character j denotes a number identifying a pixel in the image data on each frame. Then, whether or not the value rj for each pixel is smaller than the threshold Th2 is checked to set 1 for pixels having a value smaller than the threshold Th2, while setting 0 (zero) for the other pixels.

Then, a labeling process is executed to label a plurality of regions of the dark portion pixel, and a dark portion region with the largest area D is then identified (step S314). Step S314 constitutes a largest dark portion region identification step or a largest dark portion region identification section which identifies the dark portion region with the largest area D in each image Fi. FIG. 57 shows an image 132I containing a dark portion region 132I with the largest area D.

The apparatus then determines whether or not the largest area D is smaller than a predetermined threshold Thd1 (step S315). The threshold Thd1 is, for example, 0.1.

If the determination in step S315 is YES, that is, the dark portion accounts for less than 10% of the entire image, the apparatus determines that the cardia has been detected (step 266). The process is then ended.

If the determination in step S315 is NO, that is, the dark portion does not account for less than 10% of the entire image, the apparatus determines that the image does not show the cardia (step 267). The apparatus then determines whether or not the process shown in FIG. 58 has been finished on all of the series of images to be subjected to the process shown in FIG. 58 (step S268). When the process has been finished on all the images, the determination in step S268 is YES. The process is then ended. If the determination in step S268 is NO, there remains an unprocessed image. Thus, a process of changing i to i+1 is executed (step S269). Subsequently, steps S262 to S264 are repeatedly executed on the next image.

In step S266, the apparatus determines that the cardia has been detected when the area D of the largest dark portion region is smaller than the predetermined threshold Thd1. In other words, the apparatus may also determine that the capsule endoscope will subsequently pass through the cardia or reach the interior of the stomach. Steps S263 to S266 constitute a feature value calculation section and a detection section that detects the boundary of the gastrointestinal tract.

Now, variations of the present embodiment will be described below.

In the above example, only the R image data is read in order to make a cardia determination. However, G or B image data or G and B image data may further be read so that a dark portion pixel binarization can be executed on the at least two image data. Then, when the areas D of the dark portion regions with the largest area in the at least two image data are all smaller than the predetermined threshold Thd1, the apparatus may determine that the cardia has been detected.

In FIG. 58, described above, the cardia is detected on the basis of each frame image. However, as a second variation, the apparatus may determine that the cardia has been detected when the determination in step S315 is D<Thd1 for a plurality of consecutive images or at least a predetermined rate (for example, 80%) of the plurality of consecutive images.

Further, in the above description, the process is executed on the plurality of consecutive images. However, as a third variation, the process shown in FIG. 58 may be executed on one image.

As a fourth variation, a region of interest (ROI) of such a predetermined size as shown by a dotted line in FIG. 57 may be set around the above dark portion region with the largest area. The standard deviation, variance, or variation coefficient of the brightness in the region of interest (ROI) may then be calculated so that the apparatus can determine that the closed cardia has been detected on the basis of whether or not the value of the standard deviation or the like is smaller than a predetermined threshold.

As described above, the present embodiment allows the closed cardia to be detected on the basis of the area of the dark portion in the image.

In accordance with the present embodiment, the threshold process is applied to the calculated feature value to detect the closed cardia. However, for example, an identification function such as a well-known linear discrimination function may be used for the detection. Alternatively, a feature value in accordance with another embodiment may be combined with the present embodiment.

Eleventh Embodiment

Now, with reference to the drawings, description will be given of a cardia detection apparatus utilizing a capsule endoscope apparatus and a method for the cardia detection in accordance with an eleventh embodiment. Endoscopic images to be processed in accordance with the present embodiment are a series of endoscopic images picked up by the capsule endoscope apparatus 101 as in the case of the fourth embodiment. Accordingly, the configuration of the cardia detection apparatus is similar to that in the fourth embodiment and will not be described below.

The cardia detection apparatus, a luminal image processing apparatus in accordance with the present embodiment, is characterized by detecting the closed cardia to determine whether or not each image shows that, for example, the capsule endoscope moving from the esophagus toward the stomach is located near and in front of the cardia.

Figure 59:
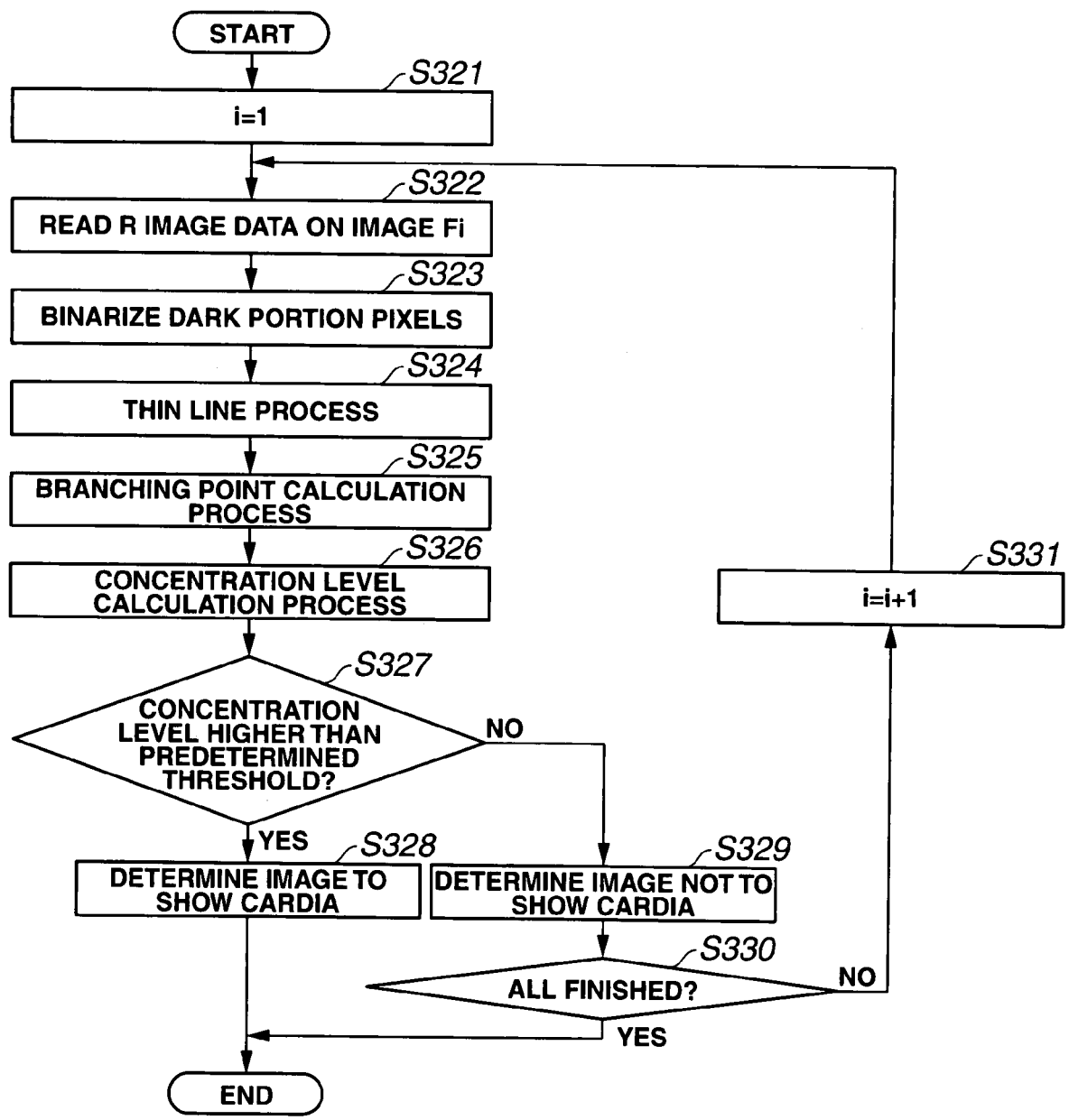
FIG. 59 is a flowchart showing an example of the flow of a process of detecting the cardia on the basis of a series of endoscopic images obtained in accordance with an eleventh embodiment.

FIG. 59 is a flowchart showing an example of the flow in which the closed cardia is detected on the basis of a series of endoscopic images obtained. The series of endoscopic images picked up by the endoscope swallowed through the subject's mouth comprise a plurality of frames. The process shown in FIG. 59 is executed on each of the frames. The image data on each endoscopic image is subjected to a pre-process such as inverse gamma correction or noise removal before the process shown in FIG. 59 is executed.

To start processing with the first frame of the series of images to be subjected to the process shown in FIG. 59, first, the frame number i is set at 1 (step S321). Reference character i denotes an integer from 1 to n.

Then, R image data on the image Fi with the frame number i is read from the storage device (not shown) in the terminal apparatus 7 (step S322). The image Fi comprises three planes for R, G, and B. In this case, only the R image data is read.

Although in this case, the R image data is read in order to make a cardia determination described below, G or B image data on the image Fi may be used.

A dark portion pixel binarization is executed on all the pixels in the read R image data on the image Fi (step S323). Specifically, the pixel value of each pixel is compared with the predetermined threshold Th2 to execute a binarization such that dark portion pixels are set to have a value of 1, whereas the other pixels are set to have a value of 0 (zero). Reference character j denotes a number identifying a pixel in the image data on each frame. Then, whether or not the value rj for each pixel is smaller than the threshold Th2 is checked to set 1 for pixels having a value smaller than the threshold Th2, while setting 0 (zero) for the other pixels.

Figure 60:
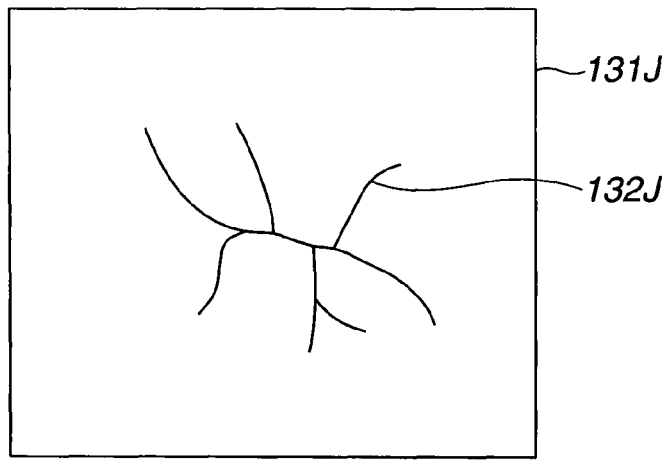
FIG. 60 is a diagram showing an example of an image illustrating the cardia shape expressed with thin lines on the basis of the image of the closed cardia, in accordance with the eleventh embodiment.

Then, a thinning process is executed on the binarized image (step S324). FIG. 60 shows an image 131J containing a cardia shape 132J obtained by thinning the image of the closed cardia. FIG. 60 is a diagram illustrating the cardia shape obtained by thinning the image of the closed cardia. Branching or intersecting points (hereinafter referred to as branching points) are calculated for each of the lines resulting from the thinning operation (step 325). Coordinate data on the branching points is stored in the storage device as data indicating the concentration level.

Then, the concentration level of the calculated branching points is calculated (step S326). Step 326 constitutes a concentration level calculation step or a concentration level calculation section which calculates the concentration level of the branching points in each image Fi. For the concentration level, the variance of the coordinate values of the branching points is used as a parameter.

Figure 61:
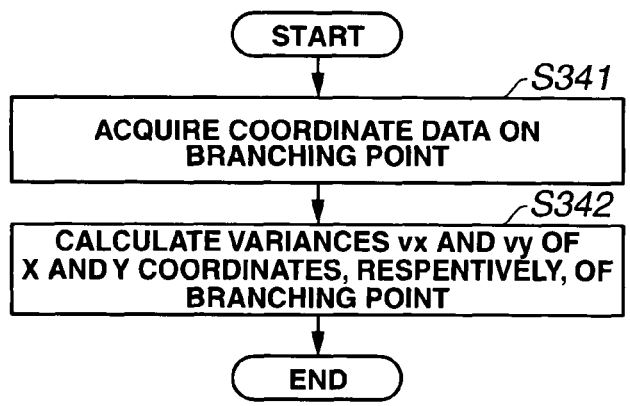
FIG. 61 is a flowchart showing an example of the flow of a process of calculating the variance value, corresponding to the concentration level parameter, in accordance with the eleventh embodiment.

FIG. 61 is a flowchart showing an example of the flow of a process of calculating the variance value, which is a parameter for the concentration level. First, coordinate data on the calculated branching points is acquired from the storage device (step S341). For example, when N branching points have been calculated, the variance vx of the x coordinate of each of the N branching points and the variance vy of the y coordinate of the branching point are calculated (step S342). The variances vx, vy are stored for each of the N branching points.

Referring back to FIG. 59, the apparatus determines whether or not the concentration level is high depending on whether or not the variances vx, vy, which are data indicating the concentration level, are less than thresholds thv1, thv2 (step S327).

If the determination in step S327 is YES, that is, the variances vx, vy are less than thresholds thv1, thv2, respectively, the apparatus determines that the cardia has been detected (step S328). The process is then ended.

If the determination in step S327 is NO, that is, the variances vx, vy are not less than thresholds thv1, thv2, respectively, the apparatus determines that the image does not show the cardia (step S329). The apparatus then determines whether or not the process shown in FIG. 59 has been finished on all of the series of images to be subjected to the process shown in FIG. 59 (step S330). When the process has been finished on all the images, the determination in step S330 is YES. The process is then ended. If the determination in step S330 is NO, there remains an unprocessed image. Thus, a process of changing i to i+1 is executed (step S331). Subsequently, steps S322 to S327 are repeatedly executed on the next image. Steps S323 to S328 constitute a feature value calculation section and a detection section that detects the boundary of the gastrointestinal tract.

Figure 62:
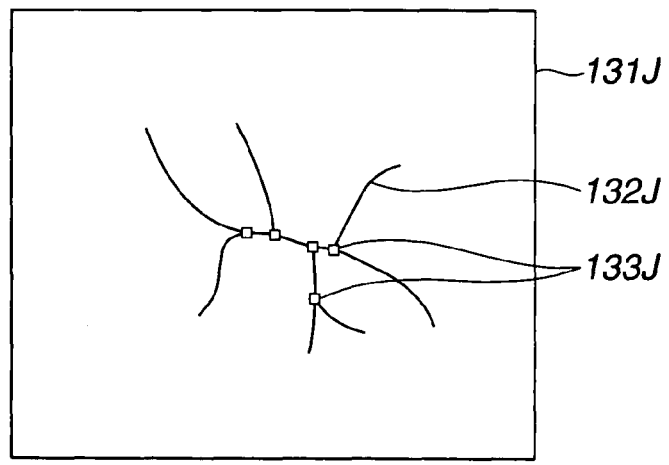
FIG. 62 is a diagram showing an example of an image illustrating branching points in accordance with the eleventh embodiment.

FIG. 62 is a diagram showing an example of an image illustrating branching points. In FIG. 62, for the closed cardia, branching points 133J on a line in the image 131J concentrate in a part of the image 131J. The level of the concentration is digitized on the basis of the above variance to determine, for example, a variance value as described above. The level, for example, the variance value is compared with a predetermined threshold to determine whether or not the closed cardia has been detected. The branching points concentrate in one part when the closed cardia is thinned. Accordingly, the apparatus determines that the cardia has been detected when the branching points are found to concentrate in one part.

In step S328, the apparatus determines that the closed cardia has been detected when the variance value is smaller than the predetermined threshold. In other words, the apparatus may also determine that the capsule endoscope 103 will subsequently pass through the cardia or reach the interior of the stomach.

Now, variations of the present embodiment will be described below.

In the above example, only the R image data is read in order to make a cardia determination. However, G or B image data or G and B image data may further be read so that the concentration level can be calculated for the at least two image data. Then, the apparatus may determine that the cardia has been detected on the basis of the concentration levels for the at least two image data.

In FIG. 59, described above, the cardia is detected on the basis of each frame image. However, as a second variation, the apparatus may determine that the closed cardia has been detected when the determination in step S327 is YES for a plurality of consecutive images or at least a predetermined rate (for example, 80%) of the plurality of consecutive images.

Further, in the above description, the process is executed on the plurality of consecutive images. However, as a third variation, the process shown in FIG. 29 may be executed on one image.

In accordance with the present embodiment, the threshold process is applied to the calculated feature value to detect the closed cardia. However, for example, an identification function such as a well-known linear discrimination function may be used for the detection. Alternatively, a feature value in accordance with another embodiment may be combined with the present embodiment.

The plurality of embodiments described above each make it possible to detect when, for example, the endoscope has passed through the EG junction or is about to reach the cardia, on the basis of one endoscopic image or a series of consecutive endoscopic images. This enables images required for diagnosing the esophageal disease to be selected from a large number of picked-up endoscopic images, allowing the esophageal disease to be quickly diagnosed.

Therefore, the plurality of embodiments described above can provide a luminal image processing apparatus that can detect the cardia.

For example, a determination for the Barrett esophagus is made on the basis of an image of the vicinity of the EG junction. Thus, the ability to detect the cardia as described above enables the disease to be carefully diagnosed while viewing only that image or only the image preceding or succeeding that image. This allows the diagnosis to be quickly achieved.

Description has been given of the example of the process using images picked up by the capsule endoscope 3. However, of course, the above process may be executed on images picked up by a normal endoscope, that is, an endoscope having an elongate, flexible insertion portion. Both the capsule endoscope and the normal endoscope can provide intraluminal images.

Moreover, the cardia can be detected by each of the techniques in accordance with the plurality of embodiments described above (including the variations). However, the cardia may be detected by a combination of a plurality of the techniques.

The above fourth to eleventh embodiments and variations thereof can provide a luminal image processing apparatus that can detect the cardia on the basis of intraluminal images.

INDUSTRIAL APPLICABILITY

To make a determination for the Barrett esophagus condition or the like on the basis of a large amount of endoscopic image data obtained by picking up images of the interior of the esophagus, a process of detecting a first feature such as the EG junction or the epithelium boundary which is located around the target site is repeated with a frame number sequentially changed until the presence of the feature is determined. For images succeeding the image determined to contain the first feature, the process shifts to detection of a second feature such as the Barrett esophagus which corresponds to a determination target. This process is more efficient than a process of detecting the second feature and then making a determination therefor without detecting the first feature.

The invention claimed is:

1. A medical image processing apparatus comprising:
an image extracting section that extracts a frame image from in vivo motion picture data picked up by an in vivo image pickup device or a plurality of consecutively picked-up still image data; and
an image analysis section that analyzes the frame image extracted by the image extracting section to output an image analysis result, the image analysis section comprising:
a first biological feature detection section that detects a first biological feature;
a second biological feature detection section that detects, on the basis of a detection result obtained by the first biological feature detection section, a second biological feature in a frame image picked up temporally before or after the image used for detection by the first biological feature detection section; and
a condition determination section that makes a determination for a biological condition on the basis of a detection result obtained by the second biological feature detection section to output the determination,
wherein on the basis of the detection result obtained by the first biological feature detection section, the second biological feature detection section acquires a predetermined number of frame images to execute a process of detecting the second biological feature on the frame image.

2. The medical image processing apparatus according to claim 1, wherein
on the basis of the detection result obtained by the first biological feature detection section, the second biological feature detection section sequentially acquires a frame image picked up temporally before or after the frame image processed by the first biological feature detection section, and
when the second biological feature detection section sequentially acquires the frame image and on the basis of the detection result obtained by the first biological feature detection section by processing the frame image acquired, the second biological feature detection section suspends the acquisition of the frame image.

3. The medical image processing apparatus according to claim 1, wherein the first biological feature detected by the first biological feature detection section is the epithelium boundary corresponding to a boundary between the squamous epithelium in the esophagus and a columnar epithelium in the stomach.

4. The medical image processing apparatus according to claim 3, wherein the condition determination section makes a determination for the biological condition only for the frame image in which the epithelium boundary has been detected, on the basis of the detection result obtained by the second biological feature detection section.

5. The medical image processing apparatus according to claim 1, wherein
the first biological feature detected by the first biological feature detection section is the cardia serving as an inlet through which the apparatus moves from the esophagus into the cardia, an inlet of the stomach,
on the basis of the detection result obtained by the first biological feature detection section, the second biological feature detection section detects the second biological feature in the frame image picked up temporally before the image used for detection by the first biological feature detection section.

6. The medical image processing apparatus according to claim 5, wherein the first biological feature detection section detects a thin line obtained by executing a thinning process on the frame image, as the closed cardia on the basis of a concentration level of the calculated number of branching points or intersecting points.

7. The medical image processing apparatus according to claim 6, wherein the first biological feature detection section detects the cardia as the open cardia on the basis of a thinned image generated by executing an edge extraction process and a binarization on the frame image and a dark portion image obtained by executing a dark portion extraction process of extracting an image dark portion on the frame image.

8. The medical image processing apparatus according to claim 7, wherein the cardia is detected on the basis of a region in which or an angle at which a thin line in the thinned image is present in a circumferential direction around a feature point in the dark portion.

9. The medical image processing apparatus according to claim 1, wherein the condition determination section makes a determination for the biological condition by determining whether or not the Barrett esophagus as an intraesophageal disease is present.

10. The medical image processing apparatus according to claim 9, wherein the first biological feature detected by the first biological feature detection section is an EG junction located in the esophagus as a boundary between the stomach and the esophagus.

11. The medical image processing apparatus according to claim 10, wherein the first biological feature detection section detects the EG junction by extracting coordinates of end points of palisade vessels and obtaining a palisade vessel end point boundary line formed of a segment connecting the extracted end point coordinates.

12. The medical image processing apparatus according to claim 11, wherein when a segment obtained by executing a thinning process on the frame image has at least a predetermined length, the first biological feature detection section determines the segment to be the palisade vessel.

13. The medical image processing apparatus according to claim 12, wherein the first biological feature detection section determines the segment obtained by executing the thinning process on the frame image data to be the palisade vessel, further taking into account the numbers of branching points, intersecting points, and bending points on the segment.

14. The medical image processing apparatus according to claim 13, wherein the first biological feature detection section determines the segment obtained by executing the thinning process on the frame image data to be the palisade vessel, further taking into account an angle between a segment connecting opposite ends of the segment and a vector connecting a dark portion center of an image dark portion of the frame image to one of the opposite ends which is closer to the image dark portion.

15. The medical image processing apparatus according to claim 10, wherein the second biological feature detected by the second biological feature detection section is an epithelium boundary in the esophagus.

16. The medical image processing apparatus according to claim 15, wherein the condition determination section determines whether or not the Barrett esophagus is present on the basis of a distance between a plurality of intersecting points between the epithelium boundary and each of a plurality of radial lines radiating from a predetermined point and between the EG junction and the radial line.

17. The medical image processing apparatus according to claim 16, wherein the condition determination section determines whether or not the Barrett esophagus is present, taking into account distances between a predetermined point and the epithelium boundary crossing each of the plurality of radial lines radiating from the predetermined point or distances between the EG junction and the predetermined point.

18. The medical image processing apparatus according to claim 15, wherein the condition determination section determines whether or not the Barrett esophagus is present, further on the basis of the number of points at which the palisade vessel crosses the epithelium boundary.

19. The medical image processing apparatus according to claim 18, wherein when a segment obtained by executing a thinning process on the frame image has at least a predetermined length, the first biological feature detection section determines the segment to be the palisade vessel.

20. The medical image processing apparatus according to claim 19, wherein the first biological feature detection section determines the segment obtained by executing the thinning process on the frame image data to be the palisade vessel, further taking into account the numbers of branching points, intersecting points, and bending points on the segment.

21. The medical image processing apparatus according to claim 20, wherein the first biological feature detection section determines the segment obtained by executing the thinning process on the frame image data to be the palisade vessel, further taking into account an angle between a segment connecting opposite ends of the segment and a vector connecting a dark portion center of an image dark portion of the frame image to one of the opposite ends which is closer to the image dark portion.

22. A medical image processing method comprising:
 a step of extracting a frame image from in vivo motion picture data picked up by an in vivo image pickup device or a plurality of consecutively picked-up still image data;
 a step of analyzing the extracted frame image to detect a first biological feature;
 a step of detecting, on the basis of a result of the detection of the first biological feature, a second biological feature in a frame image picked up temporally before or after the image used for detection by the first biological feature detection section; and
 a step of making a determination for a biological condition on the basis of a result of the detection of the second biological feature to output the determination
 wherein on the basis of the result of the detection of the first biological feature, the second biological feature acquires a predetermined number of frame images to execute the step of detecting the second biological feature in the frame image.

23. A program embodied on non-transitory computer-readable medium allowing a computer to execute:
 a function of extracting a frame image from in vivo motion picture data picked up by an in vivo image pickup device or a plurality of consecutively picked-up still image data
 a function of analyzing the extracted frame image to detect a first biological feature;
 a function of detecting, on the basis of a result of the detection of the first biological feature, a second biological feature in a frame image picked up temporally before or after the image used for detection by the first biological feature detection section; and
 a function of making a determination for a biological condition on the basis of a result of the detection of the second biological feature to output the determination
 wherein on the basis of the result of the detection of the first biological feature, the second biological feature acquires a predetermined number of frame images to execute the function of detecting the second biological feature in the frame image.

* * * * *